US010646583B2

(12) United States Patent
Pereira et al.

(10) Patent No.: US 10,646,583 B2
(45) Date of Patent: *May 12, 2020

(54) ANTIBODY DRUG CONJUGATES (ADC) THAT BIND TO CD37 PROTEINS

(71) Applicant: AGENSYS, INC., Santa Monica, CA (US)

(72) Inventors: Daniel Sousa Pereira, Los Angeles, CA (US); Faisal Hayat Malik, Cerritos, CA (US); Josh Snyder, Santa Monica, CA (US); Leslie Renee Butterworth, Kirkland, WA (US); Ssucheng Jeff Hsu, Pinole, CA (US); Peng Yang, Los Angeles, CA (US); Claudia Isabel Guevara, South Gate, CA (US)

(73) Assignee: AGENSYS, INC., Santa Monica, CA (US)

(*) Notice: Subject to any disclaimer, the term of this patent is extended or adjusted under 35 U.S.C. 154(b) by 153 days.

This patent is subject to a terminal disclaimer.

(21) Appl. No.: 15/892,401

(22) Filed: Feb. 8, 2018

(65) Prior Publication Data

US 2018/0236096 A1    Aug. 23, 2018

Related U.S. Application Data

(63) Continuation of application No. 14/447,209, filed on Jul. 30, 2014, now Pat. No. 9,925,273.

(60) Provisional application No. 61/861,321, filed on Aug. 1, 2013.

(51) Int. Cl.
| A61K 39/00 | (2006.01) |
| A61K 47/68 | (2017.01) |
| A61K 45/06 | (2006.01) |

(52) U.S. Cl.
CPC .......... *A61K 47/6851* (2017.08); *A61K 45/06* (2013.01); *A61K 47/6803* (2017.08); *A61K 47/6811* (2017.08); *A61K 47/6849* (2017.08)

(58) Field of Classification Search
CPC .................................................. A61K 47/6851
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maaaio |
| 4,294,757 | A | 10/1981 | Osaka et al. |
| 4,307,016 | A | 12/1981 | Osaka et al. |
| 4,313,946 | A | 2/1982 | Powell et al. |
| 4,315,929 | A | 2/1982 | Peoria et al. |
| 4,322,348 | A | 3/1982 | Takatsuki et al. |
| 4,331,598 | A | 5/1982 | Kwanishi et al. |
| 4,361,650 | A | 11/1982 | Osaka et al. |
| 4,362,663 | A | 12/1982 | Kawanishi et al. |
| 4,364,866 | A | 12/1982 | Osaka et al. |
| 4,366,241 | A | 12/1982 | Tom et al. |
| 4,371,533 | A | 2/1983 | Kobe et al. |
| 4,424,219 | A | 1/1984 | Osaka et al. |
| 4,486,414 | A | 12/1984 | Pettit et al. |
| 4,676,980 | A | 6/1987 | Segal et al. |
| 4,816,444 | A | 3/1989 | Pettit et al. |
| 4,816,567 | A | 3/1989 | Cabilly et al. |
| 4,879,278 | A | 11/1989 | Pettit et al. |
| 4,880,935 | A | 11/1989 | Thoroe et al. |
| 4,970,198 | A | 11/1990 | Lee et al. |
| 4,975,278 | A | 12/1990 | Senter et al. |
| 4,978,944 | A | 12/1990 | Pettit et al. |
| 4,986,988 | A | 1/1991 | Pettit et al. |
| 5,053,394 | A | 10/1991 | Ellestad et al. |
| 5,076,973 | A | 12/1991 | Pettit et al. |
| 5,079,233 | A | 1/1992 | Lee |
| 5,122,368 | A | 6/1992 | Greenfield et al. |
| 5,138,036 | A | 8/1992 | Pettit et al. |
| 5,208,020 | A | 5/1993 | Chari et al. |
| 5,223,409 | A | 6/1993 | Ladner et al. |
| 5,403,484 | A | 4/1995 | Ladner et al. |
| 5,410,024 | A | 4/1995 | Pettit et al. |
| 5,416,064 | A | 5/1995 | Chari et al. |
| 5,427,908 | A | 6/1995 | Dower et al. |
| 5,476,996 | A | 12/1995 | Wilson et al. |
| 5,504,191 | A | 4/1996 | Pettit et al. |

(Continued)

FOREIGN PATENT DOCUMENTS

| EP | 0404097 A2 | 12/1990 |
| EP | 1391213 A1 | 2/2004 |

(Continued)

OTHER PUBLICATIONS

Alley et al., "Controlling the location of drug attachment in antibody-drug conjugates," Cancer Res (2004) 64:145 Abs 627.
Angal, et al., "A single amino acid substitution abolishes the heterogeneity of chimeric mouse/human (IaG4) antibody," Mol. Immunol. (1993) 30(1):105-08.
Baldwin et al., "Monoclonal antibodies in cancer treatment," The Lancet (1986) pp. 603-605.
Brand et al., "Prospect for anti-HER2 receptor therapy in breast cancer", Anticancer Res., 26(1B):463-470 (2006).
Braslawsky et al., "Adriamycin(hydrazine)-antibody conjugates require internalization and intracellular acid hydrolysis for antitumore activity," Cancer Immuno Immunother (1991) 33(6):367-374.

(Continued)

*Primary Examiner* — Sheela J. Huff
(74) *Attorney, Agent, or Firm* — Jones Day

(57) ABSTRACT

Antibody drug conjugates (ADC's) that bind to CD37 protein and variants thereof are described herein. CD37 exhibits a distinct and limited expression pattern in normal adult tissue(s), and is aberrantly expressed in the cancers listed in Table I. Consequently, the ADC's of the invention in some embodiments provide a therapeutic composition for the treatment of cancer.

22 Claims, 21 Drawing Sheets
Specification includes a Sequence Listing.

(56) References Cited

U.S. PATENT DOCUMENTS

| | | | |
|---|---|---|---|
| 5,521,284 | A | 5/1996 | Pettit et al. |
| 5,530,097 | A | 6/1996 | Pettit et al. |
| 5,545,806 | A | 8/1996 | Lonbera et al. |
| 5,554,725 | A | 9/1996 | Pettit et al. |
| 5,569,825 | A | 10/1996 | Lonberq et al. |
| 5,571,698 | A | 11/1996 | Ladner et al. |
| 5,580,717 | A | 12/1996 | Dower et al. |
| 5,585,089 | A | 12/1996 | Queen et al. |
| 5,599,902 | A | 2/1997 | Pettit et al. |
| 5,606,040 | A | 2/1997 | McGahren et al. |
| 5,622,929 | A | 4/1997 | Willner et al. |
| 5,624,821 | A | 4/1997 | Winter et al. |
| 5,625,126 | A | 4/1997 | Lonbera et al. |
| 5,633,425 | A | 5/1997 | Lonberq et al. |
| 5,635,483 | A | 6/1997 | Pettit et al. |
| 5,648,260 | A | 7/1997 | Winter et al. |
| 5,661,016 | A | 8/1997 | Lonberq et al. |
| 5,663,149 | A | 9/1997 | Pettit et al. |
| 5,665,860 | A | 9/1997 | Pettit et al. |
| 5,677,425 | A | 10/1997 | Bodmer et al. |
| 5,693,762 | A | 12/1997 | Queen et al. |
| 5,698,767 | A | 12/1997 | Wilson et al. |
| 5,712,374 | A | 1/1998 | Kuntsmann et al. |
| 5,714,586 | A | 2/1998 | Kuntsmann et al. |
| 5,739,116 | A | 4/1998 | Hamann et al. |
| 5,767,285 | A | 6/1998 | Hamann et al. |
| 5,770,701 | A | 6/1998 | Mcqahren et al. |
| 5,770,710 | A | 6/1998 | Mcqahren et al. |
| 5,773,001 | A | 6/1998 | Hamann et al. |
| 5,780,588 | A | 7/1998 | Pettit et al. |
| 5,824,805 | A | 10/1998 | Kina et al. |
| 5,869,046 | A | 2/1999 | Presta et al. |
| 5,877,296 | A | 3/1999 | Hamann et al. |
| 5,885,793 | A | 3/1999 | Griffiths et al. |
| 5,969,108 | A | 10/1999 | McCafferty et al. |
| 6,034,065 | A | 3/2000 | Pettit et al. |
| 6,107,540 | A | 8/2000 | Sawyer et al. |
| 6,121,022 | A | 9/2000 | Presta et al. |
| 6,165,745 | A | 12/2000 | Ward et al. |
| 6,172,197 | B1 | 1/2001 | McCafferty et al. |
| 6,194,551 | B1 | 2/2001 | Idusoqie et al. |
| 6,214,345 | B1 | 4/2001 | Firestone et al. |
| 6,239,104 | B1 | 5/2001 | Pettit et al. |
| 6,277,375 | B1 | 8/2001 | Ward |
| 6,323,315 | B1 | 11/2001 | Pettit et al. |
| 6,441,163 | B1 | 8/2002 | Chari et al. |
| 6,521,404 | B1 | 2/2003 | Griffiths et al. |
| 6,528,313 | B1 | 3/2003 | Le Mouellic et al. |
| 6,528,314 | B1 | 3/2003 | Le Mouellic et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,586,251 | B2 | 7/2003 | Economides et al. |
| 6,593,081 | B1 | 7/2003 | Griffiths et al. |
| 6,596,541 | B2 | 7/2003 | Murphy et al. |
| 6,638,768 | B1 | 10/2003 | Le Mouellic et al. |
| 6,657,103 | B1 | 12/2003 | Kucherlapati et al. |
| 7,105,348 | B2 | 9/2006 | Murphy et al. |
| 9,925,273 | B2 * | 3/2018 | Pereira ............ A61K 45/06 |
| 2003/0083263 | A1 | 5/2003 | Doronina et al. |
| 2003/0153043 | A1 | 8/2003 | Carr et al. |
| 2005/0009751 | A1 | 1/2005 | Senter et al. |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2007/0059306 | A1 | 3/2007 | Grosmaire et al. |

FOREIGN PATENT DOCUMENTS

| | | |
|---|---|---|
| JP | 2006500333 A | 1/2006 |
| JP | 2013524777 A | 6/2013 |
| RU | 2436796 C2 | 12/2011 |
| TW | 201302795 A1 | 1/2013 |
| WO | W0 1993011161 A1 | 6/1993 |
| WO | W0 1993021232 A1 | 10/1993 |
| WO | W0 1994011026 A2 | 5/1994 |
| WO | W0 1998016628 A1 | 4/1998 |
| WO | W0 1999058572 A1 | 11/1999 |
| WO | W0 2002043478 A2 | 6/2002 |
| WO | W0 2002088172 A2 | 11/2002 |
| WO | W0 2004010957 A2 | 2/2004 |
| WO | WO 2005084390 A2 | 9/2005 |
| WO | WO 2005084390 A3 | 9/2005 |
| WO | W0 2005092380 A2 | 10/2005 |
| WO | W0 2006034488 A2 | 3/2006 |
| WO | WO 2007140371 A2 | 12/2007 |
| WO | WO 2007140371 A3 | 12/2007 |
| WO | W0 2009019312 A2 | 2/2009 |
| WO | WO 2009099719 A2 | 8/2009 |
| WO | WO 2009099719 A3 | 8/2009 |
| WO | W0 2011092295 A2 | 8/2011 |
| WO | W0 2011112978 A1 | 9/2011 |
| WO | WO 2012131527 A1 | 10/2012 |
| WO | WO 2013088363 A1 | 6/2013 |

OTHER PUBLICATIONS

Bruggemann et al., "A repertoire of monoclonal antibodies with human heavy chains from transgenic mice," Proc. Natl. Acad. Sci. USA (1989) 86:6709-6713.

Carter et al., "Humanization of an anti-p185HER2 antibody for human cancer therapy," Proc Natl Acad Sci USA (1992) 89(10):4285-4289.

Chart et al., "Immunoconjugates containing novel maytansinoids: Promising anticancer drugs," Cancer Res (1992) 52:127-131.

Clackson et al., "Making antibody fragments using phage display libraries," Nature (1991) 352(6336): 624-628.

Cole et al. Monoclonal Antibodies and Cancer Therapy (1985) 77-96.

Communication pursuant to Rules 161(1) and 162 EPC, dated Mar. 23, 2016, 2 pages.

Davidoff et al., "Bone marrow-derived cells contribute to tumor neovasculature and, when modified to express an angiogenesis inhibitor, can restrict tumor growth in mice," Clin Cancer Res (2001) 7(9):2870-2879.

Doronina et al., "Development of potent monoclonal antibody auristatin conjugates for cancer therapy," Nature Biotechnology (2003) 21(7):778-784.

Dubowchik et al., "Receptor-mediated and enzyme-dependent targeting of cytotoxic anticancer drugs," Pharm Therap (1999) 83(2):67-123.

Fan et al., "Antitumor effect of anti-epidermal growth factor receptor monoclonal antibodies plus cis-diamminedichloroplatinum on well established A431 cell xenografts," Cancer Res (1993) 53:4637-4642.

Green et al., "Regulation of B cell development by variable gene complexity in mice reconstituted with human immunoglobulin yeast artificial chromosomes,"(1998) J. Exp. Med. 188(3):483-95.

Hamblett et al., "Effect of drug loading on the pharmacology, pharmacokinetics, and toxicity of an anti-CD30 antibody-drug conjugate," Cancer Res (2004) 64:144 Abs 624.

Hamel et al., "Binding of dolastatin 10 to tubulin at a distinct site for peptide antimitotic agents near the exchangeable nucleotide and vinca alkaloid sites," J Biol Chem (1990) 265(28):17141-17149.

Hancock et al., "A monoclonal antibody against the c-erbB-2 protein enhances the cytotoxicity of cis-diamminedichloroplatinum against human breast and ovarian tumor cell lines," Cancer Res (1991) 51(17):4575-4580.

Henikoff et al., "Amino acid substitution matrices from protein blocks," Proc Natl Acad Sci USA (1992) 89(22):10915-10919.

Hinman et al., "Preparation and characterization of monoclonal antibody conjugates of the calicheamicins: a novel and potent family of antitumor antibiotics," Cancer Res (1993) 53(14):3336-3342.

Holliger, et al., "Diabodies: small bivalent and bispecific antibody fragments," Proc. Natl. Acad. Sci. U.S.A. (1993) 90(14):6444-48.

Hopp et al., "Prediction of protein antigenic determinants from amino acid sequences,", Proc Natl Acad Sci U.S.A. (1981) 78(6):3824-3828.

(56) References Cited

OTHER PUBLICATIONS

Horejsi et al., "Novel structurally distinct family of leucocyte surface glycoproteins including CD9, CD37, CD53 and CD63," FEBS Lett (1991) 288(1-2):1-4.
Huston et al. "Protein engineering of antibody binding sites: recovery of specific activity in an anti-digoxin single-chain Fv analogue produced in *Escherichia coli*," Proc. Natl. Acad. Sci. USA (1988) 85(16):5879-5883.
International Preliminary Report on Patentability for PCT/US2014/048915, dated Feb. 2, 2016, 7 oaaes.
International Search Report and Written Opinion for PCT/US2014/048915, dated Nov. 20, 2014, 10 oaaes.
Jakobovits, "Production and selection of antigen-specific fully human monoclonal antibodies from mice engineered with human lg loci," Adv. Drug Del. Rev. (1998) 31:33-42.
Johnson et al., "Anti-tumor activity of CC49-doxorubicin immunoconjugates," Anticancer Res (1995) 15(4):1387-1393.
Kasprzyk et al., "Therapy of an animal model of human gastric cancer using a combination of anti-erbB-2 monoclonal antibodies," Cancer Res (1992) 52(10):2771-2776.
Kohler et al., "Continuous cultures of fused cells secreting antibody of predefined specificity," Nature (1975) 256:495-497.
Kozbor, et al., "The production of monoclonal antibodies from human lymphocytes," Immunol. Today (1983) 4(3):72-79.
Lau et al., "Conjugation of doxorubicin to monoclonal anti-carcinoembryonic antigen antibody via novel thiol-directed cross-linkina reaaents," Bioora Med Chem (1995) 3(10):1299-1304.
Lau et al., "Novel doxorubicin-monoclonal anti-carcinoembryonic antigen antibody immunoconivaate activity in vitro," Bioora Med Chem (1995) 3(10):1305-1312.
Lei et al., "Structure-function analysis of human glucose-6-phosphatase, the enzyme deficient in alvcoaen storaae disease tvoe 1a," J Biol Chem (1995) 270(20):11882-11886.
Liu et al., "Eradication of large colon tumor xenografts by targeted delivery of maytansinoids," Proc Natl Acad Sci USA (1996) 93(16):8618-8623.
Lode et al., "Targeted therapy with a novel enediyene antibiotic calicheamicin effectively suppresses growth and dissemination of liver metastases in a syngeneic model of murine neuroblastoma," Cancer Res (1998) 58:2928.
Mandler et al., "Immunoconjuqates of qeldanamycin and anti-HER2 monoclonal antibodies: antiproliferative activity on human breast carcinoma cell lines," J Natl Cancer Inst (2000) 92(19):1573-1581.
Mandler et al., "Modifications in synthesis strategy improve the yield and efficacy of qeldanamvcin-herceptin immunoconjuqates," Bioconjuq Chem (2002) 13(4):786-791.
Mandler et al., "Synthesis and evaluation of antiproliferative activity of a geldanamycin-Herceptin immunoconiuqate," Bioorq Med Chem Lett (2000) 10(10):1025-1028.
Marks et al., "By-passing immunization Human antibodies from V-gene libraries displayed on phaqe," J. Mol. Biol. (1991) 222(3):581-597.
Morrison et al., "Chimeric human antibody molecules: mouse antigen-binding domains with human constant reaion domains," Proc. Natl. Acad. Sci. USA (1984) 81:6851-6855.
Mosmann, "Rapid colorimetric assay for cellular growth and survivial: application to proliferation and cytotoxicity assays," J Immunol Methods (1983) 65:55-63.
Mount et al., "Chimeric (mouse/human) anti-colon cancer antibody c30.6 inhibits the growth of human colorectal cancer xenografts in scid/scid mice," Cancer Res (1994) 54(23):6160-6166.

Neville et al., "Enhancement of immunotoxin efficacy by acid-cleavable cross-linking agents utilizing diphtheria toxin and toxin mutants," J Biol Chem (1989) 264(25):14653-14661.
Ozaki et al., "Immunotherapy of multiple myeloma with a monoclonal antibody directed against a plasma cell-specific antigen, HM1.24," Blood (1997) 90(8):3179-3186.
Pettit et al., "Specific activities of dolastatin 10 and peptide derivatives against Cryptococcus neoformans," Antimicrob Aqents Chemother (1998) 42(11):2961-2965.
Piazza et al., "Antineoplastic drugs sulindac sulfide and sulfone inhibit cell growth by inducing apoptosis," Cancer Res (1995) 55(14):3110-3116.
Press at el., "Radiolabeled-antibody therapy of B-cell lymphoma with autologous bone marrow support," N Enql J Med (1993) 329(17):1219-1224.
Queen et al., "A humanized antibody that binds to the interleukin 2 receptor," Proc. Nat'l Acad. Sci. USA (1989) 86(24):10029-10033.
Rowland et al., "Drug localization and growth inhibition studies of vindesine-monoclonal anti-CEA conjugates in a human tumour xenograft," Cancer Immunol. Immunother (1986) 21(3):183-87.
Senter et al., "Immunoconjugates comprised of drugs with impaired cellular permeability: A new aooroach to targeted therapy," Proc Amer Assoc Cancer Res (2004) 64:144 abs 623.
Sievers et al., "Selective ablation of acute myeloid leukemia using antibody-targeted chemotherapy: a phase I study of an anti-CD33 calicheamicin immunoconjugate," Blood (1999) 93(11):3678-3684.
Springer et al., "Antibody-directed enzyme prodrug therapy (ADEPT): a review," Adv Drug Deliv Rev (1997) 26(2-3):151-172.
Strome et al., "A mechanistic perspective of monoclonal antibodies in cancer therapy beyond target-related effects", Oncologist, 12(9):1084-1095 (2007).
Syrigos et al., "Antibody directed enzyme prodrug therapy (ADEPT): a review of the experimental and clinical considerations," Anticancer Res (1999) 19(1A):605-614.
Thorpe et al., "New coupling agents for the synthesis of immunotoxins containing a hindered disulfide bond with improved stability in vivo," Cancer Res (1987) 47(22):5924-5931.
Thorpe, "Antibody Carriers of Cytotoxic Agents in Cancer Therapy: A Review," in Monoclonal Antibodies '84: Biological and Clinical APPiications (1985) pp. 475-506.
Tomizuka et al., "Double trans-chromosomic mice: maintenance of two individual human chromosome fragments containing 1q heavy and kappa loci and expression of fully human antibodies," Proc. Natl. Acad. Sci. USA (2000) 97(2):722-727.
Tsunenari et al., "New xenograft model of multiple myeloma and efficacy of a humanized antibody aaainst human interleukin-6 receptor," Blood (1997) 90(6):2437-2444.
Velders et al., "Immunotherapy with low and high affinity monoclonal antibodies 17-1A and 323/A3 in a nude mouse xenoaraft carcinoma model," Cancer Res (1995) 55(19):4398-4403.
Wiseman et al., "Ibritumomab tiuxetan radioimmunotherapy for patients with relapsed or refractory non-Hodgkin lymphoma and mild thrombocytopenia: a phase II multicenter trial," Blood (2002) 99(12):4336-4342.
Wolff et al., "Monoclonal antibody homodimers: enhanced antitumor activity in nude mice," Cancer Res (1993) 53(11):2560-2565.
Woyke et al., "In vitro activities and postantifungal effects of the potent dolastatin 10 derivative auristatin PHE," Antimicrob Agents Chemother (2001) 45(12):3580-3584.
Yu et al., "The biosynthetic gene cluster of the maytansinoid antitumor agent ansamitocin from actmosynnema pretiosum," Proc Natl Acad Sci U.S.A. (2002) 99(12):7968-7973.
Zhao et al., "Targeting CD37-positive lymphoid malignancies with a novel engineered small modular immunopharmaceutical," Blood (2007) 110(7):2569-2577.

\* cited by examiner

Figure 1. The cDNA (SEQ ID NO: 1) and amino acid sequence (SEQ ID NO: 2) of human CD37. The start methionine is underlined. The open reading frame extends from nucleic acid 122-967 including the stop codon.

```
  1 TTCTTTCTCTCTCAGCTCTCCGTCTCTCTTTCTCTCTCAGCCTCTTTCTTTCTCCCTGT
 61 CTCCCCACTGTCAGCACCTCTTCTGTGTGGTGAGTGGACCGCTTACCCACTAGGTGAA
         M  S  A  Q  E  S  C  L  S  L  I  K  Y  F  L  F  V  F  N  L
121 GATGTCAGCCCAGGAGAGCTGCCTCAGCCTCATCAAGTACTTCCTCTTCGTTTTCAACCT
       F  F  F  V  L  G  S  L  I  F  C  F  G  I  W  I  L  I  D  K
181 CTTCTTCTTCGTCCTCGGCAGCCTGATCTTCTGCTTCGGCATCTGGATCCTCATTGACAA
       T  S  F  V  S  F  V  G  L  A  F  V  P  L  Q  I  W  S  K  V
241 GACCAGCTTCGTGTCCTTTGTGGGCTTGGCCTTCGTGCCTCTGCAGATCTGGTCCAAAGT
       L  A  I  S  G  I  F  T  M  G  I  A  L  L  G  C  V  G  A  L
301 CCTGGCCATCTCAGGAATCTTCACCATGGGCATCGCCCTCCTGGGTGTGTGGGGGCCCT
       K  E  L  R  C  L  L  G  L  Y  F  G  M  L  L  L  F  A  T
361 CAAGGAGCTCCGCTGCCTCCTGGGCCTGTATTTTGGGATGCTGCTGCTCCTGTTTGCCAC
       Q  I  T  L  G  I  L  I  S  T  Q  R  A  Q  L  E  R  S  L  R
421 ACAGATCACCCTGGGAATCCTCATCTCCACTCAGCGGGCCCAGCTGGAGCGAAGCTTGCG
       D  V  V  E  K  T  I  Q  K  Y  G  T  N  P  E  E  T  A  A  E
481 GGACGTCGTAGAGAAAACCATCCAAAAGTACGGCACCAACCCCGAGGAGACCGCGGCCGA
       E  S  W  D  Y  V  Q  F  Q  L  R  C  C  G  W  H  Y  P  Q  D
541 GGAGAGCTGGGACTATGTGCAGTTCCAGCTGCGCTGCTGCGGCTGGCACTACCCGCAGGA
       W  F  Q  V  L  I  L  R  G  N  S  E  A  H  R  V  P  C  S
601 CTGGTTCCAAGTCCTCATCCTGAGAGGTAACGGGTCGGAGGCGCACCGCGTGCCCTGCTC
       C  Y  N  L  S  A  T  N  D  S  T  I  L  D  K  V  I  L  P  Q
661 CTGCTACAACTTGTCGGCGACCAACGACTCCACAATCCTAGATAAGGTGATCTTGCCCCA
       L  S  R  L  G  H  L  A  R  S  R  H  S  A  D  I  C  A  V  P
721 GCTCAGCAGGCTTGGACACCTGGCGCGGTCCAGACACAGTGCAGACATCTGCGCTGTCCC
       A  E  S  H  I  Y  R  E  G  C  A  Q  G  L  Q  K  W  L  H  N
781 TGCAGAGAGCCACATCTACCGCGAGGGCTGCGCGCAGGGCCTCCAGAAGTGGCTGCACAA
       N  L  I  S  I  V  G  I  C  L  G  V  G  L  L  E  L  G  F  M
841 CAACCTTATTTCCATAGTGGGCATTTGCCTGGGCGTCGGCCTACTCGAGCTCGGGTTCAT
       T  L  S  I  F  L  C  R  N  L  D  H  V  Y  N  R  L  A  R  Y
901 GACGCTCTCGATATTCCTGTGCAGAAACCTGGACCACGTCTACAACCGGCTCGCTCGATA
```

Figure 1 (continued)
```
         · R   *
 961  CCGTTAGGCCCCGCCCTCCCCAAAGTCCCGCCCCGCCCCCGTCACGTGCGCTGGGCACTT
1021  CCCTGCTGCCTGTAAATATTTGTTTAATCCCCAGTTCGCCTGGAGCCCTCCGCCTTCACA
1081  TTCCCTGGGGACCCACGTGGCTGCGTGCCCTGCTGCTGTCACCTCTCCCACGGGACCT
1141  GGGGCTTTCGTCCACAGCTTCCTGTCCCATCTGTCGGCCTACCACCACCCACAAGATTA
1201  TTTTTCACCCAAACCTCAAATAAATCCCTGCGTTTTTGGTAAAAAAAAAAAAAAAAAAA
1261  AAA
```

Figure 2A  The cDNA (SEQ ID NO : 3) and amino acid sequence (SEQ ID NO: 4) of HvCD37-6b15.1.1 heavy chain. Double-underlined is the heavy chain variable region, and underlined is the heavy chain human IgG2 constant region.

```
        Q  V  Q  L  Q  Q  W  G  A  G  L  L  K  P  S  E  T  L  S  L
   1    CAGGTGCAGCTACAGCAGTGGGGCGCAGGACTGTTGAAGCCTTCGGAGACCCTGTCCCTC
        T  C  A  V  Y  G  G  S  F  S  P  Y  Y  W  S  W  I  R  Q  P
  61    ACTTGCGCTGTCTATGGTGGGTCCTTCAGTCCTTACTACTGGAGCTGGATCCGCCAGCCC
        P  G  K  G  L  E  W  I  G  E  I  N  H  S  G  S  T  N  Y  N
 121    CCAGGGAAGGGGTTGGAGTGGATTGGGGAAATCAATCATAGTGGAAGCACCAACTACAAC
        P  S  L  K  S  R  V  T  I  S  V  D  T  S  K  N  Q  F  S  L
 181    CCGTCCCTCAAGAGTCGAGTCACCATTTCAGTAGACACGTCCAAGAACCAGTTCTCCCTG
        K  L  S  S  V  T  A  A  D  T  A  V  Y  Y  C  A  R  R  A  G
 241    AAGCTGAGCTCTGTGACCGCCGCGGACACGGCTGTCTATTACTGTGCGAGGAGAGCTGGG
        D  F  D  Y  W  G  Q  G  T  L  V  T  V  S  S  A  S  T  K  G
 301    GACTTTGACTACTGGGGCCAGGGAACCCTGGTCACCGTCTCCTCAGCATCCACCAAGGGC
        P  S  V  F  P  L  A  P  C  S  R  S  T  S  E  S  T  A  A  L
 361    CCATCGGTCTTCCCCCTGGCGCCCTGCTCCAGGAGCACCTCCGAGAGCACAGCGGCCCTG
        G  C  L  V  K  D  Y  F  P  E  P  V  T  V  S  W  N  S  G  A
 421    GGCTGCCTGGTCAAGGACTACTTCCCCGAACCGGTGACGGTGTCGTGGAACTCAGGCGCT
        L  T  S  G  V  H  T  F  P  A  V  L  Q  S  S  G  L  Y  S  L
 481    CTGACCAGCGGCGTGCACACCTTCCCAGCTGTCCTACAGTCCTCAGGACTCTACTCCCTC
        S  S  V  V  T  V  P  S  S  N  F  G  T  Q  T  Y  T  C  N  V
 541    AGCAGCGTGGTGACCGTGCCCTCCAGCAACTTCGGCACCCAGACCTACACCTGCAACGTA
        D  H  K  P  S  N  T  K  V  D  K  T  V  E  R  K  C  C  V  E
 601    GATCACAAGCCCAGCAACACCAAGGTGGACAAGACAGTTGAGCGCAAATGTTGTGTCGAG
        C  P  P  C  P  A  P  P  V  A  G  P  S  V  F  L  F  P  P  K
 661    TGCCCACCGTGCCCAGCACCACCTGTGGCAGGACCGTCAGTCTTCCTCTTCCCCCCAAAA
        P  K  D  T  L  M  I  S  R  T  P  E  V  T  C  V  V  V  D  V
 721    CCCAAGGACACCCTCATGATCTCCCGGACCCCTGAGGTCACGTGCGTGGTGGTGGACGTG
        S  H  E  D  P  E  V  Q  F  N  W  Y  V  D  G  V  E  V  H  N
 781    AGCCACGAAGACCCCGAGGTCCAGTTCAACTGGTACGTGGACGGCGTGGAGGTGCATAAT
        A  K  T  K  P  R  E  E  Q  F  N  S  T  F  R  V  V  S  V  L
 841    GCCAAGACAAAGCCACGGGAGGAGCAGTTCAACAGCACGTTCCGTGTGGTCAGCGTCCTC
        T  V  V  H  Q  D  W  L  N  G  K  E  Y  K  C  K  V  S  N  K
 901    ACCGTTGTGCACCAGGACTGGCTGAACGGCAAGGAGTACAAGTGCAAGGTCTCCAACAAA
        G  L  P  A  P  I  E  K  T  I  S  K  T  K  G  Q  P  R  E  P
 961    GGCCTCCCAGCCCCCATCGAGAAAACCATCTCCAAAACCAAAGGGCAGCCCCGAGAACCA
        Q  V  Y  T  L  P  P  S  R  E  E  M  T  K  N  Q  V  S  L  T
1021    CAGGTGTACACCCTGCCCCCATCCCGGGAGGAGATGACCAAGAACCAGGTCAGCCTGACC
        C  L  V  K  G  F  Y  P  S  D  I  A  V  E  W  E  S  N  G  Q
1081    TGCCTGGTCAAAGGCTTCTACCCCAGCGACATCGCCGTGGAGTGGGAGAGCAATGGGCAG
        P  E  N  N  Y  K  T  T  P  P  M  L  D  S  D  G  S  F  F  L
1141    CCGGAGAACAACTACAAGACCACACCTCCCATGCTGGACTCCGACGGCTCCTTCTTCCTC
        Y  S  K  L  T  V  D  K  S  R  W  Q  Q  G  N  V  F  S  C  S
1201    TACAGCAAGCTCACCGTGGACAAGAGCAGGTGGCAGCAGGGGAACGTCTTCTCATGCTCC
        V  M  H  E  A  L  H  N  H  Y  T  Q  K  S  L  S  L  S  P  G
1261    GTGATGCATGAGGCTCTGCACAACCACTACACGCAGAAGAGCCTCTCCCTGTCTCCGGGT
        K  *
1321    AAATAA
```

Figure 2B The cDNA (SEQ ID NO : 5) and amino acid sequence (SEQ ID NO: 6) of HvCD37-6b15.1.1 light chain. Double-underlined is the light chain variable region, and underlined is the human kappa constant region.

```
        D   I   Q   M   T   Q   S   P   S   T   L   S   A   S   V   G   D   R   V   T
  1   GACATCCAGATGACCCAGTCTCCTTCCACCCTGTCTGCATCTGTTGGAGACAGAGTCACC
        I   T   C   R   A   S   Q   S   I   S   S   W   L   A   W   Y   Q   Q   K   P
 61   ATCACTTGCCGGGCCAGTCAGAGTATTAGTAGCTGGTTGGCCTGGTATCAGCAGAAACCA
        G   K   A   P   K   L   L   I   Y   K   A   S   S   L   E   S   G   V   P   S
121   GGGAAAGCCCCTAAGCTCCTGATCTATAAGGCGTCTAGTTTAGAAAGTGGGGTCCCATCA
        R   F   S   G   S   G   S   G   T   E   F   T   L   T   I   S   S   L   Q   P
181   AGGTTTAGCGGCAGTGGATCTGGGACAGAATTCACTCTCACCATCAGCAGCCTGCAGCCT
        D   D   F   A   T   Y   Y   C   Q   Q   Y   N   S   Y   I   F   G   Q   G   T
241   GATGATTTTGCAACTTATTACTGCCAACAGTATAATAGTTACATTTTTGGCCAGGGGACC
        K   L   E   I   K   R   T   V   A   A   P   S   V   F   I   F   P   P   S   D
301   AAGCTGGAGATCAAACGGACTGTGGCTGCACCATCTGTCTTCATCTTCCCGCCATCTGAT
        E   Q   L   K   S   G   T   A   S   V   V   C   L   L   N   N   F   Y   P   R
361   GAGCAGTTGAAATCTGGAACTGCCTCTGTTGTGTGCCTGCTGAATAACTTCTATCCCAGA
        E   A   K   V   Q   W   K   V   D   N   A   L   Q   S   G   N   S   Q   E   S
421   GAGGCCAAAGTACAGTGGAAGGTGGATAACGCCCTCCAATCGGGTAACTCCCAGGAGAGT
        V   T   E   Q   D   S   K   D   S   T   Y   S   L   S   S   T   L   T   L   S
481   GTCACAGAGCAGGACAGCAAGGACAGCACCTACAGCCTCAGCAGCACCCTGACGCTGAGC
        K   A   D   Y   E   K   H   K   V   Y   A   C   E   V   T   H   Q   G   L   S
541   AAAGCAGACTACGAGAAACACAAAGTCTACGCCTGCGAAGTCACCCATCAGGGCCTGAGC
        S   P   V   T   K   S   F   N   R   G   E   C   *
601   TCGCCCGTCACAAAGAGCTTCAACAGGGGAGAGTGTTAG
```

Figure 3A The amino acid sequence (SEQ ID NO: 7) of HvCD37-6b15.1.1 heavy chain. Double-underlined is the heavy chain variable region, and underlined is the human IgG2 constant region.

```
  1  QVQLQQWGAGLLKPSETLSLTCAVYGGSFSPYYWSWIRQPPGKGLEWIGE
 51  INHSGSTNYNPSLKSRVTISVDTSKNQFSLKLSSVTAADTAVYYCARRAG
101  DFDYWGQGTLVTVSSASTKGPSVFPLAPCSRSTSESTAALGCLVKDYFPE
151  PVTVSWNSGALTSGVHTFPAVLQSSGLYSLSSVVTVPSSNFGTQTYTCNV
201  DHKPSNTKVDKTVERKCCVECPPCPAPPVAGPSVFLFPPKPKDTLMISRT
251  PEVTCVVVDVSHEDPEVQFNWYVDGVEVHNAKTKPREEQFNSTFRVVSVL
301  TVVHQDWLNGKEYKCKVSNKGLPAPIEKTISKTKGQPREPQVYTLPPSRE
351  EMTKNQVSLTCLVKGFYPSDIAVEWESNGQPENNYKTTPPMLDSDGSFFL
401  YSKLTVDKSRWQQGNVFSCSVMHEALHNHYTQKSLSLSPGK
```

Figure 3B The amino acid sequence (SEQ ID NO: 8) of HvCD37-6b15.1.1 light chain. Double-underlined is the light chain variable region, and underlined is the human kappa constant region.

```
  1    DIQMTQSPSTLSASVGDRVTITCRASQSISSWLAWYQQKPGKAPKLLIYK
 51    ASSLESGVPSRFSGSGSGTEFTLTISSLQPDDFATYYCQQYNSYIFGQGT
101    KLEIKRTVAAPSVFIFPPSDEQLKSGTASVVCLLNNFYPREAKVQWKVDN
151    ALQSGNSQESVTEQDSKDSTYSLSSTLTLSKADYEKHKVYACEVTHQGLS
201    SPVTKSFNRGEC
```

Figure 4A: Alignment of HvCD37-6b15.1.1 heavy chain to human Ig germline.

Figure 4B: Alignment of HvCD37-6b15.1.1 light chain to human Ig germline.

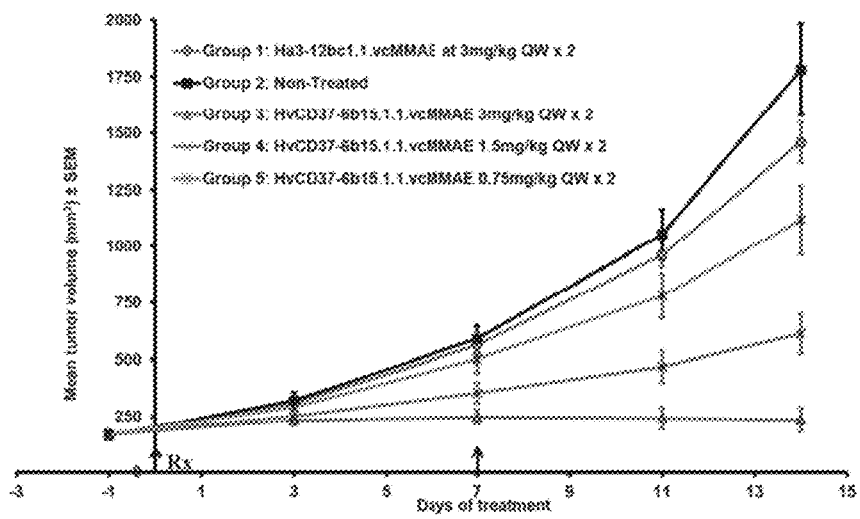
Figure 5. Efficacy study of HvCD37-6b15.1.1.vcMMAE in subcutaneously established human follicular B cell lymphoma DoHH2 implanted in CB17/SCID mice.
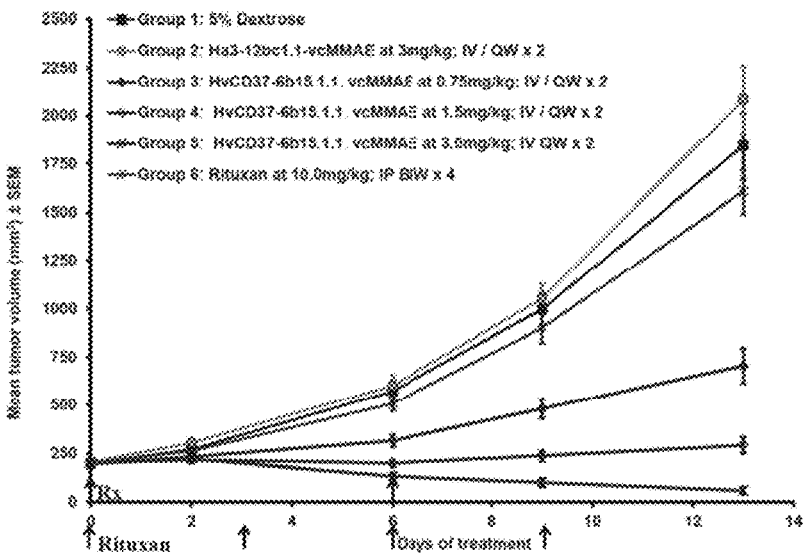
Figure 6. Efficacy Study of HvCD37-6b15.1.1.vcMMAE in Subcutaneously Established Xenograft Model of Human Lymphoma Ramos-RR-KCL Implanted in CB17/SCID Mice.

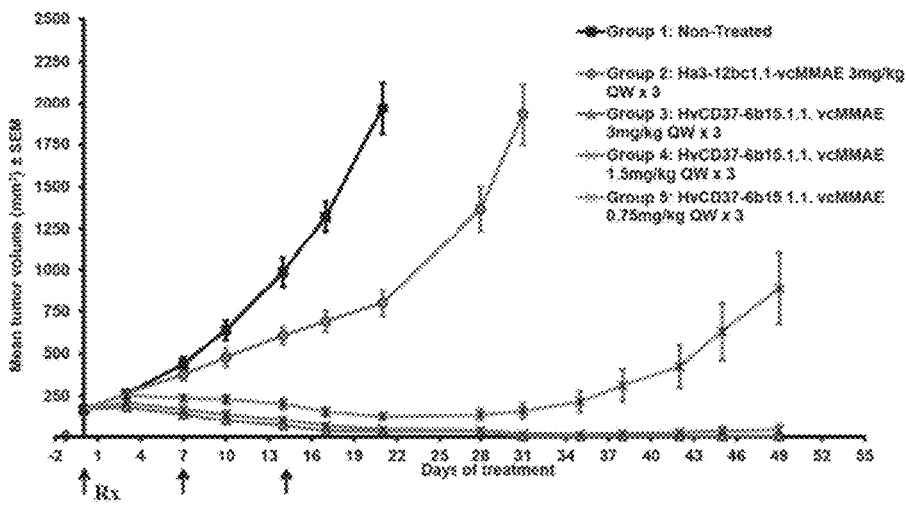
Figure 7. Efficacy study of HvCD37-6b15.1.1.vcMMAE in subcutaneously established human *chronic lymphocytic leukemia JVM3* implanted in CB17/SCID mice.
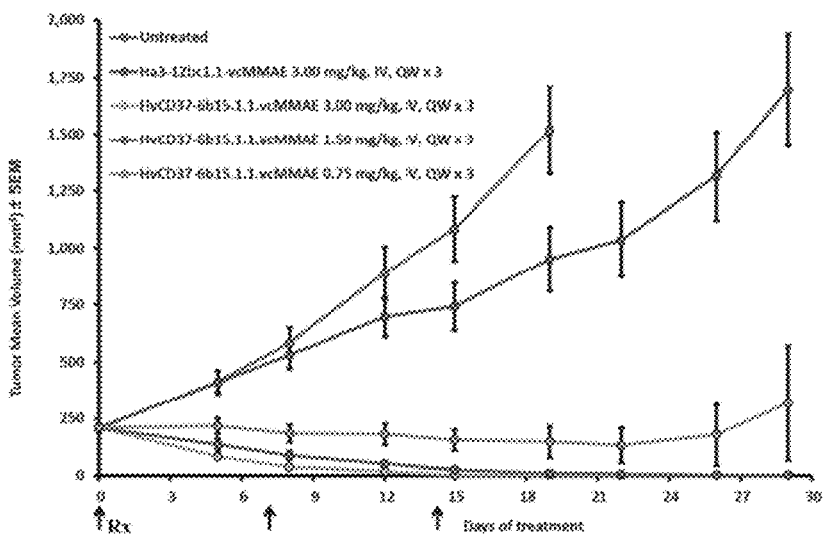
Figure 8. Efficacy study of HvCD37-6b15.1.1.vcMMAE in subcutaneously established human *Acute Myelogenous Leukemia MV-4-11* implanted in CB17/SCID mice.

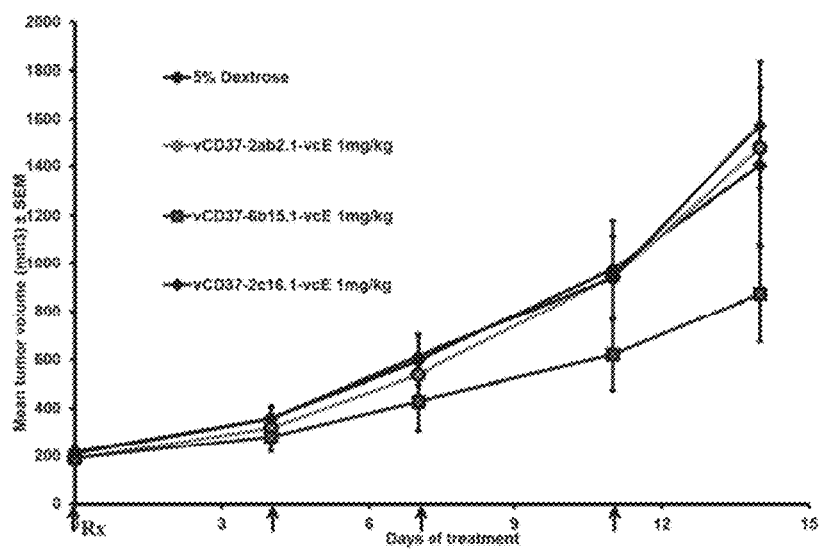

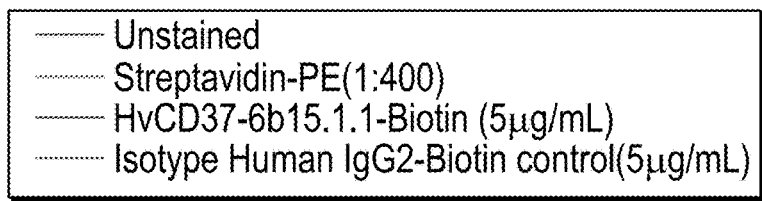
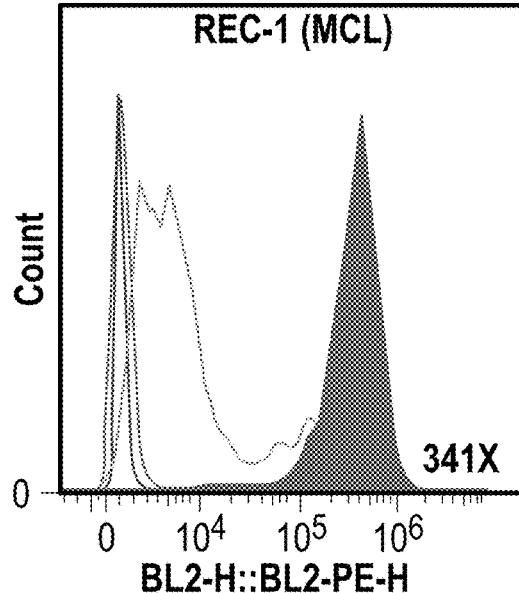
FIG. 12D
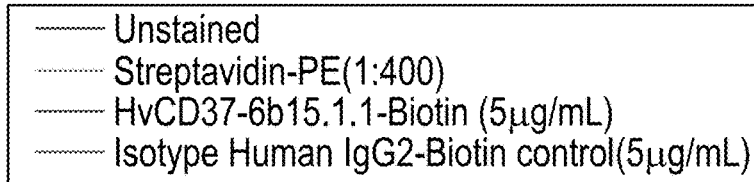
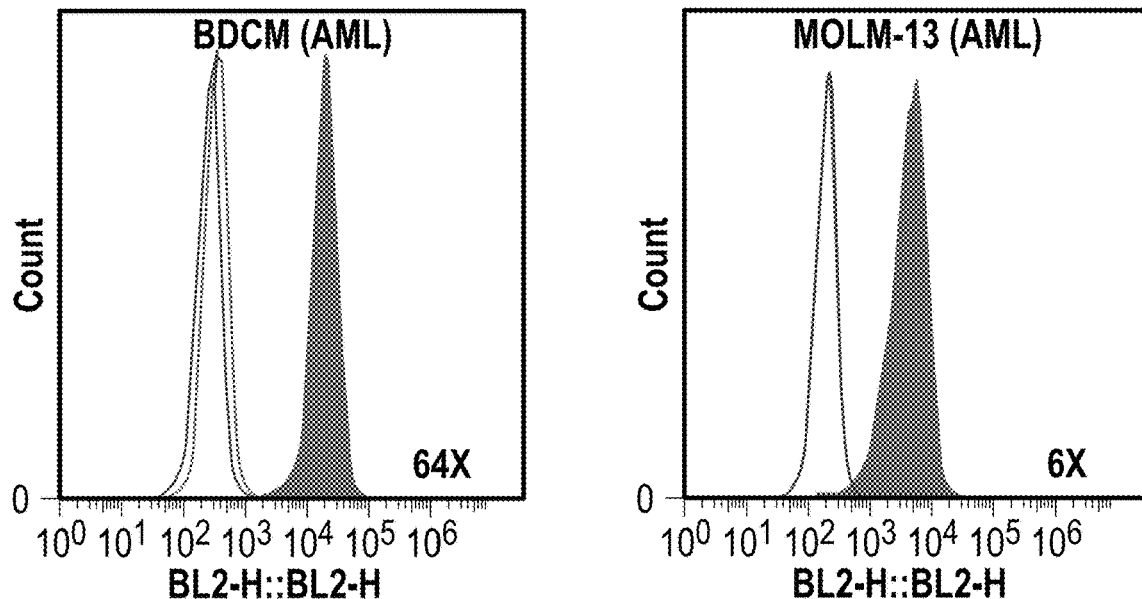
FIG. 13A

SEQUENCE LISTING

<160> NUMBER OF SEQ ID NOS: 13

<210> SEQ ID NO 1
<211> LENGTH: 1263
<212> TYPE: DNA
<213> ORGANISM: Homo sapiens
<220> FEATURE:
<221> NAME/KEY: CDS
<222> LOCATION: (122)...(967)

<400> SEQUENCE: 1

```
ttcctttctc tctcagctct ccgtctctct ttctctctca gcctctttct ttctccctgt      60
ctcccccact gtcagcacct cttctgtgtg gtgagtggac cgcttacccc actaggtgaa     120 g atg tca gcc cag gag agc tgc ctc agc ctc atc aag tac ttc ctc ttc    169
  Met Ser Ala Gln Glu Ser Cys Leu Ser Leu Ile Lys Tyr Phe Leu Phe
  1               5                  10                  15 gtt ttc aac ctc ttc ttc ttc gtc ctc ggc agc ctg atc ttc tgc ttc       217
Val Phe Asn Leu Phe Phe Phe Val Leu Gly Ser Leu Ile Phe Cys Phe
                20                  25                  30 ggc atc tgg atc ctc att gac aag acc agc ttc gtg tcc ttt gtg ggc       265
Gly Ile Trp Ile Leu Ile Asp Lys Thr Ser Phe Val Ser Phe Val Gly
            35                  40                  45 ttg gcc ttc gtg cct ctg cag atc tgg tcc aaa gtc ctg gcc atc tca       313
Leu Ala Phe Val Pro Leu Gln Ile Trp Ser Lys Val Leu Ala Ile Ser
        50                  55                  60 gga atc ttc acc atg ggc atc gcc ctc ctg ggt tgt gtg ggg gcc ctc       361
Gly Ile Phe Thr Met Gly Ile Ala Leu Leu Gly Cys Val Gly Ala Leu
65                  70                  75                  80 aag gag ctc cgc tgc ctc ctg ggc ctg tat ttt ggg atg ctg ctg ctc       409
Lys Glu Leu Arg Cys Leu Leu Gly Leu Tyr Phe Gly Met Leu Leu Leu
                85                  90                  95 ctg ttt gcc aca cag atc acc ctg gga atc ctc atc tcc act cag cgg       457
```

```
        Leu Phe Ala Thr Gln Ile Thr Leu Gly Ile Leu Ile Ser Thr Gln Arg
                        100                 105                 110 gcc cag ctg gag cga agc ttg cgg gac gtc gta gag aaa acc atc caa       505
Ala Gln Leu Glu Arg Ser Leu Arg Asp Val Val Glu Lys Thr Ile Gln
                115                 120                 125 aag tac ggc acc aac ccc gag gag acc gcg gcc gag gag agc tgg gac       553
Lys Tyr Gly Thr Asn Pro Glu Glu Thr Ala Ala Glu Glu Ser Trp Asp
130                 135                 140 tat gtg cag ttc cag ctg cgc tgc tgc ggc tgg cac tac ccg cag gac       601
Tyr Val Gln Phe Gln Leu Arg Cys Cys Gly Trp His Tyr Pro Gln Asp
145                 150                 155                 160 tgg ttc caa gtc ctc atc ctg aga ggt aac ggg tcg gag gcg cac cgc       649
Trp Phe Gln Val Leu Ile Leu Arg Gly Asn Gly Ser Glu Ala His Arg
                165                 170                 175 gtg ccc tgc tcc tgc tac aac ttg tcg gcg acc aac gac tcc aca atc       697
Val Pro Cys Ser Cys Tyr Asn Leu Ser Ala Thr Asn Asp Ser Thr Ile
            180                 185                 190 cta gat aag gtg atc ttg ccc cag ctc agc agg ctt gga cac ctg gcg       745
Leu Asp Lys Val Ile Leu Pro Gln Leu Ser Arg Leu Gly His Leu Ala
        195                 200                 205 cgg tcc aga cac agt gca gac atc tgc gct gtc cct gca gag agc cac       793
Arg Ser Arg His Ser Ala Asp Ile Cys Ala Val Pro Ala Glu Ser His
210                 215                 220 atc tac cgc gag ggc tgc gcg cag ggc ctc cag aag tgg ctg cac aac       841
Ile Tyr Arg Glu Gly Cys Ala Gln Gly Leu Gln Lys Trp Leu His Asn
225                 230                 235                 240 aac ctt att tcc ata gtg ggc att tgc ctg ggc gtc ggc cta ctc gag       889
Asn Leu Ile Ser Ile Val Gly Ile Cys Leu Gly Val Gly Leu Leu Glu
                245                 250                 255 ctc ggg ttc atg acg ctc tcg ata ttc ctg tgc aga aac ctg gac cac       937
Leu Gly Phe Met Thr Leu Ser Ile Phe Leu Cys Arg Asn Leu Asp His
            260                 265                 270 gtc tac aac cgg ctc gct cga tac cgt tag gccccgccct ccccaaagtc         987
Val Tyr Asn Arg Leu Ala Arg Tyr Arg
        275                 280 ccgccccgcc ccgtcacgt gcgctgggca cttccctgct gcctgtaaat atttgtttaa      1047
tccccagttc gcctggagcc ctccgccttc acattcccct ggggaccac gtggctgcgt      1107 gcccctgctg ctgtcacctc tcccacggga cctggggctt tcgtccacag cttcctgtcc    1167
ccatctgtcg gcctaccacc acccacaaga ttattttttca cccaaacctc aaataaatcc   1227
cctgcgtttt tggtaaaaaa aaaaaaaaaa aaaaaa                              1263

<210> SEQ ID NO 2
<211> LENGTH: 281
<212> TYPE: PRT
<213> ORGANISM: Homo sapiens

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
                20                  25                  30

Gly Ile Trp Ile Leu Ile Asp Lys Thr Ser Phe Val Ser Phe Val Gly
            35                  40                  45

Leu Ala Phe Val Pro Leu Gln Ile Trp Ser Lys Val Leu Ala Ile Ser
        50                  55                  60

Gly Ile Phe Thr Met Gly Ile Ala Leu Leu Gly Cys Val Gly Ala Leu
65                  70                  75                  80
```

-continued

```
Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 3
<211> LENGTH: 1326
<212> TYPE: DNA
<213> ORGANISM: Homo sapiens
<220> FEATURE:
<221> NAME/KEY: CDS
<222> LOCATION: (1)...(1326)
<220> FEATURE:
<221> NAME/KEY: misc_feature
<222> LOCATION: (1)...(1326)
<223> OTHER INFORMATION: HvCD37-6b15.1.1 heavy chain
<220> FEATURE:
<221> NAME/KEY: misc_feature
<222> LOCATION: (1)...(345)
<223> OTHER INFORMATION: heavy chain variable region
<220> FEATURE:
<221> NAME/KEY: misc_feature
<222> LOCATION: (346)...(1326)
<223> OTHER INFORMATION: heavy chain human IgG2 constant region

<400> SEQUENCE: 3 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
  1               5                  10                  15 acc ctg tcc ctc acc tgc gct gtc tat ggt ggg tcc ttc agt cct tac      96
Thr Leu Ser Leu Thr Cys Ala Val Tyr Gly Gly Ser Phe Ser Pro Tyr
                20                  25                  30 tac tgg agc tgg atc cgc cag ccc cca ggg aag ggg ttg gag tgg att     144
Tyr Trp Ser Trp Ile Arg Gln Pro Pro Gly Lys Gly Leu Glu Trp Ile
            35                  40                  45 ggg gaa atc aat cat agt gga agc acc aac tac aac ccg tcc ctc aag     192
Gly Glu Ile Asn His Ser Gly Ser Thr Asn Tyr Asn Pro Ser Leu Lys
        50                  55                  60
```

```
agt cga gtc acc att tca gta gac acg tcc aag aac cag ttc tcc ctg      240
Ser Arg Val Thr Ile Ser Val Asp Thr Ser Lys Asn Gln Phe Ser Leu
 65              70                  75                  80 aag ctg agc tct gtg acc gcc gcg gac acg gct gtc tat tac tgt gcg      288
Lys Leu Ser Ser Val Thr Ala Ala Asp Thr Ala Val Tyr Tyr Cys Ala
             85                  90                  95 agg aga gct ggg gac ttt gac tac tgg ggc cag gga acc ctg gtc acc      336
Arg Arg Ala Gly Asp Phe Asp Tyr Trp Gly Gln Gly Thr Leu Val Thr
            100                 105                 110 gtc tcc tca gca tcc acc aag ggc cca tcg gtc ttc ccc ctg gcg ccc      384
Val Ser Ser Ala Ser Thr Lys Gly Pro Ser Val Phe Pro Leu Ala Pro
        115                 120                 125 tgc tcc agg agc acc tcc gag agc aca gcg gcc ctg ggc tgc ctg gtc      432
Cys Ser Arg Ser Thr Ser Glu Ser Thr Ala Ala Leu Gly Cys Leu Val
        130                 135                 140 aag gac tac ttc ccc gaa ccg gtg acg gtg tcg tgg aac tca ggc gct      480
Lys Asp Tyr Phe Pro Glu Pro Val Thr Val Ser Trp Asn Ser Gly Ala
145                 150                 155                 160 ctg acc agc ggc gtg cac acc ttc cca gct gtc cta cag tcc tca gga      528
Leu Thr Ser Gly Val His Thr Phe Pro Ala Val Leu Gln Ser Ser Gly
                165                 170                 175 ctc tac tcc ctc agc agc gtg gtg acc gtg ccc tcc agc aac ttc ggc      576
Leu Tyr Ser Leu Ser Ser Val Val Thr Val Pro Ser Ser Asn Phe Gly
            180                 185                 190 acc cag acc tac acc tgc aac gta gat cac aag ccc agc aac acc aag      624
Thr Gln Thr Tyr Thr Cys Asn Val Asp His Lys Pro Ser Asn Thr Lys
        195                 200                 205 gtg gac aag aca gtt gag cgc aaa tgt tgt gtc gag tgc cca ccg tgc      672
Val Asp Lys Thr Val Glu Arg Lys Cys Cys Val Glu Cys Pro Pro Cys
210                 215                 220 cca gca cca cct gtg gca gga ccg tca gtc ttc ctc ttc ccc cca aaa      720
Pro Ala Pro Pro Val Ala Gly Pro Ser Val Phe Leu Phe Pro Pro Lys
225                 230                 235                 240 ccc aag gac acc ctc atg atc tcc cgg acc cct gag gtc acg tgc gtg      768
Pro Lys Asp Thr Leu Met Ile Ser Arg Thr Pro Glu Val Thr Cys Val
                245                 250                 255 gtg gtg gac gtg agc cac gaa gac ccc gag gtc cag ttc aac tgg tac      816
Val Val Asp Val Ser His Glu Asp Pro Glu Val Gln Phe Asn Trp Tyr
            260                 265                 270 gtg gac ggc gtg gag gtg cat aat gcc aag aca aag cca cgg gag gag      864
Val Asp Gly Val Glu Val His Asn Ala Lys Thr Lys Pro Arg Glu Glu
        275                 280                 285 cag ttc aac agc acg ttc cgt gtg gtc agc gtc ctc acc gtt gtg cac      912
Gln Phe Asn Ser Thr Phe Arg Val Val Ser Val Leu Thr Val Val His
290                 295                 300 cag gac tgg ctg aac ggc aag gag tac aag tgc aag gtc tcc aac aaa      960
Gln Asp Trp Leu Asn Gly Lys Glu Tyr Lys Cys Lys Val Ser Asn Lys
305                 310                 315                 320 ggc ctc cca gcc ccc atc gag aaa acc atc tcc aaa acc aaa ggg cag     1008
Gly Leu Pro Ala Pro Ile Glu Lys Thr Ile Ser Lys Thr Lys Gly Gln
                325                 330                 335 ccc cga gaa cca cag gtg tac acc ctg ccc cca tcc cgg gag gag atg     1056
Pro Arg Glu Pro Gln Val Tyr Thr Leu Pro Pro Ser Arg Glu Glu Met
            340                 345                 350 acc aag aac cag gtc agc ctg acc tgc ctg gtc aaa ggc ttc tac ccc     1104
Thr Lys Asn Gln Val Ser Leu Thr Cys Leu Val Lys Gly Phe Tyr Pro
        355                 360                 365 agc gac atc gcc gtg gag tgg gag agc aat ggg cag ccg gag aac aac     1152
Ser Asp Ile Ala Val Glu Trp Glu Ser Asn Gly Gln Pro Glu Asn Asn
370                 375                 380
```

```
tac aag acc aca cct ccc atg ctg gac tcc gac ggc tcc ttc ttc ctc        1200
Tyr Lys Thr Thr Pro Pro Met Leu Asp Ser Asp Gly Ser Phe Phe Leu
385             390                 395                 400 tac agc aag ctc acc gtg gac aag agc agg tgg cag cag ggg aac gtc        1248
Tyr Ser Lys Leu Thr Val Asp Lys Ser Arg Trp Gln Gln Gly Asn Val
                405                 410                 415 ttc tca tgc tcc gtg atg cat gag gct ctg cac aac cac tac acg cag        1296
Phe Ser Cys Ser Val Met His Glu Ala Leu His Asn His Tyr Thr Gln
            420                 425                 430 aag agc ctc tcc ctg tct ccg ggt aaa taa                                1326
Lys Ser Leu Ser Leu Ser Pro Gly Lys
        435                 440
```

<210> SEQ ID NO 4
<211> LENGTH: 441
<212> TYPE: PRT
<213> ORGANISM: Homo sapiens

<400> SEQUENCE: 4

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Pro Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Gly Asp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285
```

```
Gln Phe Asn Ser Thr Phe Arg Val Val Ser Val Leu Thr Val Val His
    290                 295                 300
Gln Asp Trp Leu Asn Gly Lys Glu Tyr Lys Cys Lys Val Ser Asn Lys
305                 310                 315                 320
Gly Leu Pro Ala Pro Ile Glu Lys Thr Ile Ser Lys Thr Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
370                 375                 380
Tyr Lys Thr Thr Pro Pro Met Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys
        435                 440

<210> SEQ ID NO 5
<211> LENGTH: 639
<212> TYPE: DNA
<213> ORGANISM: Homo sapiens
<220> FEATURE:
<221> NAME/KEY: CDS
<222> LOCATION: (1)...(639)
<220> FEATURE:
<221> NAME/KEY: misc_feature
<222> LOCATION: (1)...(639)
<223> OTHER INFORMATION: HvCD37-6b15.1.1 light chain
<220> FEATURE:
<221> NAME/KEY: misc_feature
<222> LOCATION: (1)...(318)
<223> OTHER INFORMATION: light chain variable region
<220> FEATURE:
<221> NAME/KEY: misc_feature
<222> LOCATION: (319)...(639)
<223> OTHER INFORMATION: human kappa constant region

<400> SEQUENCE: 5 gac atc cag atg acc cag tct cct tcc acc ctg tct gca tct gtt gga      48
Asp Ile Gln Met Thr Gln Ser Pro Ser Thr Leu Ser Ala Ser Val Gly
  1               5                  10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
                 20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
             35                  40                  45 tat aag gcg tct agt tta gaa agt ggg gtc cca tca agg ttt agc ggc     192
Tyr Lys Ala Ser Ser Leu Glu Ser Gly Val Pro Ser Arg Phe Ser Gly
         50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
 65                  70                  75                  80 gat gat ttt gca act tat tac tgc caa cag tat aat agt tac att ttt     288
Asp Asp Phe Ala Thr Tyr Tyr Cys Gln Gln Tyr Asn Ser Tyr Ile Phe
                 85                  90                  95 ggc cag ggg acc aag ctg gag atc aaa cgg act gtg gct gca cca tct     336
Gly Gln Gly Thr Lys Leu Glu Ile Lys Arg Thr Val Ala Ala Pro Ser
```

```
gtc ttc atc ttc ccg cca tct gat gag cag ttg aaa tct gga act gcc    384
Val Phe Ile Phe Pro Pro Ser Asp Glu Gln Leu Lys Ser Gly Thr Ala
        115                 120                 125 tct gtt gtg tgc ctg ctg aat aac ttc tat ccc aga gag gcc aaa gta    432
Ser Val Val Cys Leu Leu Asn Asn Phe Tyr Pro Arg Glu Ala Lys Val
130                 135                 140 cag tgg aag gtg gat aac gcc ctc caa tcg ggt aac tcc cag gag agt    480
Gln Trp Lys Val Asp Asn Ala Leu Gln Ser Gly Asn Ser Gln Glu Ser
145                 150                 155                 160 gtc aca gag cag gac agc aag gac agc acc tac agc ctc agc agc acc    528
Val Thr Glu Gln Asp Ser Lys Asp Ser Thr Tyr Ser Leu Ser Ser Thr
                165                 170                 175 ctg acg ctg agc aaa gca gac tac gag aaa cac aaa gtc tac gcc tgc    576
Leu Thr Leu Ser Lys Ala Asp Tyr Glu Lys His Lys Val Tyr Ala Cys
        180                 185                 190 gaa gtc acc cat cag ggc ctg agc tcg ccc gtc aca aag agc ttc aac    624
Glu Val Thr His Gln Gly Leu Ser Ser Pro Val Thr Lys Ser Phe Asn
            195                 200                 205 agg gga gag tgt tag                                                 639
Arg Gly Glu Cys
    210

<210> SEQ ID NO 6
<211> LENGTH: 212
<212> TYPE: PRT
<213> ORGANISM: Homo sapiens

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ile Phe
                85                  90                  95

Gly Gln Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

```
<210> SEQ ID NO 7
<211> LENGTH: 441
<212> TYPE: PRT
<213> ORGANISM: Homo sapiens
<220> FEATURE:
<221> NAME/KEY: CHAIN
<222> LOCATION: (1)...(441)
<223> OTHER INFORMATION: HvCD37-6b15.1.1 heavy chain
<220> FEATURE:
<221> NAME/KEY: SITE
<222> LOCATION: (1)...(115)
<223> OTHER INFORMATION: heavy chain variable region
<220> FEATURE:
<221> NAME/KEY: SITE
<222> LOCATION: (116)...(441)
<223> OTHER INFORMATION: human IgG2 constant region

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Pro Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Gly Asp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
```

```
                   305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
        370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 8
<211> LENGTH: 212
<212> TYPE: PRT
<213> ORGANISM: Homo sapiens
<220> FEATURE:
<221> NAME/KEY: CHAIN
<222> LOCATION: (1)...(212)
<223> OTHER INFORMATION: HvCD37-6b15.1.1 light chain
<220> FEATURE:
<221> NAME/KEY: SITE
<222> LOCATION: (1)...(106)
<223> OTHER INFORMATION: light chain variable region
<220> FEATURE:
<221> NAME/KEY: SITE
<222> LOCATION: (107)...(212)
<223> OTHER INFORMATION: human kappa constant region

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ile Phe
                85                  90                  95

Gly Gln Gly Thr Lys Leu Glu Ile Lys Arg Thr Val Ala Ala Pro Ser
                100                 105                 110

Val Phe Ile Phe Pro Pro Ser Asp Glu Gln Leu Lys Ser Gly Thr Ala
                115                 120                 125

Ser Val Val Cys Leu Leu Asn Asn Phe Tyr Pro Arg Glu Ala Lys Val
            130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175
```

-continued

```
Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 9
<211> LENGTH: 346
<212> TYPE: DNA
<213> ORGANISM: Homo sapiens
<220> FEATURE:
<221> NAME/KEY: CDS
<222> LOCATION: (1)...(346)

<400> SEQUENCE: 9 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
  1               5                  10                  15 acc ctg tcc ctc acc tgc gct gtc tat ggt ggg tcc ttc agt cct tac      96
Thr Leu Ser Leu Thr Cys Ala Val Tyr Gly Gly Ser Phe Ser Pro Tyr
             20                  25                  30 tac tgg agc tgg atc cgc cag ccc cca ggg aag ggg ttg gag tgg att     144
Tyr Trp Ser Trp Ile Arg Gln Pro Pro Gly Lys Gly Leu Glu Trp Ile
         35                  40                  45 ggg gaa atc aat cat agt gga agc acc aac tac aac ccg tcc ctc aag     192
Gly Glu Ile Asn His Ser Gly Ser Thr Asn Tyr Asn Pro Ser Leu Lys
     50                  55                  60 agt cga gtc acc att tca gta gac acg tcc aag aac cag ttc tcc ctg     240
Ser Arg Val Thr Ile Ser Val Asp Thr Ser Lys Asn Gln Phe Ser Leu
 65                  70                  75                  80 aag ctg agc tct gtg acc gcc gcg gac acg gct gtc tat tac tgt gcg     288
Lys Leu Ser Ser Val Thr Ala Ala Asp Thr Ala Val Tyr Tyr Cys Ala
                 85                  90                  95 agg aga gct ggg gac ttt gac tac tgg ggc cag gga acc ctg gtc acc     336
Arg Arg Ala Gly Asp Phe Asp Tyr Trp Gly Gln Gly Thr Leu Val Thr
            100                 105                 110 gtc tcc tca g                                                        346
Val Ser Ser
        115

<210> SEQ ID NO 10
<211> LENGTH: 115
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Pro Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Ala Gly Asp Phe Asp Tyr Trp Gly Gln Gly Thr Leu Val Thr
```

<210> SEQ ID NO 11
<211> LENGTH: 318
<212> TYPE: DNA
<213> ORGANISM: Homo sapiens
<220> FEATURE:
<221> NAME/KEY: CDS
<222> LOCATION: (1)...(318)

<400> SEQUENCE: 11

```
gac atc cag atg acc cag tct cct tcc acc ctg tct gca tct gtt gga      48
Asp Ile Gln Met Thr Gln Ser Pro Ser Thr Leu Ser Ala Ser Val Gly
 1               5                  10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
             20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
         35                  40                  45 tat aag gcg tct agt tta gaa agt ggg gtc cca tca agg ttt agc ggc     192
Tyr Lys Ala Ser Ser Leu Glu Ser Gly Val Pro Ser Arg Phe Ser Gly
     50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
 65                  70                  75                  80 gat gat ttt gca act tat tac tgc caa cag tat aat agt tac att ttt     288
Asp Asp Phe Ala Thr Tyr Tyr Cys Gln Gln Tyr Asn Ser Tyr Ile Phe
                 85                  90                  95 ggc cag ggg acc aag ctg gag atc aaa cgg                              318
Gly Gln Gly Thr Lys Leu Glu Ile Lys Arg
            100                 105
```

<210> SEQ ID NO 12
<211> LENGTH: 106
<212> TYPE: PRT
<213> ORGANISM: Homo sapiens

<400> SEQUENCE: 12

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ile Phe
                 85                  90                  95

Gly Gln Gly Thr Lys Leu Glu Ile Lys Arg
            100                 105
```

<210> SEQ ID NO 13
<211> LENGTH: 4
<212> TYPE: PRT
<213> ORGANISM: Artificial Sequence
<220> FEATURE:

```
<223> OTHER INFORMATION: Linker

<400> SEQUENCE: 13

Gly Phe Leu Gly
1
```

ANTIBODY DRUG CONJUGATES (ADC) THAT BIND TO CD37 PROTEINS

CROSS-REFERENCE TO RELATED APPLICATIONS

This application is a continuation application of U.S. patent application Ser. No. 14/447,209, filed Jul. 30, 2014, now U.S. Pat. No. 9,925,273, issued Mar. 27, 2018, which claims the benefit of priority to United Stated Provisional Patent Application No. 61/861,321, filed Aug. 1, 2013, the disclosures of each of which are incorporated by reference herein in their entireties.

SEQUENCE LISTING

The content of the following submission on ASCII text file is incorporated herein by reference in its entirety: a computer readable form (CRF) of the Sequence Listing, entitled "14369-240-999_SUB_SEQ_LISTING.txt," of file size 32,295 bytes, created on Nov. 14, 2019.

FIELD OF THE INVENTION

The invention described herein relates in some aspects to antibodies, antigen-binding fragments thereof, and antibody drug conjugates (ADCs) thereof, that bind proteins, termed CD37. The invention further relates in some aspects to prognostic, prophylactic and therapeutic methods and compositions useful in the treatment of cancers that express CD37.

BACKGROUND OF THE INVENTION

It is estimated that 1,660,290 men and women (854,790 men and 805,500 women) will be diagnosed with and 580,350 men and women will die of cancer of all sites in 2013. From 2006-2010, the median age at diagnosis for cancer of all sites was 66 years of age. The age-adjusted incidence rate was 463.0 per 100,000 men and women per year. These rates are based on cases diagnosed in 2006-2010 from 18 SEER geographic areas. From 2006-2010, the median age at death for cancer of all sites was 72 years of age. The age-adjusted death rate was 176.4 per 100,000 men and women per year. These rates are based on patients who died in 2006-2010 in the US. The overall 5-year relative survival for 2003-2009 from 18 SEER geographic areas was 65.8%.

Non-Hodgkin lymphomas (NHLs) can occur at any age and are often marked by lymph nodes that are larger than normal, fever, and weight loss. There are many different types of non-Hodgkin lymphoma. These types can be divided into aggressive (fast-growing) and indolent (slow-growing) types, and they can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma. Lymphomas that occur after bone marrow or stem cell transplantation are usually B-cell non-Hodgkin lymphomas. Prognosis and treatment depend on the stage and type of disease.

It is estimated that 69,740 men and women (37,600 men and 32,140 women) will be diagnosed with and 19,020 men and women will die of non-Hodgkin lymphoma in 2013. From 2006-2010, the median age at diagnosis for non-Hodgkin lymphoma was 66 years of age. The age-adjusted incidence rate was 19.7 per 100,000 men and women per year. These rates are based on cases diagnosed in 2006-2010 from 18 SEER geographic areas. From 2006-2010, the median age at death for non-Hodgkin lymphoma was 76 years of age. The age-adjusted death rate was 6.4 per 100,000 men and women per year. These rates are based on patients who died in 2006-2010 in the US. The overall 5-year relative survival for 2003-2009 from 18 SEER geographic areas was 69.0%.

Leukemias are cancers that start in blood-forming tissue such as the bone marrow and causes large numbers of blood cells to be produced and enter the bloodstream. The major leukemias are comprised of Acute Lymphoblastic (ALL), Acute Myeloid (AML), Chronic Lymphocytic (CLL), Chronic Myelogenous (CML), and Hairy Cell (CLL) Leukemia.

For these leukemias as a group, it is estimated that 48,610 men and women (27,880 men and 20,730 women) will be diagnosed with and 23,720 men and women will die of leukemia in 2013. From 2006-2010, the median age at diagnosis for leukemia was 66 years of age. The age-adjusted incidence rate was 12.8 per 100,000 men and women per year. These rates are based on cases diagnosed in 2006-2010 from 18 SEER geographic areas. From 2006-2010, the median age at death for leukemia was 75 years of age. The age-adjusted death rate was 7.1 per 100,000 men and women per year. These rates are based on patients who died in 2006-2010 in the US. The overall 5-year relative survival for 2003-2009 from 18 SEER geographic areas was 56.0%.

CLL is the second most common type of leukemia in adults and it usually gets worse slowly. It often occurs during or after middle age and it rarely occurs in children. Patients with early-stage CLL are not treated with chemotherapy until they become symptomatic or display evidence of rapid progression of disease. Early initiation of chemotherapy has failed to show benefit in CLL and may even increase mortality. When chemotherapy is initiated, the nucleoside analogue fludarabine is the most commonly used first-line therapy in CLL. Combination regimens have shown improved response rates in several clinical trials and include the following: Fludarabine, cyclophosphamide, and rituximab (FCR); Pentostatin, cyclophosphamide, and rituximab (PCR); Fludarabine, cyclophosphamide, and mitoxantrone (FCM); Cyclophosphamide, vincristine, and prednisone (CVP); Cyclophosphamide, doxorubicin, vincristine, and prednisone (CHOP). It is estimated that 15,680 men and women (9,720 men and 5,960 women) will be diagnosed with and 4,580 men and women will die of chronic lymphocytic leukemia in 2013. From 2006-2010, the median age at diagnosis for chronic lymphocytic leukemia was 71 years of age. The age-adjusted incidence rate was 4.3 per 100,000 men and women per year. These rates are based on cases diagnosed in 2006-2010 from 18 SEER geographic areas. From 2006-2010, the median age at death for chronic lymphocytic leukemia was 79 years of age. The age-adjusted death rate was 1.4 per 100,000 men and women per year. These rates are based on patients who died in 2006-2010 in the US. The overall 5-year relative survival for 2003-2009 from 18 SEER geographic areas was 79.2%.

Acute myeloid leukemia (AML) is the most common type of acute leukemia among adults. Current treatment of AML should be sufficiently aggressive to achieve complete remission (CR) because partial remission offers no substantial survival benefit. Remission rates in adult AML are inversely related to age, with an expected remission rate of more than 65% for those younger than 60 years. Data suggest that once attained, duration of remission may be shorter in older patients. Patients that express the progenitor cell antigen CD34 and/or the P-glycoprotein (MDR1 gene product) have an inferior outcome. Cytogenetic analysis provides some of the strongest prognostic information available, predicting outcome of both remission induction and post remission therapy. Cytogenetic abnormalities that indicate a good prognosis include t(8; 21), inv(16) or t(16;16), and t(15;17). Normal cytogenetics portends average-risk AML. Patients with AML that is characterized by deletions of the long arms or monosomies of chromosomes 5 or 7; by translocations or inversions of chromosome 3, t(6; 9), t(9; 22); or by abnormalities of chromosome 11q23 have particularly poor prognoses with chemotherapy. It is estimated that 14,590 men and women (7,820 men and 6,770 women) will be diagnosed with and 10,370 men and women will die of acute myeloid leukemia in 2013. From 2006-2010, the median age at diagnosis for acute myeloid leukemia was 67 years of age. The age-adjusted incidence rate was 3.7 per 100,000 men and women per year. These rates are based on cases diagnosed in 2006-2010 from 18 SEER geographic areas. From 2006-2010, the median age at death for acute myeloid leukemia was 72 years of age. The age-adjusted death rate was 2.8 per 100,000 men and women per year. These rates are based on patients who died in 2006-2010 in the US. The overall 5-year relative survival for 2003-2009 from 18 SEER geographic areas was 24.2%. Note, all general cancer information was obtained from the NCI website and all statistics are based on SEER incidence and NCHS mortality statistics found within: Howlader N., et. al., SEER Cancer Statistics Review, 1975-2010, National Cancer Institute. Bethesda, Md., based on November 2012 SEER data submission, posted to the SEER web site, 2013.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.).

Additionally, antibodies can be prepared using VelocImmune transgenic mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638,768, and 6,528,314.

SUMMARY OF THE INVENTION

The invention in some aspects provides antibodies, antigen-binding fragments, and antibody drug conjugates (ADCs) thereof that bind to CD37 proteins and polypeptide fragments of CD37 proteins. In some embodiments, the invention comprises fully human antibodies conjugated with a therapeutic agent. In certain embodiments, there is a proviso that the entire nucleic acid sequence of FIGS. 2A and 2B is not encoded and/or the entire amino acid sequence of FIGS. 3A and 3B is not prepared. In certain embodiments, the entire nucleic acid sequence of FIGS. 2A and 2B is encoded and/or the entire amino acid sequence of FIGS. 3A and 3B is prepared, either of which are in respective human unit dose forms.

The invention in some aspects further provides various immunogenic or therapeutic compositions, such as antibody drug conjugates, and strategies for treating cancers that express CD37 such as cancers of tissues listed in Table I (e.g., AML, CLL, NHL, and MM).

BRIEF DESCRIPTION OF THE FIGURES

FIG. 1. The cDNA and amino acid sequence of CD37 is shown in FIG. 1. The start methionine is underlined. The open reading frame extends from nucleic acid 122-967 including the stop codon.

FIGS. 2A and 2B. Nucleic Acid and Amino Acid sequences of CD37 antibodies.

FIG. 2A. The cDNA and amino acid sequence of HvCD37-6b15.1.1 heavy chain. Double-underlined is the heavy chain variable region, underlined is the heavy chain variable region, and underlined is the heavy chain human IgG2 constant region.

FIG. 2B. The cDNA and amino acid sequence of HvCD37-6b15.1.1 light chain. Double-underlined is the light chain variable region, underlined is the human kappa constant region.

FIGS. 3A and 3B. Amino Acid sequences of CD37 antibodies.

FIG. 3A. The amino acid sequence of HvCD37-6b15.1.1 heavy chain. Double-underlined is the heavy chain variable region, and underlined is the human IgG2 constant region.

FIG. 3B. The amino acid sequence of HvCD37-6b15.1.1 light chain. Double-underlined is the light chain variable region, and underlined is the human kappa constant region.

FIGS. 4A and 4B. Alignment of HvCD37-6b15.1.1 antibodies to human Ig germline.

FIG. 4A. Alignment of HvCD37-6b15.1.1 heavy chain variable region (SEQ ID NO:9) to human Ig germline.

FIG. 4B. Alignment of HvCD37-6b15.1.1 light chain variable region (SEQ ID NO:11) to human Ig germline.

FIG. 5. Efficacy study of HvCD37-6b15.1.1.vcMMAE in subcutaneously established human follicular B cell lymphoma DoHH2 implanted in CB17/SCID mice.

FIG. 6. Efficacy Study of HvCD37-6b15.1.1.vcMMAE in Subcutaneously Established Xenograft Model of Human Lymphoma Ramos-RR-XCL Implanted in CB17/SCID Mice.

FIG. 7. Efficacy study of HvCD37-6b15.1.1.vcMMAE in subcutaneously established human chronic lymphocytic leukemia JVM3 implanted in CB17/SCID mice.

FIG. 8. Efficacy study of HvCD37-6b15.1.1.vcMMAE in subcutaneously established human Acute Myelogenous Leukemia MV-4-11 implanted in CB17/SCID mice.

FIG. 9. Efficacy study of several CD37 ADCs in subcutaneously established human Rituxan resistant lymphoma cell line Ramos-RR-XCL implanted in SCID mice.

FIGS. 10(A) and 10(B) shows NHL patient specimens. FIGS. 10(C) and 10(D) shows MM patient specimens.

FIG. 12A-D. Expression of CD37 in B cell lines: FACS using HvCD37-6b15.1.1 IgG2.

FIGS. 13A-C. Expression of CD37 in AML cell lines: FACS using HvCD37-6b15.1.1 IgG2.

DETAILED DESCRIPTION OF THE INVENTION

Figure 10:
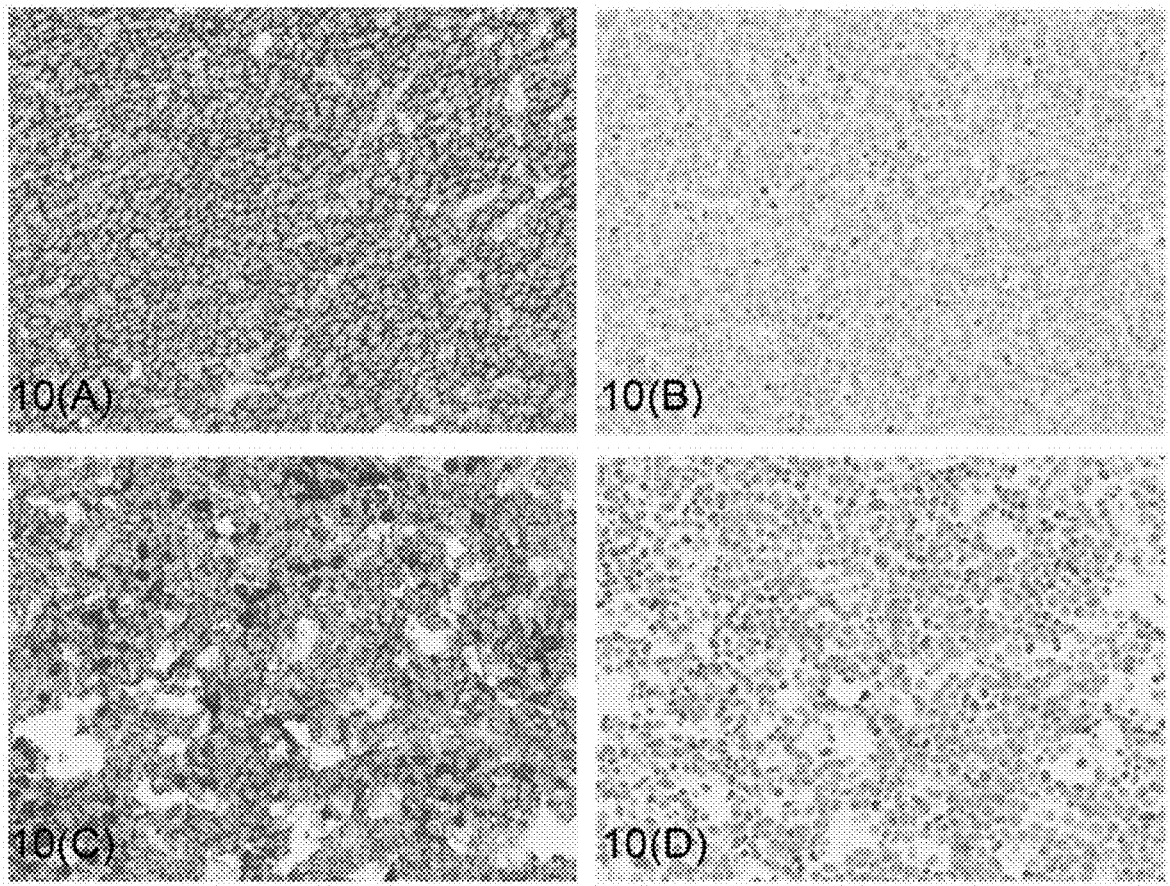
FIG. 10. Detection of CD37 protein in cancer patient specimens by IHC.

Outline of Sections
I.) Definitions
II.) CD37 Antibodies
III.) Antibody Drug Conjugates Generally
   III(A). Maytansinoids
   III(B). Auristatins and dolostatins
   III(C). Calicheamicin
   III(D). Other Cytotoxic Agents
IV.) Antibody Drug Conjugates which Bind CD37
V.) Linker Units
VI.) The Stretcher Unit
VII.) The Amino Acid Unit
VIII.) The Spacer Unit
IX.) The Drug Unit
X.) Drug Loading
XI.) Methods of Determining Cytotoxic effect of ADCs
XII.) Treatment of Cancer(s) Expressing CD37
XIII.) CD37 as a Target for Antibody-based Therapy
XIV.) CD37 ADC Cocktails
XV.) Combination Therapy
XVI.) Kits/Articles of Manufacture

I.) Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. Edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The abbreviation "AFP" refers to dimethylvaline-valine-dolaisoleuine-dolaproine-phenylalanine-p-phenylenediamine (see Formula XVI infra).

The abbreviation "MMAE" refers to monomethyl auristatin E (see Formula XI infra).

The abbreviation "AEB" refers to an ester produced by reacting auristatin E with paraacetyl benzoic acid (see Formula XX infra).

The abbreviation "AEVB" refers to an ester produced by reacting auristatin E with benzoylvaleric acid (see Formula XXI infra).

The abbreviation "MMAF" refers to dovaline-valine-dolaisoleuine-dolaproine-phenylalanine (see Formula XVIV infra).

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl, and wherein said —O—(C$_1$-C$_8$ alkyl), —O—(C$_2$-C$_8$ alkenyl), —O—(C$_2$-C$_8$ alkynyl), -aryl, —C$_1$-C$_8$ alkyl, —C$_2$-C$_8$ alkenyl, and —C$_2$-C$_8$ alkynyl groups can be optionally further substituted with one or more groups including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$—C alkenyl), —O—(C$_2$—C alkynyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —C$_1$-C$_8$ alkyl, —C$_2$-C$_8$ alkenyl, —C$_2$-C$_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited to, -halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), -aryl, —C$_1$-C$_8$ alkyl, —C$_2$-C$_8$ alkenyl, and —C$_2$-C$_8$ alkynyl groups can be optionally further substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —C$_1$-C$_8$ alkyl, —C$_2$-C$_8$ alkenyl, —C$_2$-C$_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, octylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), -aryl, —C$_1$-C$_8$ alkyl, —C$_2$-C$_8$ alkenyl, and —C$_2$-C$_8$ alkynyl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —C$_1$-C$_8$ alkyl, —C$_2$-C$_8$ alkenyl, —C$_2$-C$_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CHCH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —C$_1$-C$_8$ alkyl, —C$_2$-C$_8$ alkenyl, —C$_2$-C$_8$ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group.

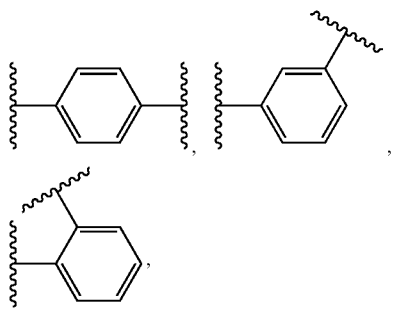

Typical "—(C$_1$-C$_8$ alkylene)aryl," "—(C$_2$-C$_8$ alkenylene) aryl", "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Examples of monocyclic carbocyclic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl. -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds provided herein can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the provided embodiments are pharmaceutically acceptable and may or may not need to be cleaved from the parent compound after administration to a subject in order for the compound to be active. Cleavage is through normal metabolic processes within the body. Hydroxy protecting groups are well known in the art, see, Protective Groups in Organic Synthesis by T. W. Greene and P. G. M. Wuts (John Wiley & sons, $3^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-chloro-4-methyl)phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphneylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1,-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —$R^a$, —Si($R^a$)($R^a$)($R^a$), —C(O)$R^a$, —C(O)O$R^a$, —C(O)NH($R^a$), —S(O)$_2R^a$, —S(O)$_2$OH, P(O)(OH)$_2$, and —P(O)(OH)O$R^a$, wherein $R^a$ is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, alkynylene, aryl, carbocycle, and heterocycle radicals whether alone or as part of another group are optionally substituted.

"Altering the native glycosylation pattern" is intended for purposes herein to mean deleting one or more carbohydrate moieties found in native sequence CD37 (either by removing the underlying glycosylation site or by deleting the glycosylation by chemical and/or enzymatic means), and/or adding one or more glycosylation sites that are not present in the native sequence CD37. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a CD37-related protein). For example, an analog of a CD37 protein can be specifically bound by an antibody or T cell that specifically binds to CD37.

The term "antibody" is used in the broadest sense unless clearly indicated otherwise. Therefore, an "antibody" can be naturally occurring or man-made such as monoclonal antibodies produced by conventional hybridoma technology. CD37 antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds CD37 and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind CD37 and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention in some embodiments is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective CD37. See e.g., ANTIBODY ENGINEERING: A PRACTICAL APPROACH (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the CD37 or its receptor.

The term "antigen-binding portion" or "antibody fragment" of an antibody (or simply "antibody portion"), as used herein, refers to one or more fragments of a CD37 antibody that retain the ability to specifically bind to an antigen (e.g., CD37 and variants; FIG. 1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for CD37. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion", in the context of an antigen, refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the CD37 of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies described herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The term "chemotherapeutic agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," *J. Mol. Biol.* 262, 732-745." ("Contact" numbering scheme), Lefranc M P et al., "IMGT unique numbering for immunoglobulin and T cell receptor variable domains and Ig superfamily V-like domains," *Dev Comp Immunol*, 2003 January; 27(1):55-77 ("IMGT" numbering scheme), and Honegger A and Plückthun A, "Yet another numbering scheme for immunoglobulin variable domains: an automatic modeling and analysis tool," *J Mol Biol*, 2001 Jun. 8; 309(3):657-70, (AHo numbering scheme).

The boundaries of a given CDR may vary depending on the scheme used Table V, infra, lists exemplary positions for CDR-L1, CDR-L2, CDR-L3 and CDR-H1, CDR-H2, CDR-H3 according to Kabat, Chothia, and Contact schemes, respectively. For CDR-H1, residue numbering is given listed using both the Kabat and Chothia numbering schemes.

Thus, unless otherwise specified, the terms "CDR" and "complementary determining region" of a given antibody or region thereof, such as a variable region, as well as individual CDRs (e.g., "CDR-H1, CDR-H2) and framework regions (FRs) of the antibody or region thereof, should be understood to encompass respective region (e.g., the complementary determining region) as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table II and Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins (e.g., auristatin E, auristatin F, MMAE and MMAF), auromycins, maytansinoids, ricin, ricin A-chain, combrestatin, duocarmycins, dolastatins, doxorubicin, daunorubicin, taxols, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Antibodies may also be conjugated to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The term "deplete," in the context of the effect of a CD37 binding agent on CD37-expressing cells, refers to a reduction in the number of or elimination of the CD37-expressing cells.

The term "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. MONOCLONAL ANTIBODIES AND CANCER THERAPY 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188:483-95 (1998).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

The terms "inhibit" or "inhibition of" as used herein means to reduce by a measurable amount, or to prevent entirely.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the CD37 genes or that encode polypeptides other than CD37 gene product or fragments thereof. A skilled artisan can readily employ nucleic acid isolation procedures to obtain an isolated CD37 polynucleotide. A protein is said to be "isolated," for example, when physical, mechanical or chemical methods are employed to remove the CD37 proteins from cellular constituents that are normally associated with the protein. A skilled artisan can readily employ standard purification methods to obtain an isolated CD37 protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., Nat. Biotechnol. 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+ under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates, or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, in some embodiments can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention in some embodiments may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter (See, Table III) or single letter designations for amino acids are used. In the art, this term is often used interchangeably with "peptide" or "protein".

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the CD37 antigen, but does not bind to the irrelevant antigen. In another embodiment, a specific antibody is one that binds human CD37 antigen but does not bind a non-human CD37 antigen with 70%, 75%, 80%, 85%, 90%, 91%, 92%, 93%, 94%, 95%, 96%, 97%, 98%, 99% or greater amino acid homology with the CD37 antigen. In another embodiment, a specific antibody is one that binds human CD37 antigen and binds murine CD37 antigen, but with a higher degree of binding the human antigen. In another embodiment, a specific antibody is one that binds human CD37 antigen and binds primate CD37 antigen, but with a higher degree of binding the human antigen. In another embodiment, the specific antibody binds to human CD37 antigen and any non-human CD37 antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "variant" refers to a molecule that exhibits a variation from a described type or norm, such as a protein that has one or more different amino acid residues in the corresponding position(s) of a specifically described protein (e.g. the CD37 protein shown in FIG. 1.) An analog is an example of a variant protein. Splice isoforms and single nucleotides polymorphisms (SNPs) are further examples of variants.

The "CD37 proteins" and/or "CD37 related proteins" of the invention include those specifically identified herein (see, FIG. 1), as well as allelic variants, conservative substitution variants, analogs and homologs that can be isolated/generated and characterized without undue experimentation following the methods outlined herein or readily available in the art. Fusion proteins that combine parts of different CD37 proteins or fragments thereof, as well as fusion proteins of a CD37 protein and a heterologous polypeptide are also included. Such CD37 proteins are collectively referred to as the CD37-related proteins, the proteins of the invention, or CD37. The term "CD37-related protein" refers to a polypeptide fragment or a CD37 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 276, 277, 278, 279, 280, or 281 or more amino acids.

II.) CD37 Antibodies

Another aspect of the invention provides antibodies that bind to CD37-related proteins (See FIG. 1). In one embodiment, the antibody that binds to CD37-related proteins is an antibody that specifically binds to CD37 protein comprising amino acid sequence of SEQ ID NO.: 2. The antibody that specifically binds to CD37 protein comprising amino acid sequence of SEQ ID NO.: 2 includes antibodies that can bind to other CD37-related proteins. For example, antibodies that bind CD37 protein comprising amino acid sequence of SEQ ID NO.: 2 can bind CD37-related proteins such as CD37 variants and the homologs or analogs thereof.

In some embodiments, CD37 antibodies of the invention are particularly useful in cancer (see, e.g., Table I) prognostic assays, imaging, diagnostic, and therapeutic methodologies. Similarly, such antibodies are useful in the treatment, and/or prognosis of acute myeloid leukemia ("AML"), chronic lymphocytic leukemia ("CLL"), non hodgkins lymphoma ("NHL") and other cancers, to the extent CD37 is also expressed or overexpressed in these other cancers. Moreover, intracellularly expressed antibodies (e.g., single chain antibodies) are therapeutically useful in treating cancers in which the expression of CD37 is involved, such as advanced or metastatic AML, CLL, NHL, or MM cancers or other advanced or metastatic cancers.

Various methods for the preparation of antibodies, specifically monoclonal antibodies, are well known in the art. For example, antibodies can be prepared by immunizing a suitable mammalian host using a CD37-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of CD37 can also be used, such as a CD37 GST-fusion protein. In a particular embodiment, a GST fusion protein comprising all or most of the amino acid sequence of FIG. 1 is produced, and then used as an immunogen to generate appropriate antibodies. In another embodiment, a CD37-related protein is synthesized and used as an immunogen.

In addition, naked DNA immunization techniques known in the art are used (with or without purified CD37-related protein or CD37 expressing cells) to generate an immune response to the encoded immunogen (for review, see Donnelly et al., 1997, Ann. Rev. Immunol. 15: 617-648).

The amino acid sequence of a CD37 protein as shown in FIG. 1 can be analyzed to select specific regions of the CD37 protein for generating antibodies. For example, hydrophobicity and hydrophilicity analyses of a CD37 amino acid sequence are used to identify hydrophilic regions in the CD37 structure. Regions of a CD37 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of CD37 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a CD37 immunogen is often conducted by injection over a suitable time period and with use of a suitable adjuvant, as is understood in the art. During the immunization schedule, titers of antibodies can be taken to determine adequacy of antibody formation.

CD37 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a CD37-related protein. When the appropriate immortalized cell culture is identified, the cells can be expanded and antibodies produced either from in vitro cultures or from ascites fluid.

The antibodies or fragments of the invention in some embodiments can also be produced by recombinant means. Regions that bind specifically to the desired regions of a CD37 protein can also be produced in the context of chimeric or complementarity-determining region (CDR) grafted antibodies of multiple species origin. Humanized or human CD37 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, human monoclonal antibodies of the invention can be prepared using VelocImmune mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638, 768, and 6,528,314.

In addition, human antibodies of the invention in some embodiments can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention in some embodiments can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention in some embodiments can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Additionally, human antibodies of the present invention in some embodiments can be made with techniques using transgenic mice, inactivated for antibody production, engineered with human heavy and light chains loci referred to as Xenomouse (Amgen Fremont, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A. & Green, L. L., Curr. Opin. Biotechnol 13, 593-597 (2002).

Figure 4A:
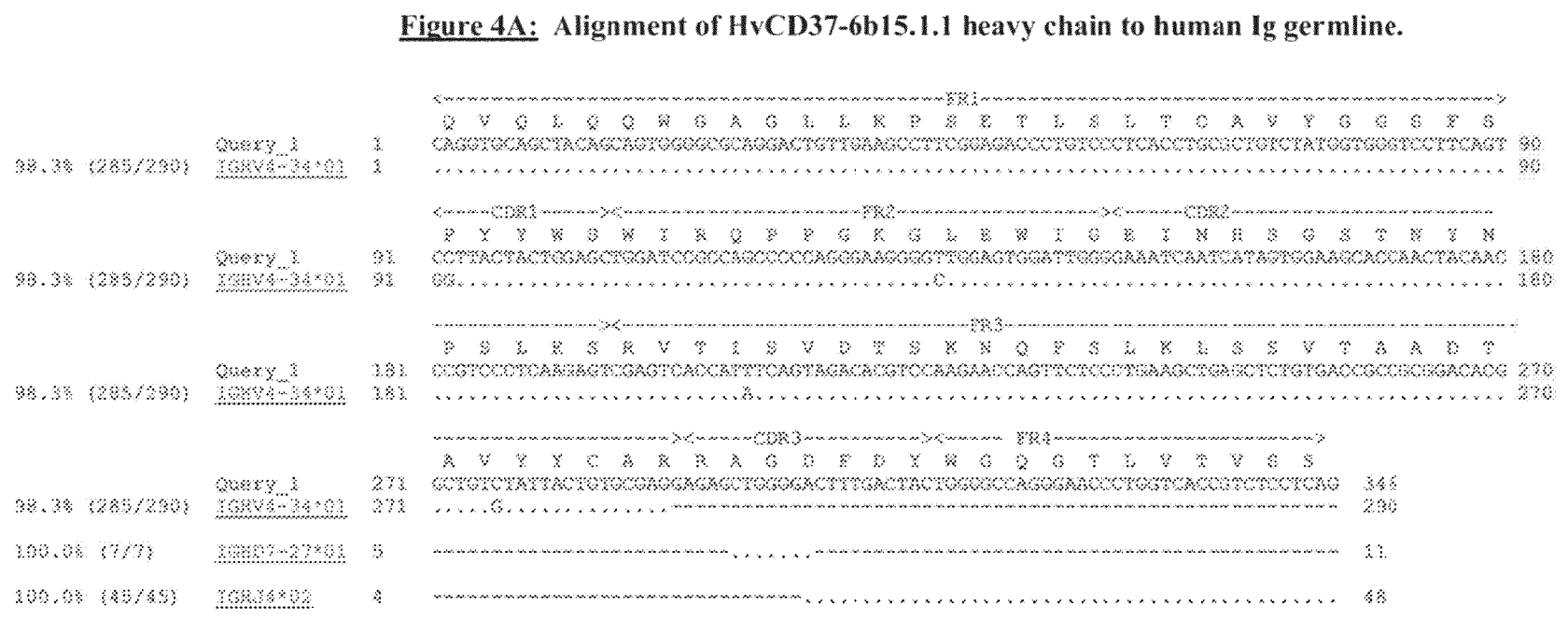

In a preferred embodiment, an CD37 MAbs of the invention comprises heavy and light chain variable regions of an antibody designated HvCD37-6b15.1.1 produced by a Chinese Hamster Ovary (CHO) cell deposited under the American Type Culture Collection (ATCC) Accession No.: PTA-120464 (See, FIG. 3A or 3B), or heavy and light variable regions comprising amino acid sequences that are homologous to the amino acid sequences of the heavy and light chain variable regions of HvCD37-6b15.1.1, and wherein the antibodies retain the desired functional properties of the CD37 MAbs of the invention. The heavy chain variable region of HvCD37-6b15.1.1 consists of the amino acid sequence ranging from $1^{st}$ residue (Q) to the $115^{th}$ residue (S) residue of SEQ ID NO: 7, and the light chain variable region of HvCD37-6b15.1.1 consists of the amino acid sequence ranging from $1^{st}$ residue (D) to the $106^{th}$ residue (R) residue of SEQ ID NO: 8. In one embodiment, the CDRs1-3 (Kabat) of heavy chain variable region of HvCD37-6b15.1.1 consist, respectively, of the amino acid sequence ranging from 31-35, from 50-65, and from 98-104 of SEQ ID NO: 7 respectively, and the CDR1-3 of the light chain variable region of HvCD37-6b15.1.1 consists of the amino acid sequence ranging from 24-34, from 50-56, and from 89-95 of SEQ ID NO: 8 (See, FIG. 4 and Table V). In some embodiments, CDR-H1 comprises or consists of PYYWS (position 31-35 of SEQ ID NO: 7); CDR-H2 comprises or consists of EINHSGSTNYNPSLKS (position 50-65 of SEQ ID NO: 7); CDR-H3 comprises or consists of RAGDFDY (position 98-104 of SEQ ID NO: 7), CDR-L1 comprises or consists of RASQSISSWLA (position 24-34 of SEQ ID NO: 8), CDR-L2 comprises or consists of KASSLES (position 50-56 of SEQ ID NO: 8), and/or CDR-L3 comprises or consists of QQYNSYI (position 89-95 of SEQ ID NO: 8). As the constant region of an antibody of the invention, any subclass of constant region can be chosen. In one embodiment, human IgG2 constant region as the heavy chain constant region and human Ig kappa constant region as the light chain constant region can be used.

For example, in some embodiments, the invention provides an isolated monoclonal antibody, or antigen binding portion thereof, comprising a heavy chain variable region and a light chain variable region, wherein:
  (a) the heavy chain variable region comprises an amino acid sequence that is at least 80% homologous to heavy chain variable region amino acid sequence set forth in FIG. 3A; and
  (b) the light chain variable region comprises an amino acid sequence that is at least 80% homologous to the light chain variable region amino acid sequence set forth in FIG. 3B.

In other embodiments, the $V_H$ and/or $V_L$ amino acid sequences may be 85%, 86%, 87%, 88%, 89%, 90%, 91%, 92%, 93%, 94%, 95%, 96%, 97%, 98% or 99% homologous to the $V_H$ and $V_L$ sequences set forth in FIG. 3A or 3B.

In another embodiment, the invention provides an isolated monoclonal antibody, or antigen binding portion thereof, comprising a humanized heavy chain variable region and a humanized light chain variable region, wherein:
  (a) the heavy chain variable region comprises complementarity determining regions (CDRs) having the amino acid sequences of the heavy chain variable region CDRs set forth in FIG. 3A;
  (b) the light chain variable region comprises CDRs having the amino acid sequences of the light chain variable region CDRs set forth in FIG. 3B.

In some embodiments, the antibody has a CDR-H1 which comprises or consists of PYYWS (position 31-35 of SEQ ID NO: 7); a CDR-H2 which comprises or consists of EINHSGSTNYNPSLKS (position 50-65 of SEQ ID NO: 7); a CDR-H3 which comprises or consists of RAGDFDY (position 98-104 of SEQ ID NO: 7), a CDR-L1 which comprises or consists of RASQSISSWLA (position 24-34 of SEQ ID NO: 8), a CDR-L2 which comprises or consists of KASSLES (position 50-56 of SEQ ID NO: 8), and/or a CDR-L3 which comprises or consists of QQYNSYI (position 89-95 of SEQ ID NO: 8).

Engineered antibodies of the invention in some embodiments include those in which modifications have been made to framework residues within $V_H$ and/or $V_L$ (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may in some embodiments be engineered to include modifications within the Fc region, typically to alter one or more functional properties of the antibody, such as serum half-life, complement fixation, Fc receptor binding, and/or antigen-dependent cellular cytotoxicity. Furthermore, a CD37 MAb of the invention may in some embodiments be chemically modified (e.g., one or more chemical moieties can be attached to the antibody) or be modified to alter its glycosylation, again to alter one or more functional properties of the MAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the CD37 MAb.

In another embodiment, the Fc hinge region of an antibody is mutated to decrease the biological half life of the CD37 MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the CD37 MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the CD37 MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of CD37 antibodies with a CD37-related protein can be established by a number of well known means, including Western blot, immunoprecipitation, ELISA, and FACS analyses using, as appropriate, CD37-related proteins, CD37-expressing cells or extracts thereof. A CD37 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more CD37 epitopes are generated using methods generally known in the art. Homodimeric antibodies can also be generated by cross-linking techniques known in the art (e.g., Wolff et al., Cancer Res. 53: 2560-2565).

In yet another preferred embodiment, the CD37 MAb of the invention is an antibody comprising heavy and light chain of an antibody designated HvCD37-6b15.1.1. The heavy chain of HvCD37-6b15.1.1 consists of the amino acid sequence ranging from $1^{st}$ residue (Q) to the $441^{st}$ residue (K) of SEQ ID NO: 7 and the light chain of HvCD37-6b15.1.1 consists of amino acid sequence ranging from $1^{st}$ residue (D) to the $212^{th}$ residue (C) of SEQ ID NO: 8 sequence. The sequence of which is set forth in FIGS. 2A and 2B and FIGS. 3A and 3B. In a preferred embodiment, HvCD37-6b15.1.1 is conjugated to a cytotoxic agent.

In yet another embodiment, the CD37 MAb of the invention is produced by the method of producing an antibody or antigen binding fragment comprising culturing a host cell to allow expression of antibody or antigen binding fragment, wherein the host cell is selected from the group consisting of the following (a) to (d):

(a) a host cell transformed with an expression vector comprising a polynucleotide comprising a base sequence encoding a heavy chain variable region consisting of the amino acid sequence ranging from the 1st Q to the 115th S of SEQ ID NO: 7 and a polynucleotide comprising a base sequence encoding a light chain variable region consisting of the amino acid sequence ranging from the 1st D to the 106th R SEQ ID NO: 8;

(b) a host cell transformed with an expression vector comprising a polynucleotide comprising a base sequence encoding a heavy chain variable region consisting of the amino acid sequence ranging from the 1st Q to the 115th S of SEQ ID NO: 7 and an expression vector comprising a polynucleotide comprising a base sequence encoding a light chain variable region consisting of the amino acid sequence ranging from the 1st D to the 106th R SEQ ID NO: 8

(c) a host cell transformed with an expression vector comprising a polynucleotide comprising a base sequence encoding a heavy chain variable region consisting of the amino acid sequence ranging from the 1st Q to the 115th S of SEQ ID NO: 7; and (d) a host cell transformed with an expression vector comprising a polynucleotide comprising a base sequence encoding a light chain variable region consisting of the amino acid sequence ranging from the 1st D to the 106th R SEQ ID NO: 8.

In yet another embodiment, the CD37 MAb of the invention is produced by the method of producing an antibody comprising culturing a host cell to allow expression of antibody, wherein the host cell is selected from the group consisting of the following (a) to (d):

(a) a host cell transformed with an expression vector comprising a polynucleotide comprising a base sequence encoding a heavy chain consisting of the amino acid sequence ranging from the 1st Q to the 441th K of SEQ ID NO: 7 and a polynucleotide comprising a base sequence encoding a light chain consisting of the amino acid sequence ranging from the 1 st D to the 212th C of SEQ ID NO: 8;

(b) a host cell transformed with an expression vector comprising a polynucleotide comprising a base sequence encoding a heavy chain consisting of the amino acid sequence ranging from the 1st Q to the 441th K of SEQ ID NO: 7 and an expression vector comprising a polynucleotide comprising a base sequence encoding a light chain consisting of the amino acid sequence ranging from the 1st D to the 212th C of SEQ ID NO: 8

(c) a host cell transformed with an expression vector comprising a polynucleotide comprising a base sequence encoding a heavy chain consisting of the amino acid sequence ranging from the 1st Q to the 441th K of SEQ ID NO: 7; and (d) a host cell transformed with an expression vector comprising a polynucleotide comprising a base sequence encoding a light chain consisting of the amino acid sequence ranging from the 1st D to the 212th C of SEQ ID NO: 8.

The Chinese Hamster Ovary (CHO) cell producing the antibody designated HvCD37-6b15.1.1 was sent (via Federal Express) to the American Type Culture Collection (ATCC), P.O. Box 1549, Manassas, Va. 20108 on 8 Jul. 2013 and assigned Accession number PTA-120464.

Alternatively, or additionally, in another embodiment of the invention, the MAbs which bind CD37, in this case, the MAb HvCD37-6b15.1.1 may undergo post-translational modifications as known in the art. Examples of post-translational modifications include, but are not limited to, chemical modifications, such as disulfide bonds, oligosaccharides, N-terminal pyroglutamate formation, C-terminal lysine processing, deamidation, isomerization, oxidation, glycation, peptide bond cleavage, non-reductible cross-linking, truncation and others known in the art. See, Liu, et. al., Heterogeneity of Monoclonal Antibodies, J. Pharma. Sci. vol. 97, no. 7, pp. 2426-2447 (July 2008). Other types of modifications include noncovalent interaction, conformational heterogeneity, and aggregation. Id.

In a further embodiment, the HvCD37-6b15.1.1 MAb comprises a cyclization of the N-terminal heavy chain Glutamine at residue 1 to Pyro-Glutamate. One of skill in the art will understand and appreciate that such cyclization is understood to occur spontaneously. See, Dick, et. al., Determination of the Origin of the N-Terminal Pyro-Glutamtate Variation in Monoclonal Antibodies Using Model Peptides, Biotechnology and Bioengineering, vol. 97, no. 3, pp 544-553 (Jun. 15, 2007).

Additionally or alternatively, amino acids of the HvCD37-6b15.1.1 MAb may undergo further post-translational modifications including, but not limited to, deamidation, isomerization, glycation, and/or oxidation. The polypeptides of the invention, or the fragments thereof, may undergo additional post-translational modifications, including glycosylation, for example N-linked or O-linked glycosylation sites that are well known in the art. As previous described, changes may be made in the amino acid sequence of the polypeptide or process conditions (such as changes in culture, purification, and/or storage conditions) to preclude or minimize such alterations, or to facilitate them in circumstances where such processing is beneficial. Moreover, such preparations may comprise polypeptides that have varying levels of more than one type of processing related modification(s), for example, a polypeptide may have some, most, or substantially all of a C-terminal lysine removed and/or some, most, or substantially all of an N-terminal amino acid converted to pyroglutamatic acid (for example, the polypeptides shown in FIG. 2A or 2B or FIG. 3A or 3B or in the consensus sequences or antigen-binding fragments). Process conditions such as varying buffer composition and temperature can have significant effects on the extent of such modifications.

In a further embodiment, the HvCD37-6b15.1.1 MAb comprises a truncation of the C-terminal heavy chain Lysine ar residue 445.

In a further embodiment, the HvCD37-6b15.1.1 MAb comprises an addition of glycosylation(s) to the heavy chain Asparagine at residue 295 including, but not limited to, G0 (Asialo-, agalacto, afucosylated bi-antennary complex-type N-glycan; GOF (Asialo-, agalacto, core-fucosylated bi-antennary complex-type N-glycan); Mannose-5 (N-linked Oligomannose-5); G1F (Asialo-, monogalacto, core-fucosylated bi-antennary complex-type N-glycan); G2 (Asialo-, bigalacto, afucosylated bi-antennary complex-type N-glycan); G2F (Asialo-. bigalacto, core-fucosylated bi-antennary complex-type N-glycan); A1 (monosialylated, biantennary N-linked oligosaccharide, Neu5Acid); and/or A2 (Disialylated, biantennary N-linked oligosaccharaide Neu5Acid).

Additionally, or alternatively in another embodiment, the HvCD37-6b15.1.1 MAb comprises the addition of glycation(s) to one or more Serine residues of the light chain. Generally, glycation results from the nonenzymatic reaction between reducing sugars and the N-terminal primary amine or the amine group of lysine side chains. One of skill in the art will understand and appreciate that glycation can mask the positive charge on the N-terminal primary amino acid group or the side chain of lysine residues, which will make the antibody more acidic.

The amino acid sequence of the polypeptides of the invention may be verified by any means known in the art (for example, mass spectrometry) and may be identical to the sequences disclosed herein (See, FIG. 2A or 2B and FIG. 3A or 3B) or may differ from those sequences at one or more amino acid residues as a result of post-translational modification processing. By way of non-limiting example, on all or a portion of the substantially homogenous polypeptides, a C-terminal amino acid from either the light chain or heavy chain may be removed, by proteolytic processing or other processing that occurs during culture. Similarly, N-terminal amino acids may be absent, for example, one (1), two (2), three (3), four (4), or five (5)N-terminal amino acids may be absent.

In another embodiment, the heavy chain variable region of HvCD37-6b15.1.1 MAb is selected from the group consisting of an amino acid sequence ranging from residue 1 (Q) to residue 115 (S) of SEQ ID NO: 7 and an amino acid sequence residue 1 (Q) to residue 115 (S) of SEQ ID NO: 7 wherein the N-terminal residue 1 (Q) is converted to pyroglutamic acid.

In another embodiment, the heavy chain of HvCD37-6b15.1.1 MAb is selected from the group consisting of an amino acid sequence ranging from residue 1 (Q) to residue 441 (K) of SEQ ID NO: 7, an amino acid sequence ranging from residue 1 (Q) to residue 441 (K) of SEQ ID NO: 7 wherein the N-terminal residue 1 (Q) is converted to pyroglutamic acid, an amino acid sequence ranging from residue 1 (Q) to residue 441 (K) of SEQ ID NO: 7 wherein the C-terminal residue 441 (K) is removed, and an amino acid sequence ranging from residue 1 (Q) to residue 441 (K) of SEQ ID NO: 7 wherein the N-terminal residue 1 (Q) is converted to pyroglutamic acid and the C-terminal residue 441 (K) is removed.

In another embodiment, the HvCD37-6b15.1.1 MAb or antigen-binding fragment thereof is a recombinantly-produced mixture of proteins obtained by expression in a host cell, wherein the heavy chain variable region of the antibody or antigen-binding fragment thereof is selected from the group consisting of an amino acid sequence ranging from residue 1 (Q) to residue 115 (S) of SEQ ID NO: 7 and an amino acid sequence residue 1 (Q) to residue 115 (S) of SEQ ID NO: 7 wherein the N-terminal residue 1 (Q) is converted to pyroglutamic acid.

In another embodiment, the HvCD37-6b15.1.1 MAb comprises the heavy chain consisting of the amino acid sequence ranging from the 1st Q to the 440th G of SEQ ID NO: 7 wherein the 1st Q is modified to pyroglutamate and the light chain consisting of the amino acid sequence ranging from the 1st D to the 212th C of SEQ ID NO: 8.

III.) Antibody-Drug Conjugates Generally

In another aspect, the invention provides antibody-drug conjugates (ADCs), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the ADCs. In one aspect, an ADC comprises any of the above CD37 MAbs covalently attached to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ZEVALIN® (ibritumomab tiuxetan, Biogen/Idec) which is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69).

Also, MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001).

Additionally, CD37-binding agents are also being tested as potential therapeutics for B-cell malignancies. Emergent Biosolutions (formerly Trubion Pharmaceuticals) developed the CD37-binding agents SMIP-016 and TRU-016 (Zhao et al., 2007, Blood, 110.2569-2577). SMIP-016 is a single chain polypeptide that includes variable regions from a hybridoma and engineered human constant regions. TRU-016 is a humanized version of the anti-CD37 SMIP protein. See e.g. U.S. Published Application No. 2007/0059306. TRU-016 is being tested clinically for the treatment of chronic lymphocytic leukemia (CLL). Boehringer Ingelheim has also disclosed a CD37 binding agent in International Published Application No. WO 2009/019312. However, no CDC activity has been described for any of these binding agents and no in vitro pro-apoptotic activity has been described in the absence of cross-linking agents.

Also, radio-immunotherapy (RIT) has been attempted using a radio-labeled anti-CD37 antibody MB-1 in two separate trials. Therapeutic doses of $^{131}$I-MB-1 were administered to six relapsed NHL patients (Press et al. 1989 J Clin Oncol. 7(8):1027-38; Press at el. 1993, N Engl J Med. 329(17):1219-24). All six patients achieved a complete remission (CR) with a duration of four to thirty-one months. In another trial, $^{131}$I-MB-1 was administered to ten relapsed NHL patients (Kaminski et al. 1992 J Clin Oncol. 10(11): 1696-711). A total of four patients had a response ranging in duration from two to six months, although only one CR was reported. However, not all patients could be treated due to an unfavorable biodistribution of the radio-label which raised concern for radiation exposure of vital non-target organs. Indeed, RIT related toxicities were observed in these trials including severe myclosupression and cardiopulmonary toxicity. While these clinical data suggest that anti-CD37 radio-immunoconjugates may be effective, these therapies are cumbersome to administer, and at relapse post-RIT patients cannot be retreated with RIT due to the risks associated with high doses of radiation.

In addition, Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others.

Additionally, MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors.

Finally, the auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784).

The CD30 MAb conjugated to MMAE is now commercially available as ADCETRIS (Seattle Genetics, Bothell, Wash.). ADCETRIS (brentuximab vedotin) is a CD-30 directed antibody drug conjugate consisting of three components: 1) the chimeric IgG1 antibody denoted cAC10, specific for human CD30, 2) the microtubule disrupting agent MMAE, and 3) a protease-cleavable linker that covalently attaches MMAE to caC10. See, ADCENTRIS prescribing information.

Further, chemotherapeutic agents useful in the generation of ADCs are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon$^{14}$-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

III(A). Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions.

Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2OR$)(U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA. 1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

III(B). Auristatins and Dolastatins

In some embodiments, the ADC comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238649, the disclosure of which is expressly incorporated by reference in its entirety.

An exemplary auristatin embodiment is MMAE (wherein the wavy line indicates the covalent attachment to a linker (L) of an antibody drug conjugate).

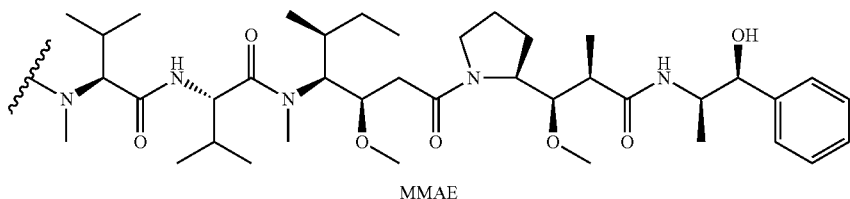 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]
MMAE

Another exemplary auristatin embodiment is MMAF, wherein the wavy line indicates the covalent attachment to a linker (L) of an antibody drug conjugate (US 2005/023 8649):

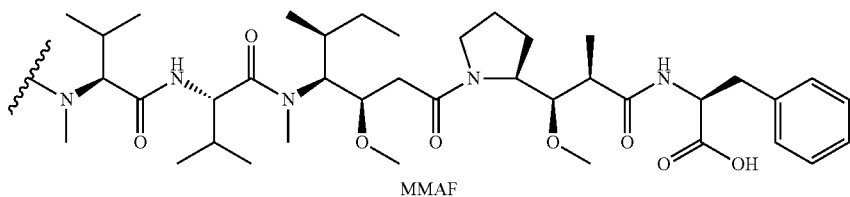
MMAF

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the

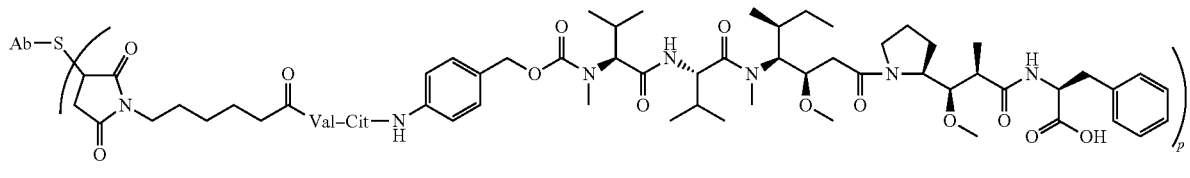
Ab-MC-vc-PAB-MMAF

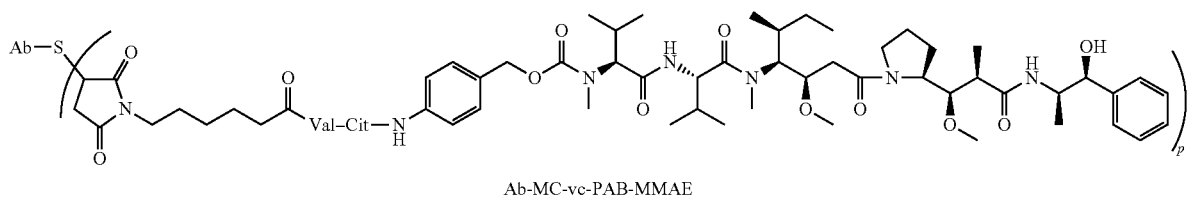
Ab-MC-vc-PAB-MMAE

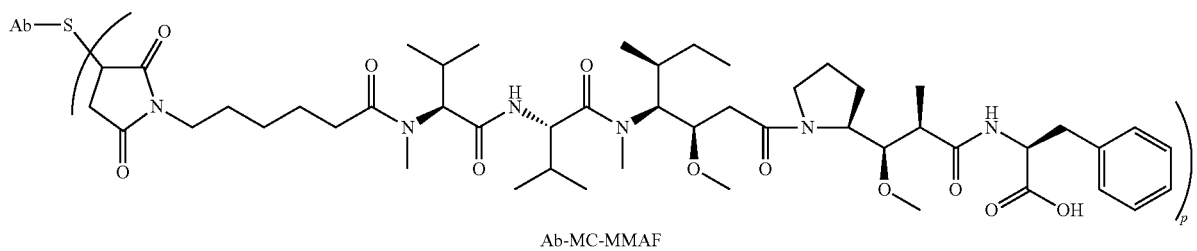
Ab-MC-MMAF methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

III(C). Calicheamicin

In other embodiments, the ADC comprises an antibody of the invention conjugated to one or more calicheamicin molecules. The calicheamicin families of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

III(D). Other Cytotoxic Agents

Other antitumor agents that can be conjugated to the antibodies of the invention include in some embodiments BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 (published Oct. 28, 1993).

The present invention in some embodiments further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

IV.) Antibody-Drug Conjugate Compounds which Bind CD37

The present invention provides, inter alia, antibody-drug conjugate compounds for targeted delivery of drugs. The inventors have made the discovery that the antibody-drug conjugate compounds have potent cytotoxic and/or cytostatic activity against cells expressing CD37. The antibody-drug conjugate compounds comprise an Antibody unit covalently linked to at least one Drug unit. The Drug units can be covalently linked directly or via a Linker unit (-LU-).

In some embodiments, the antibody drug conjugate compound has the following formula:

$$L\text{-}(LU\text{-}D)_p \qquad (I)$$

or a pharmaceutically acceptable salt or solvate thereof; wherein:
  L is the Antibody unit, e.g., a CD37 MAb of the present invention, and
  (LU-D) is a Linker unit-Drug unit moiety, wherein:
  LU- is a Linker unit, and
  D is a drug unit having cytostatic or cytotoxic activity against a target cell; and
  p is an integer from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4.

In some embodiments, the antibody drug conjugate compound has the following formula:

$$L\text{-}(A_a\text{-}W_w\text{—}Y_y\text{-}D)_p \qquad (II)$$

or a pharmaceutically acceptable salt or solvate thereof, wherein:
  L is the Antibody unit, e.g., CD37 MAb; and
  -$A_a$-$W_w$—$Y_y$— is a Linker unit (LU), wherein:
  -A- is a Stretcher unit,
  a is 0 or 1,
  each —W— is independently an Amino Acid unit,
  w is an integer ranging from 0 to 12,
  —Y— is a self-immolative spacer unit,
  y is 0, 1 or 2;
  D is a drug units having cytostatic or cytotoxic activity against the target cell; and
  p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined. In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise CD37 MAb as the Antibody unit, a drug, and optionally a linker that joins the drug and the binding agent. In a preferred embodiment, the Antibody is CD37 MAb comprising heavy and light chain variable regions of an antibody designated HvCD37-6b15.1.1 described above. In more preferred embodiment, the Antibody is CD37 MAb comprising heavy and light chain of an antibody designated HvCD37-6b15.1.1 described above. A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the CD37 MAb under appropriate conditions.

Each of the particular units of the Antibody-drug conjugate compounds is described in more detail herein. The synthesis and structure of exemplary Linker units, Stretcher units, Amino Acid units, self-immolative Spacer unit, and Drug units are also described in U.S. Patent Application Publication Nos. 2003/0083263, 2005/0238649 and 2005/0009751, each if which is incorporated herein by reference in its entirety and for all purposes.

V.) Linker Units

Typically, the antibody-drug conjugate compounds comprise a Linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in CD37-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 13)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein). In yet other embodiments, the linker promotes cellular internalization when conjugated to both the auristatin compound and the CD37 MAb.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

A "Linker unit" (LU) is a bifunctional compound that can be used to link a Drug unit and a Antibody unit to form an antibody-drug conjugate compound. In some embodiments, the Linker unit has the formula:

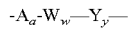

wherein: -A- is a Stretcher unit,
a is 0 or 1,
each —W— is independently an Amino Acid unit,
w is an integer ranging from 0 to 12,
—Y— is a self-immolative Spacer unit, and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

VI.) The Stretcher Unit

The Stretcher unit (A), when present, is capable of linking an Antibody unit to an Amino Acid unit (—W—), if present, to a Spacer unit (—Y—), if present; or to a Drug unit (-D). Useful functional groups that can be present on a CD37 MAb (e.g. HvCD37-6b15.1.1), either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of a CD37 MAb. In another embodiment, sulfhydryl groups can be generated by reaction of an amino group of a lysine moiety of a CD37 MAb with 2-iminothiolane (Traut's reagent) or other sulfhydryl generating reagents. In certain embodiments, the CD37 MAb is a recombinant antibody and is engineered to carry one or more lysines. In certain other embodiments, the recombinant CD37 MAb is engineered to carry additional sulfhydryl groups, e.g., additional cysteines.

In one embodiment, the Stretcher unit forms a bond with a sulfur atom of the Antibody unit. The sulfur atom can be derived from a sulfhydryl group of an antibody. Representative Stretcher units of this embodiment are depicted within the square brackets of Formulas IIIa and IIIb, wherein L-, —W—, —Y—, -D, w and y are as defined above, and $R^{17}$ is selected from —$C_1$-$C_{10}$ alkylene-, —$C_1$-$C_{10}$ alkenylene-, —$C_1$-$C_{10}$ alkynylene-, carbocyclo-, —O—($C_1$-$C_8$ alkylene)-, O—($C_1$-$C_8$ alkenylene)-, —O—($C_1$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, -arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —$(CH_2CH_2O)_r$—, or —$(CH_2CH_2O)_r$—$CH_2$—, and r is an integer ranging from 1-10, wherein said alkyl, alkenyl, alkynyl, alkylene, alkenylene, alkynylene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynyklene, aryl, carbocyle, carbocyclo, heterocyclo, and arylene radicals, whether alone or as part of another group, are unsubstituted. In some embodiments, $R^{17}$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, —$C_1$-$C_{10}$ alkylene-(heterocyclo)-, -(heterocyclo)-$C_1$-$C_{10}$ alkylene-, —$(CH_2CH_2O)_r$—, and —$(CH_2CH_2O)_r$—$CH_2$—; and r is an integer ranging from 1-10, wherein said alkylene groups are unsubstituted and the remainder of the groups are optionally substituted.

It is to be understood from all the exemplary embodiments that even where not denoted expressly, from 1 to 20 drug moieties can be linked to an Antibody (p=1-20).

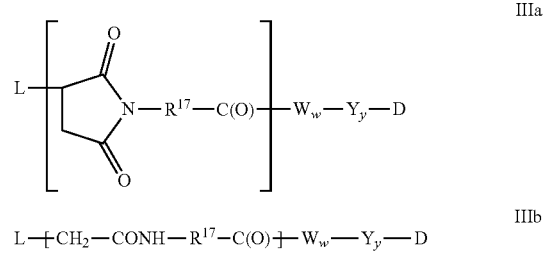

An illustrative Stretcher unit is that of Formula IIIa wherein $R^{17}$ is —$(CH_2)_5$—:

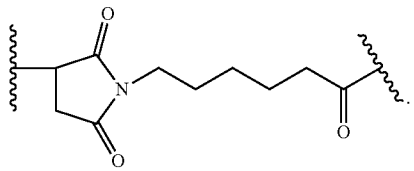 [SMILES: *C(=O)CCCCCN1C(=O)CC(*)C1=O]

Another illustrative Stretcher unit is that of Formula IIIa wherein $R^{17}$ is —(CH$_2$CH$_2$O)$_r$—CH$_2$—; and r is 2:

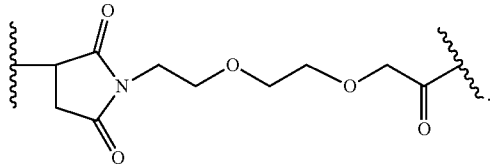 [SMILES: *C(=O)COCCOCCN1C(=O)CC(*)C1=O]

An illustrative Stretcher unit is that of Formula IIIa wherein $R^{17}$ is arylene- or arylene-C$_1$-C$_{10}$ alkylene-. In some embodiments, the aryl group is an unsubstituted phenyl group.

Still another illustrative Stretcher unit is that of Formula IIIb wherein $R^{17}$ is —(CH$_2$)$_5$—:

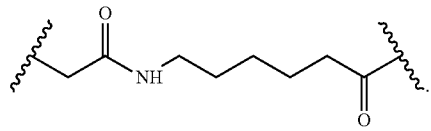 [SMILES: *CC(=O)NCCCCCC(*)=O]

In certain embodiments, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, L-, —W—, —Y—, -D, w and y are as defined above.

L-S-[-S—R$^{17}$—C(O)-]-W$_w$—Y$_y$-D    IV

It should be noted that throughout this application, the S moiety in the formula below refers to a sulfur atom of the Antibody unit, unless otherwise indicated by context.

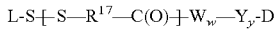

In yet other embodiments, the Stretcher contains a reactive site that can form a bond with a primary or secondary amino group of an Antibody. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —R$^{17}$—, L-, —W—, —Y—, -D, w and y are as defined above;

L-[-C(O)NH—R$^{17}$—C(O)-]-W$_w$—Y$_y$-D    Va

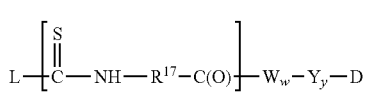
Vb

In some embodiments, the Stretcher contains a reactive site that is reactive to a modified carbohydrate's (—CHO) group that can be present on an Antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc, wherein —R$^{17}$—, L-, —W—, —Y—, -D, w and y are as defined as above.

L=[N—NH—R$^{17}$—C(O)-]-W$_w$—Y$_y$—D    VIa

L=[N—O—R$^{17}$—C(O)-]-W$_w$—Y$_y$—D    VIb

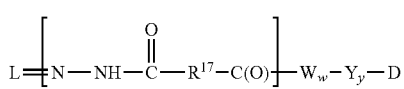
VIc

VII.) The Amino Acid Unit

The Amino Acid unit (—W—), when present, links the Stretcher unit to the Spacer unit if the Spacer unit is present, links the Stretcher unit to the Drug moiety if the Spacer unit is absent, and links the Antibody unit to the Drug unit if the Stretcher unit and Spacer unit are absent.

W$_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

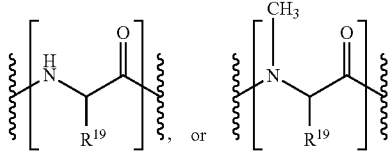

wherein $R^{19}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

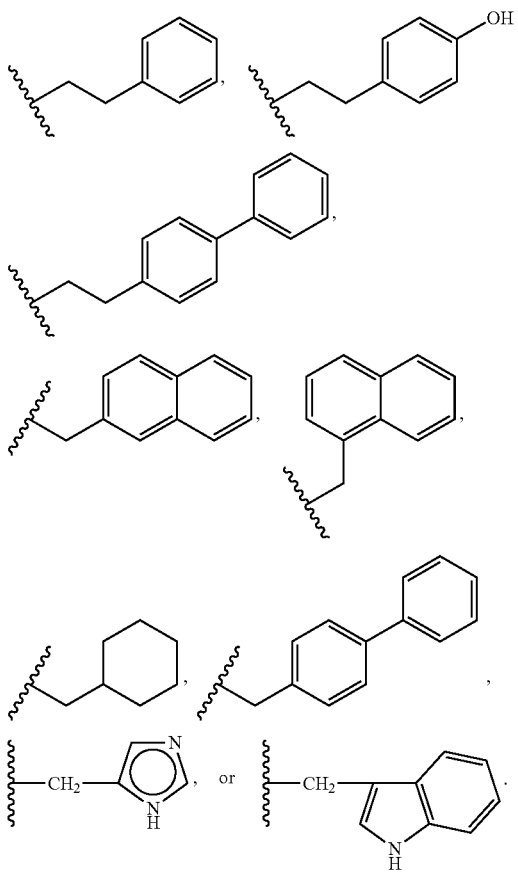

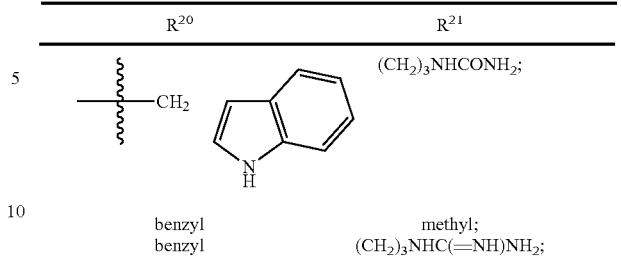

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative $W_w$ units are represented by formulas (VII)-(IX):

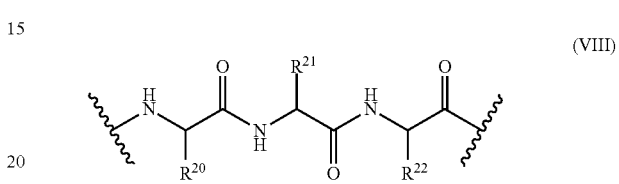

wherein $R^{20}$ and $R^{21}$ are as follows:

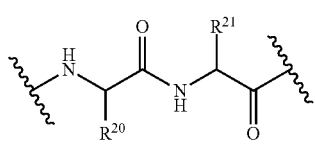

| $R^{20}$ | $R^{21}$ |
| --- | --- |
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |

-continued

| $R^{20}$ | $R^{21}$ |
| --- | --- |
| 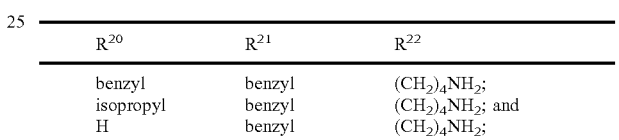 | $(CH_2)_3NHCONH_2$; |
| benzyl | methyl; |
| benzyl | $(CH_2)_3NHC(=NH)NH_2$; |

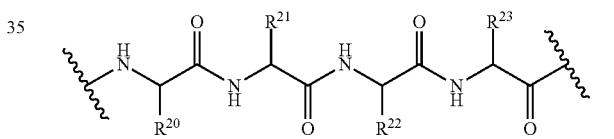

wherein $R^{20}$, $R^{21}$ and $R^{22}$ are as follows:

| $R^{20}$ | $R^{21}$ | $R^{22}$ |
| --- | --- | --- |
| benzyl | benzyl | $(CH_2)_4NH_2$; |
| isopropyl | benzyl | $(CH_2)_4NH_2$; and |
| H | benzyl | $(CH_2)_4NH_2$; |

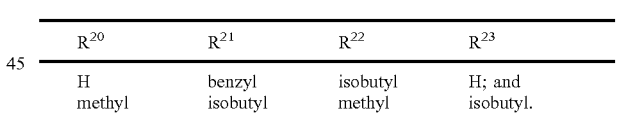

wherein $R^{20}$, $R^{21}$, $R^{22}$ and $R^{23}$ are as follows:

| $R^{20}$ | $R^{21}$ | $R^{22}$ | $R^{23}$ |
| --- | --- | --- | --- |
| H | benzyl | isobutyl | H; and |
| methyl | isobutyl | methyl | isobutyl. |

Exemplary Amino Acid units include, but are not limited to, units of formula VII where: $R^{20}$ is benzyl and $R^{21}$ is —$(CH_2)_4NH_2$; $R^{20}$ is isopropyl and $R^{21}$ is —$(CH_2)_4NH_2$; or $R^{20}$ is isopropyl and $R^{21}$ is —$(CH_2)_3NHCONH_2$. Another exemplary Amino Acid unit is a unit of formula VIII wherein $R^{20}$ is benzyl, $R^{21}$ is benzyl, and $R^{22}$ is —$(CH_2)_4NH_2$.

Useful —$W_w$— units can be designed and optimized in their selectivity for enzymatic cleavage by a particular enzyme, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide. When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetrai soquinolinecarboxylate lysine, cyclohexylalanine lysine, isonepecotic acid lysine, beta-alanine lysine, glycine serine valine glutamine and isonepecotic acid.

VIII.) The Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the antibody-drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

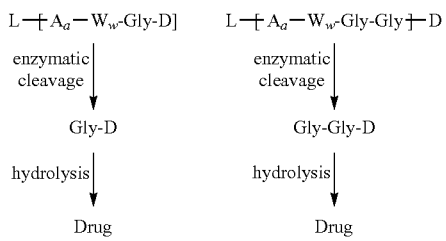

In some embodiments, a non self-immolative Spacer unit (—Y—) is -Gly-. In some embodiments, a non self-immolative Spacer unit (—Y—) is -Gly-Gly-.

In one embodiment, a Drug-Linker conjugate is provided in which the Spacer unit is absent (y=0), or a pharmaceutically acceptable salt or solvate thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit (see Schemes 2 and 3) whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Toki et al., 2002, *J. Org. Chem.* 67:1866-1872.

Scheme 2

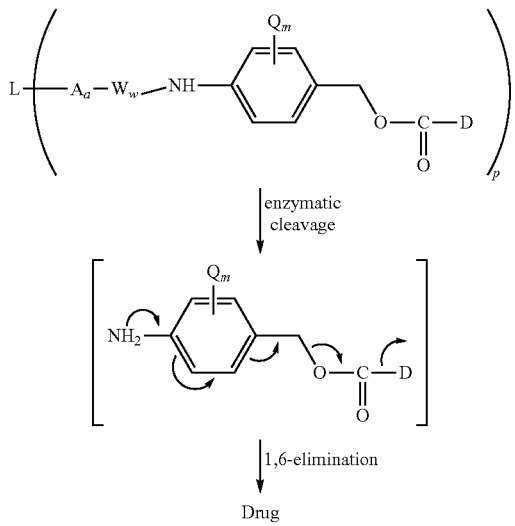

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

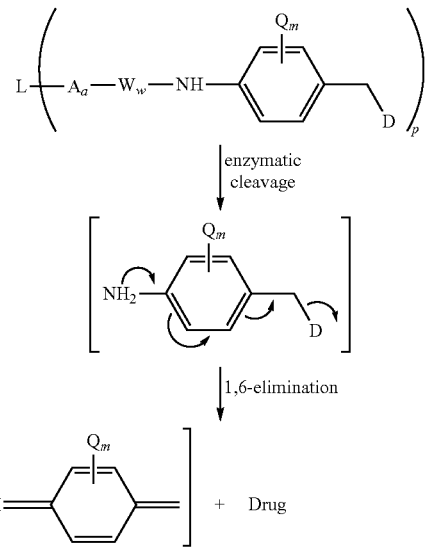

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacers.

In one embodiment, the Spacer unit is a branched bis(hydroxymethyl)-styrene (BHMS) unit as depicted in Scheme 4, which can be used to incorporate and release multiple drugs.

Scheme 4

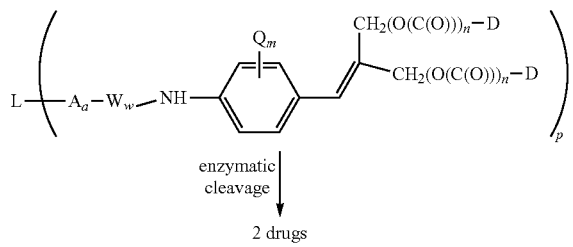

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges raging from 1 to about 20. The alkyl, alkenyl and alkynyl groups, whether alone or as part of another group, can be optionally substituted.

In some embodiments, the -D moieties are the same. In yet another embodiment, the -D moieties are different.

In one aspect, Spacer units (—$Y_y$—) are represented by Formulas (X)-(XII):

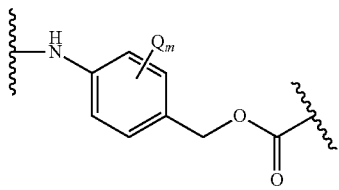

X wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

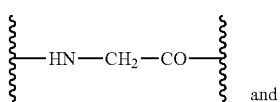

XI and

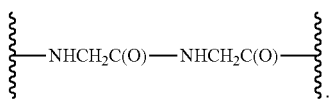

XII

Embodiments of the Formula I and II comprising antibody-drug conjugate compounds can include:

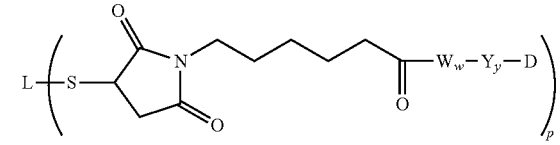

wherein w and y are each 0, 1 or 2, and,

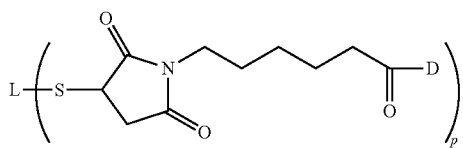

wherein w and y are each 0,

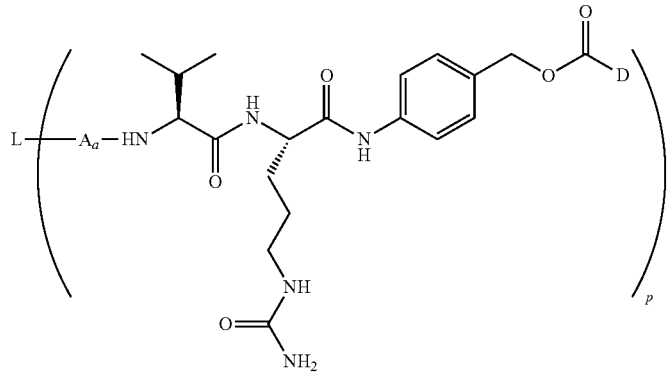

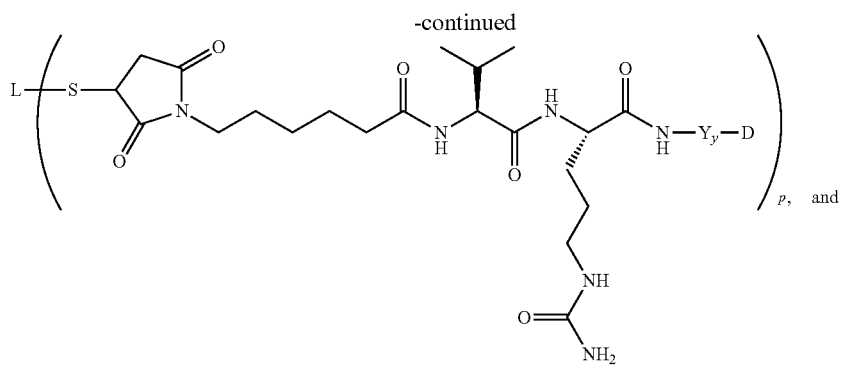

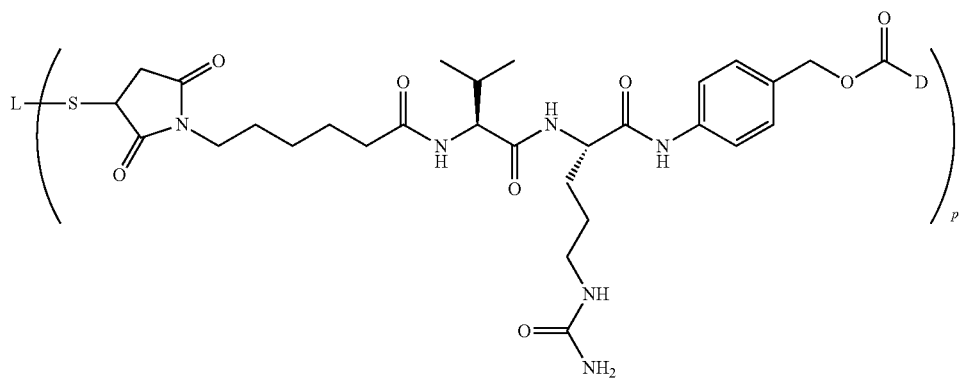

IX.) The Drug Unit

The Drug moiety (D) can be any cytotoxic, cytostatic or immunomodulatory (e.g., immunosuppressive) or drug. D is a Drug unit (moiety) having an atom that can form a bond with the Spacer unit, with the Amino Acid unit, with the Stretcher unit or with the Antibody unit. In some embodiments, the Drug unit D has a nitrogen atom that can form a bond with the Spacer unit. As used herein, the terms "Drug unit" and "Drug moiety" are synonymous and used interchangeably.

Useful classes of cytotoxic or immunomodulatory agents include, for example, antitubulin agents, DNA minor groove binders, DNA replication inhibitors, and alkylating agents.

In some embodiments, the Drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

Auristatins have been shown to interfere with microtubule dynamics and nuclear and cellular division and have anti-cancer activity. Auristatins bind tubulin and can exert a cytotoxic or cytostatic effect on a CD37-expressing cell. There are a number of different assays, known in the art, which can be used for determining whether an auristatin or resultant antibody-drug conjugate exerts a cytostatic or cytotoxic effect on a desired cell line.

Methods for determining whether a compound binds tubulin are known in the art. See, for example, Muller et al., *Anal. Chem* 2006, 78, 4390-4397; Hamel et al., *Molecular Pharmacology*, 1995 47: 965-976; and Hamel et al., *The Journal of Biological Chemistry*, 1990 265:28, 17141-17149. For purposes of the present invention, the relative affinity of a compound to tubulin can be determined. Some preferred auristatins of the present invention bind tubulin with an affinity ranging from 10 fold lower (weaker affinity) than the binding affinity of MMAE to tubulin to 10 fold, 20 fold or even 100 fold higher (higher affinity) than the binding affinity of MMAE to tublin.

In some embodiments, -D is an auristatin of the formula $D_E$ or $D_F$:

$D_E$

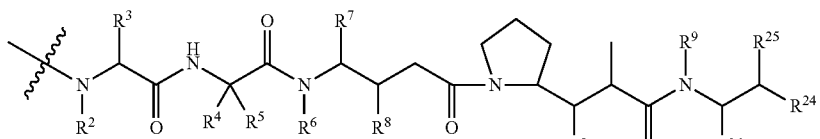

$D_F$

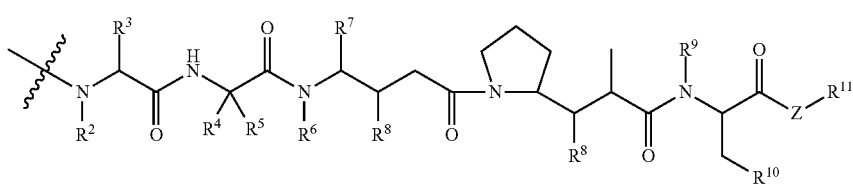

or a pharmaceutically acceptable salt or solvate form thereof;

wherein, independently at each location:

the wavy line indicates a bond;

$R^2$ is —$C_1$-$C_{20}$ alkyl, —$C_2$-$C_{20}$ alkenyl, or —$C_2$-$C_{20}$ alkynyl;

$R^3$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene (aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene (aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or -carbocycle and s is 2, 3, 4, 5 or 6, $R^6$ is —H, —$C_1$-$C_{20}$ alkyl, —$C_2$-$C_{20}$ alkenyl, or —$C_2$-$C_{20}$ alkynyl;

$R^7$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene (aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;

$R^9$ is —H, —$C_1$-$C_{20}$ alkyl, —$C_2$-$C_{20}$ alkenyl, or —$C_2$-$C_{20}$ alkynyl;

$R^{24}$ is -aryl, -heterocycle, or -carbocycle;

$R^{25}$ is —H, $C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^8$ represents =O;

$R^{26}$ is —H, —$C_1$-$C_{20}$ alkyl, —$C_2$-$C_{20}$ alkenyl, or —$C_2$-$C_{20}$ alkynyl, -aryl, -heterocycle, or -carbocycle;

$R^{10}$ is -aryl or -heterocycle;

Z is —O, —S, —NH, or —$NR^{12}$, wherein $R^{12}$ is —$C_1$-$C_{20}$ alkyl, —$C_2$-$C_{20}$ alkenyl, or —$C_2$-$C_{20}$ alkynyl;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$;

m is an integer ranging from 1-1000;

$R^{13}$ is —$C_2$-$C_{20}$ alkylene, —$C_2$-$C_{20}$ alkenylene, or —$C_2$-$C_{20}$ alkynylene;

$R^{14}$ is —H, —$C_1$-$C_{20}$ alkyl, —$C_2$-$C_{20}$ alkenyl, or —$C_2$-$C_{20}$ alkynyl;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH; and n is an integer ranging from 0 to 6;

wherein said alkyl, alkenyl, alkynyl, alkylene, alkenylene, alkynyklene, aryl, carbocyle, and heterocycle radicals, whether alone or as part of another group, are optionally substituted.

Auristatins of the formula $D_E$ include those wherein said alkyl, alkenyl, alkynyl, alkylene, alkenylene, alkynyklene, aryl, carbocyle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula $D_E$ include those wherein $R^2$ is $C_1$-$C_8$ alkyl;

$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, alkynylene, carbocycle, aryl and heterocycle radicals are optionally substituted;

$R^5$ is —H;

$R^6$ is —$C_1$-$C_8$ alkyl;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted;

$R^9$ is —H or —$C_1$-$C_8$ alkyl;
$R^{24}$ is optionally substituted -phenyl;
$R^{25}$ is —$OR^{18}$; wherein $R^{18}$ is H, a hydroxyl protecting group, or a direct bond where $OR^{18}$ represents =O;
$R^{26}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, alkynyl and carbocycle radicals are optionally substituted; or a pharmaceutically acceptable salt or solvate form thereof.

Auristatins of the formula $D_E$ include those wherein
$R^2$ is methyl;
$R^3$ is —H, —$C_1$-$C_8$ alkyl, —$C_2$-$C_8$ alkenyl, or $C_2$-$C_8$ alkynyl, wherein said alkyl, alkenyl and alkynyl radicals are optionally substituted;
$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, alkynylene, aryl and carbocycle radicals whether alone or as part of another group are optionally substituted;
$R^5$ is —H;
$R^6$ is methyl;
$R^7$ is —$C_1$-$C_8$ alkyl, —$C_2$-$C_8$ alkenyl or —$C_2$-$C_8$ alkynyl;
each $R^8$ is methoxy;
$R^9$ is —H or —$C_1$-$C_8$ alkyl;
$R^{24}$ is -phenyl;
$R^{25}$ is —$OR^{18}$; wherein $R^{18}$ is H, a hydroxyl protecting group, or a direct bond where OR18 represents =O;
$R^{26}$ is methyl;
or a pharmaceutically acceptable salt form thereof.

Auristatins of the formula $D_E$ include those wherein:
$R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{24}$ is phenyl; $R^{25}$ is —$OR^{18}$; wherein $R^{18}$ is —H, a hydroxyl protecting group, or a direct bond where $OR^{18}$ represents =O; and $R^{26}$ is methyl; or a pharmaceutically acceptable salt or solvate form thereof.

Auristatins of the formula DE include those wherein:
$R^2$ is methyl or $C_1$-$C_3$ alkyl,
$R^3$ is —H or —$C_1$-$C_3$ alkyl;
$R^4$ is —$C_1$-$C_5$ alkyl;
$R^5$ is H;
$R^6$ is C1-C3 alkyl;
$R^7$ is —$C_1$-$C_5$ alkyl;
$R^8$ is —$C_1$-$C_3$ alkoxy;
$R^9$ is —H or —$C_1$-$C_8$ alkyl;
$R^{24}$ is phenyl;
$R^{25}$ is —$OR^{18}$; wherein $R^{18}$ is —H, a hydroxyl protecting group, or a direct bond where $OR^{18}$ represents =O; and
$R^{26}$ is —$C_1$-$C_3$ alkyl;
or a pharmaceutically acceptable salt form thereof.

Auristatins of the formula $D_F$ include those wherein
$R^2$ is methyl;
$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene ($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocycle, aryl and heterocycle radicals whether alone or as part of another group are optionally substituted;
$R^5$ is —H;
$R^6$ is methyl;
each $R^8$ is methoxy;
$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted;
$R^{10}$ is optionally substituted aryl or optionally substituted heterocycle;
Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl, each of which is optionally substituted;
$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$, wherein said alkyl, alkenyl, alkynyl, aryl and heterocycle radicals are optionally substituted;
m is an integer ranging from 1-1000 or m=0;
$R^{13}$ is —$C_2$-$C_{20}$ alkylene, —$C_2$-$C_{20}$ alkenylene, or —$C_2$-$C_{20}$ alkynylene, each of which is optionally substituted;
$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted;
each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted;
each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted;
n is an integer ranging from 0 to 6;
or a pharmaceutically acceptable salt thereof.

In certain of these embodiments, $R^{10}$ is optionally substituted phenyl.

Auristatins of the formula $D_F$ include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocyle, and heterocycle radicals are unsubstituted.

Auristatins of the formula $D_F$ include those wherein
$R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is optionally substituted phenyl; Z is —O—, —S—, or —NH—; $R^{11}$ is as defined herein; or a pharmaceutically acceptable salt thereof.

Auristatins of the formula $D_F$ include those wherein
$R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{10}$ is optionally substituted phenyl; Z is —O—, —S—, or —NH—; and R" is as defined herein; or a pharmaceutically acceptable salt thereof.

Auristatins of the formula $D_F$ include those wherein
$R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or $C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_F$ include those wherein $R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_E$ or $D_F$ include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainders of the substituents are as defined herein.

Auristatins of the formula $D_E$ or $D_F$ include those wherein $R^2$ and $R^6$ are each methyl, and $R^9$ is H. The remainder of the substituents are as defined herein.

Auristatins of the formula $D_E$ or $D_F$ include those wherein each occurrence of $R^8$ is —$OCH_3$. The remainder of the substituents are as defined herein.

Auristatins of the formula DE or DF include those wherein $R^3$ and $R^4$ are each isopropyl, R2 and R6 are each methyl, R5 is H, R7 is sec-butyl, each occurrence of R8 is —OCH3, and R9 is H. The remainder of the substituents are as defined herein.

Auristatins of the formula DF include those wherein Z is —O— or —NH—. The remainder of the substituents are as defined herein.

Auristatins of the formula DF include those wherein R10 is aryl. The remainder of the substituents are as defined herein.

Auristatins of the formula DF include those wherein R10 is -phenyl. The remainder of the substituents are as defined herein.

Auristatins of the formula DF include those wherein Z is —O—, and R11 is H, methyl or t-butyl. The remainder of the substituents are as defined herein.

Auristatins of the formula DF include those wherein, when Z is —NH—, R11 is —(R13O)m-CH(R15)2, wherein R15 is —(CH2)n-N(R16)2, and R16 is -C1-C8 alkyl or —(CH2)n-COOH. The remainder of the substituents are as defined herein.

Auristatins of the formula DF include those wherein when Z is —NH—, R11 is —(R13O)m-CH(R15)2, wherein R15 is —(CH2)n-SO3H. The remainder of the substituents are as defined herein.

In preferred embodiments, when D is an auristatin of formula DE, w is an integer ranging from 1 to 12, preferably 2 to 12, y is 1 or 2, and a is preferably 1.

In some embodiments, wherein D is an auristatin of formula DF, a is 1 and w and y are 0.

Illustrative Drug units (-D) include the drug units having the following structures:

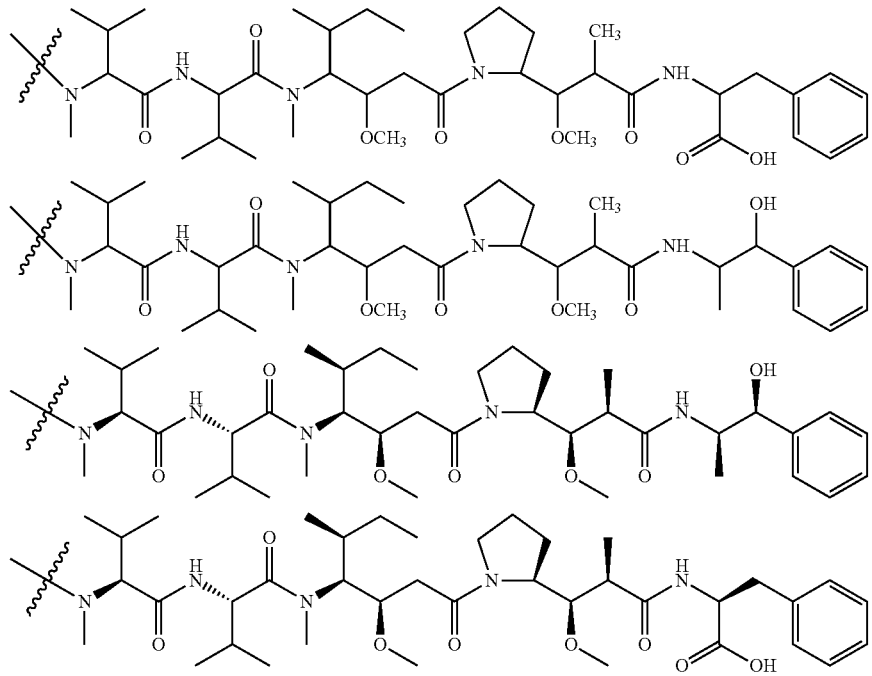

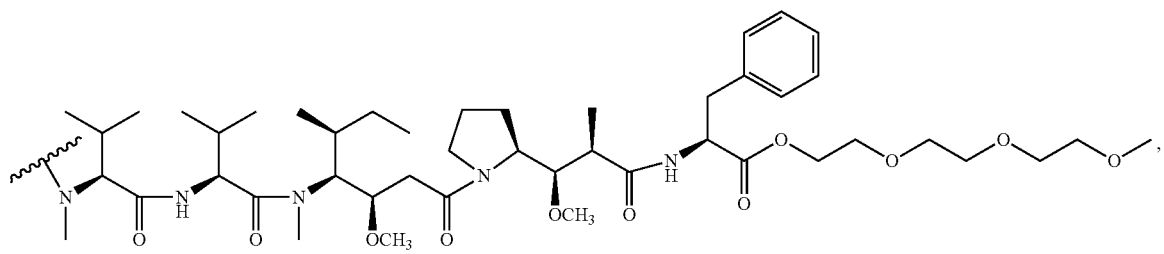

-continued
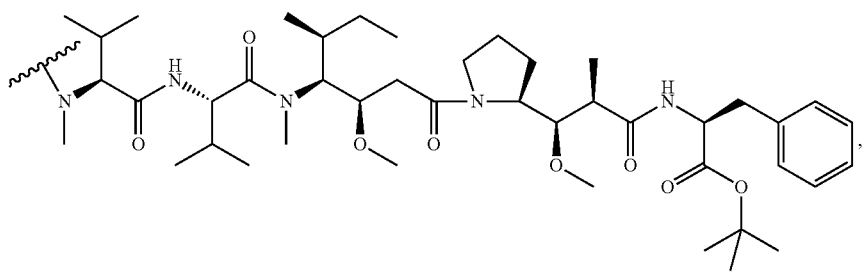
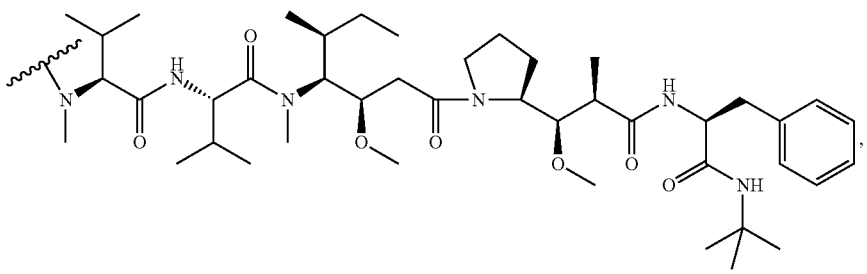
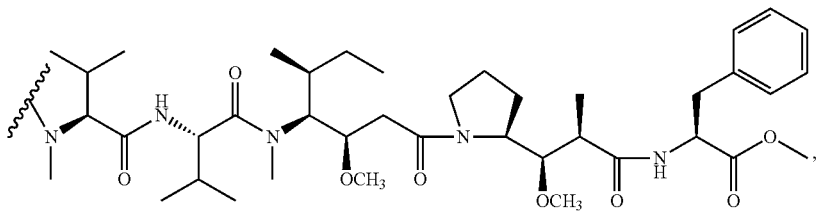
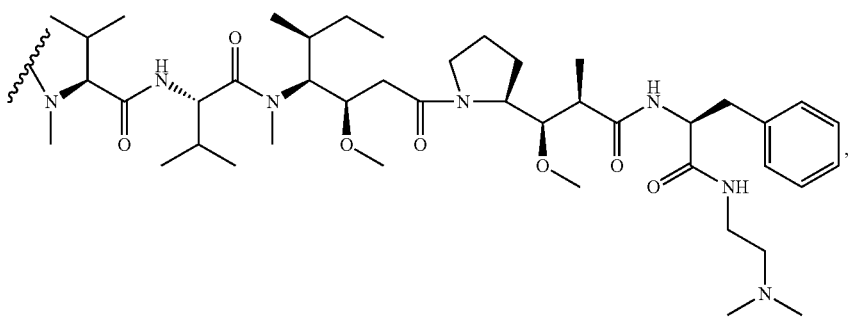
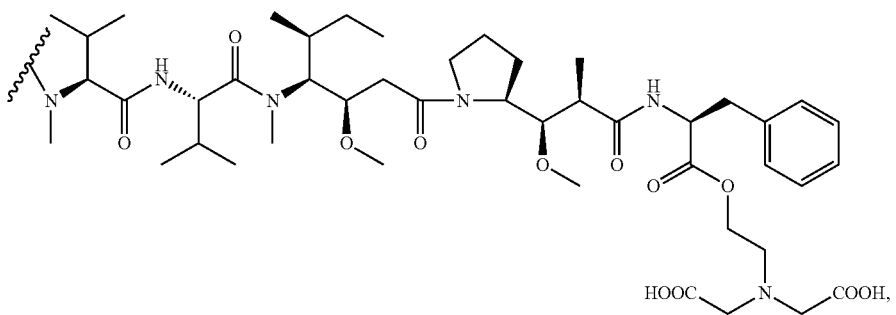
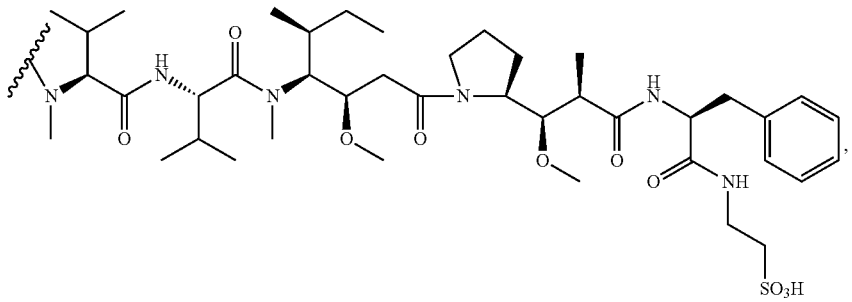

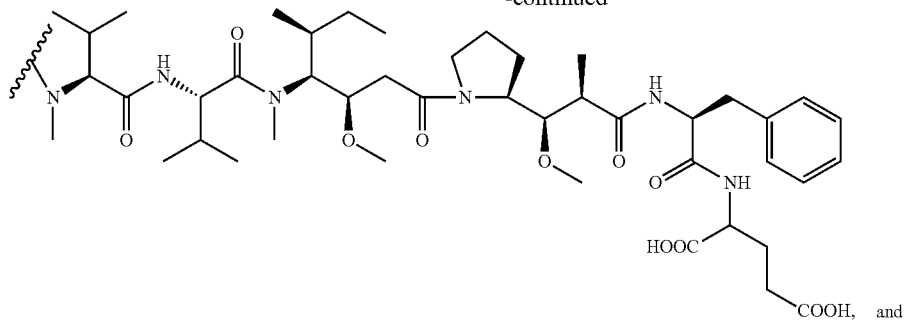

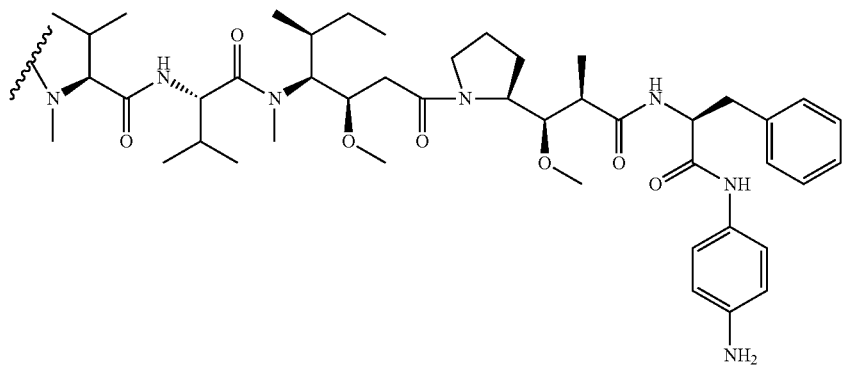

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug Unit.

In some embodiments, the Drug unit is not TZT-1027. In some embodiments, the Drug unit is not auristatin E, dolastatin 10, or auristatin PE.

Exemplary antibody-drug conjugate compounds have the following structures wherein "L" or "mAb-s-" represents a CD37 MAb designated HvCD37-6b15.1.1 set forth herein:

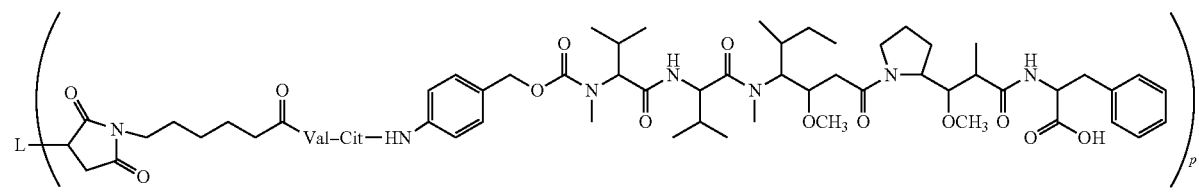

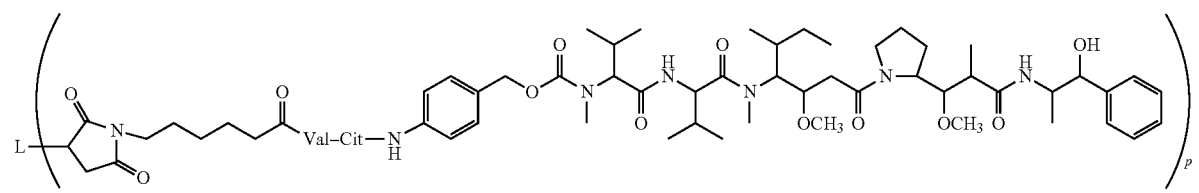

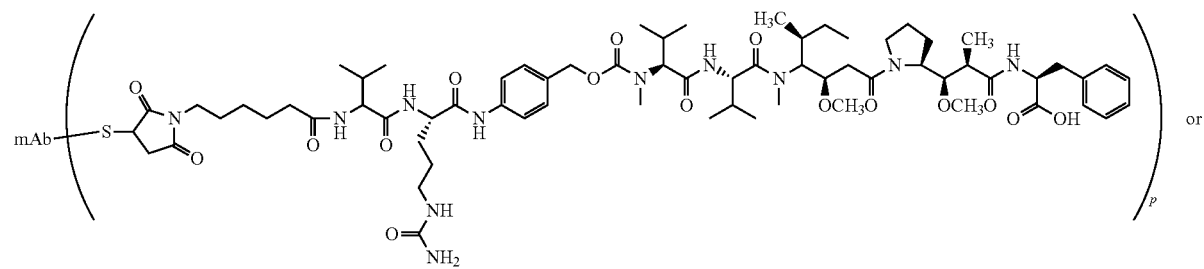

L-MC-vc-PAB-MMAP

L-MC-vc-PAB-MMAE. or

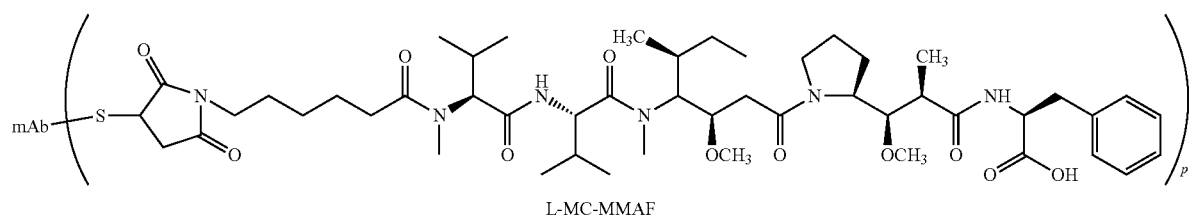

L-MC-MMAF or pharmaceutically acceptable salt thereof.

In some embodiments, the Drug Unit is a calicheamicin, camptothecin, a maytansinoid, or an anthracycline. In some embodiments the drug is a taxane, a topoisomerase inhibitor, a vinca alkaloid, or the like.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, and vinca alkaloids. Other cytotoxic agents include, for example, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug is an anti-tubulin agent. Examples of anti-tubulin agents include, auristatins, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent is a dolastatin. In certain embodiments, the cytotoxic or cytostatic agent is of the auristatin class. Thus, in a specific embodiment, the cytotoxic or cytostatic agent is MMAE (Formula XI). In another specific embodiment, the cytotoxic or cytostatic agent is AFP (Formula XVI).

(XI)

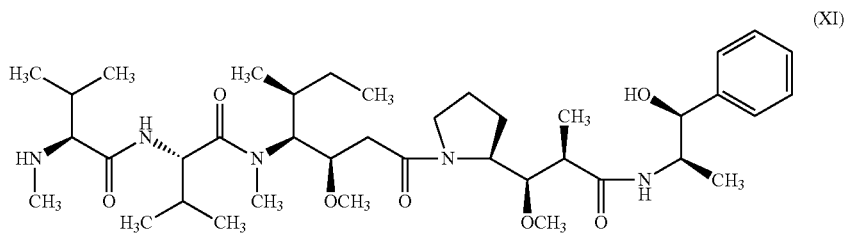 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In certain embodiments, the cytotoxic or cytostatic agent is a compound of formulas XII-XXI or pharmaceutically acceptable salt thereof:

(XII)

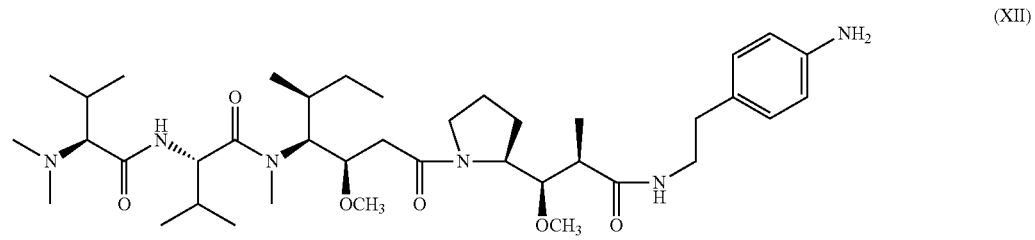

(XIII)

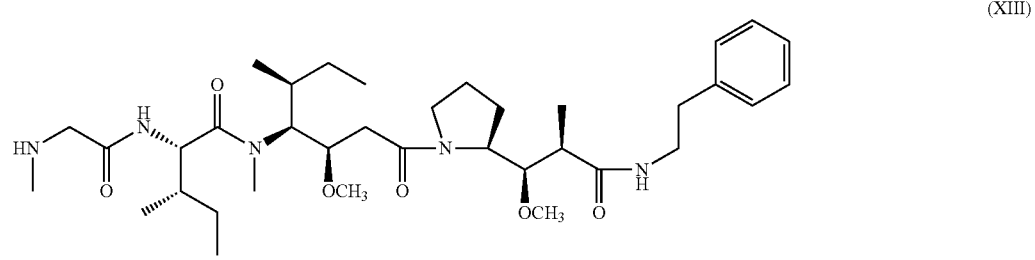

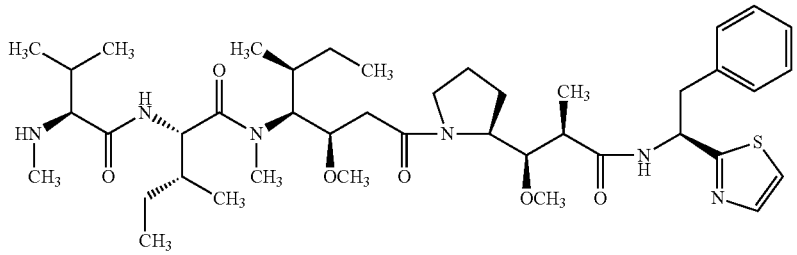
(XIV)
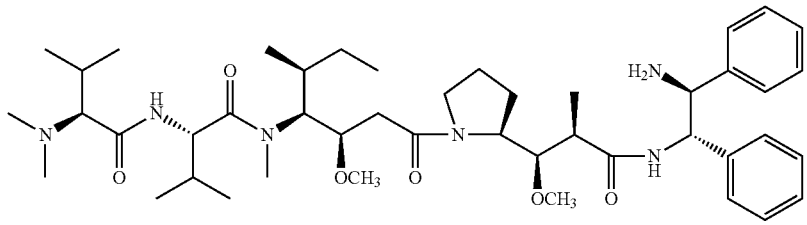
(XV)
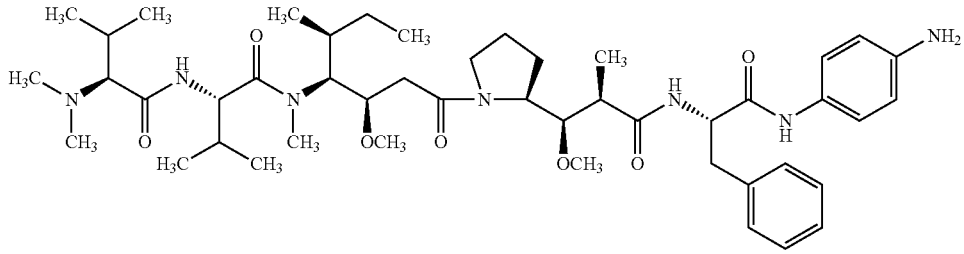
(XVI)
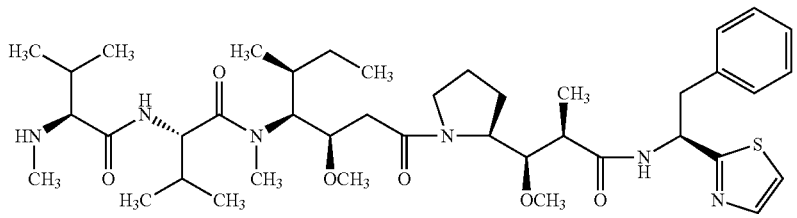
(XVII)
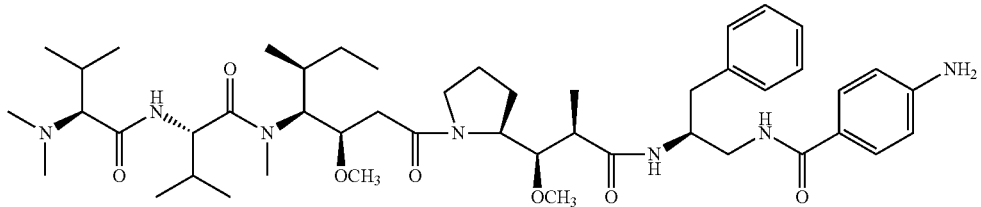
(XVIII)
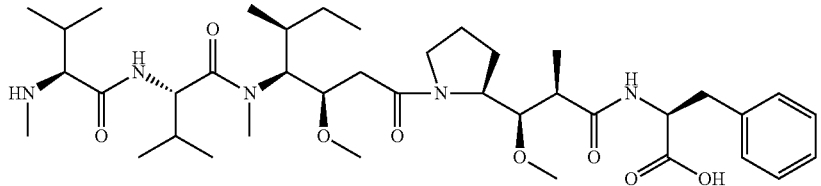
(XVIX)

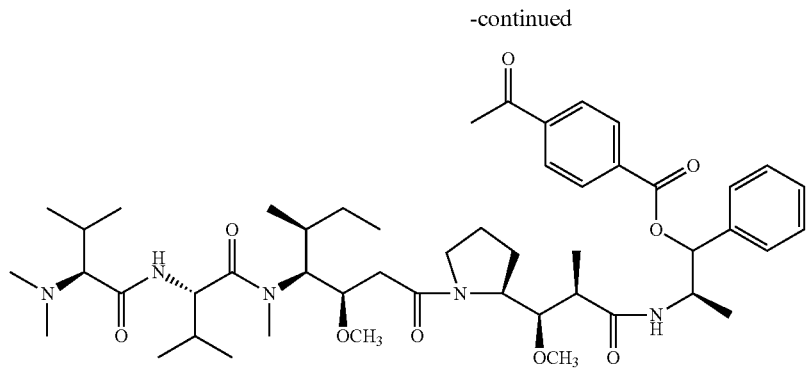

(XX)

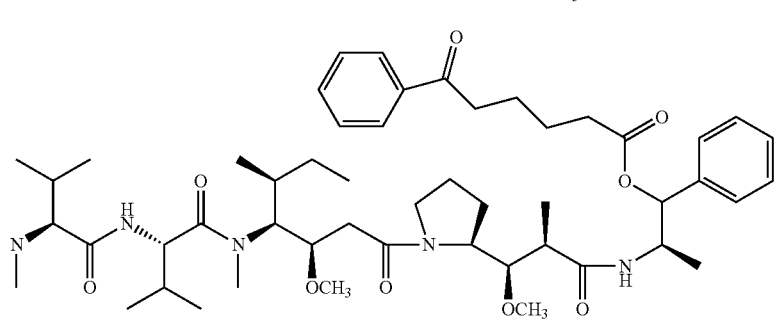

(XXI)

X.) Drug Loading

Drug loading is represented by p and is the average number of Drug moieties per antibody in a molecule. Drug loading may range from 1 to 20 drug moieties (D) per antibody. ADCs of the invention in some embodiments include collections of antibodies conjugated with a range of drug moieties, from 1 to 20. The average number of drug moieties per antibody in preparations of ADC from conjugation reactions may be characterized by conventional means such as mass spectroscopy and, ELISA assay. The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

XI.) Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that a Antibody Drug conjugate is useful in the treatment of cancers.

Cell viability can be measured by determining in a cell the uptake of a dye such as neutral red, trypan blue, or ALAMAR™ blue (see, e.g., Page et al., 1993, *Intl. J. Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Natl. Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

In vivo, the effect of a CD37 therapeutic composition can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

In one embodiment, the pharmaceutical composition of the present invention may comprise more than one species of ADC of the invention due to modification of HvCD37-6b15.1.1 MAb. For example, the present invention includes a pharmaceutical composition comprising the ADC of the invention, wherein the HvCD37-6b15.1.1 MAb is an antibody lacking heavy chain C-terminal lysine, an antibody having N-terminal post-translational modification, an antibody lacking heavy chain C-terminal lysine and having N-terminal post-translational modification, and/or an antibody having heavy chain C-terminal lysine and not having N-terminal post-translational modification.

For example, an pharmaceutical composition of the present invention in some embodiments includes an pharmaceutical composition comprising two or more species of the ADC of the invention, wherein HvCD37-6b15.1.1 MAb of the ADC is selected from the group of the following 1) to 4):

1) HvCD37-6b15.1.1 MAb comprising a heavy chain consisting of the amino acid sequence ranging from residue 1 (Q) to residue 441 (K) of SEQ ID NO: 7 and a light chain consisting of the amino acid sequence ranging from residue 1 (D) to residue 212 (C) of SEQ ID NO: 8;
2) HvCD37-6b15.1.1 MAb comprising a heavy chain consisting of the amino acid sequence ranging from residue 1 (Q) to residue 441 (K) of SEQ ID NO: 7 wherein the N-terminal residue 1 (Q) is converted to pyroglutamic acid and a light chain consisting of the amino acid sequence ranging from residue 1 (D) to residue 212 (C) of SEQ ID NO: 8;
3) HvCD37-6b15.1.1 MAb comprising a heavy chain consisting of the amino acid sequence ranging from residue 1 (Q) to residue 441 (K) of SEQ ID NO: 7 wherein the C-terminal residue 441 (K) is removed and a light chain consisting of the amino acid sequence ranging from residue 1 (D) to residue 212 (C) of SEQ ID NO: 8; and
4) HvCD37-6b15.1.1 MAb comprising a heavy chain consisting of the amino acid sequence ranging from residue 1 (Q) to residue 441 (K) of SEQ ID NO: 7 wherein the N-terminal residue 1 (Q) is converted to pyroglutamic acid and the C-terminal residue 441 (K) is removed and a light chain consisting of the amino acid sequence ranging from residue 1 (D) to residue 212 (C) of SEQ ID NO: 8.

XII.) Treatment of Cancer(s) Expressing CD37

The identification of CD37 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a CD37 protein are useful for patients suffering from a cancer that expresses CD37. These therapeutic approaches generally fall into three classes. The first class modulates CD37 function as it relates to tumor cell growth leading to inhibition or retardation of tumor cell growth or inducing its killing. The second class comprises various methods for inhibiting the binding or association of a CD37 protein with its binding partner or with other proteins. The third class comprises a variety of methods for inhibiting the transcription of a CD37 gene or translation of CD37 mRNA.

Accordingly, Cancer patients can be evaluated for the presence and level of CD37 expression, preferably using immunohistochemical assessments of tumor tissue, quantitative CD37 imaging, or other techniques that reliably indicate the presence and degree of CD37 expression. Immunohistochemical analysis of tumor biopsies or surgical specimens is preferred for this purpose. Methods for immunohistochemical analysis of tumor tissues are well known in the art.

XIII.) CD37 as a Target for Antibody-Based Therapy

CD37 is an attractive target for antibody-based therapeutic strategies. A number of antibody strategies are known in the art for targeting both extracellular and intracellular molecules (see, e.g., complement and ADCC mediated killing as well as the use of intrabodies). Because CD37 is expressed by cancer cells of various lineages relative to corresponding normal cells, systemic administration of CD37-immunoreactive compositions are prepared that exhibit excellent sensitivity without toxic, non-specific and/or non-target effects caused by binding of the immunoreactive composition to non-target organs and tissues. Antibodies specifically reactive with domains of CD37 are useful to treat CD37-expressing cancers systemically, preferably as antibody drug conjugates (i.e. ADCs) wherein the conjugate is with a toxin or therapeutic agent.

Those skilled in the art understand that antibodies can be used to specifically target and bind immunogenic molecules such as an immunogenic region of a CD37 sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. CD37), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an mammal having a tumor a biologically effective amount of a conjugate comprising a selected cytotoxic and/or therapeutic agent linked to a targeting agent (e.g. a CD37 MAb, preferably HvCD37-6b15.1.1) that binds to an antigen (e.g. CD37) expressed, accessible to binding or localized on the cell surfaces. A typical embodiment is a method of delivering a cytotoxic and/or therapeutic agent to a cell expressing CD37, comprising conjugating the cytotoxic agent to an antibody that immunospecifically binds to a CD37 epitope, and, exposing the cell to the antibody drug conjugate (ADC). Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using CD37 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). In a preferred embodiment, the antibodies will be conjugated a cytotoxic agent, supra, preferably an aurastatin derivative designated MMAE (Seattle Genetics).

Although CD37 antibody therapy is useful for all stages of cancer, antibody therapy can be particularly appropriate in advanced or metastatic cancers. Treatment with the antibody therapy of the invention in some embodiments is indicated for patients who have received one or more rounds of chemotherapy. Alternatively, antibody therapy of the invention in some embodiments is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

CD37 monoclonal antibodies that treat the cancers set forth in Table I include those that initiate a potent immune response against the tumor or those that are directly cytotoxic. In this regard, CD37 monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, CD37 MAbs that exert a direct biological effect on tumor growth are useful to treat cancers that express CD37. Mechanisms by which directly cytotoxic MAbs act include: inhibition of cell growth, modulation of cellular differentiation, modulation of tumor angiogenesis factor profiles, and the induction of apoptosis. The mechanism(s) by which a particular CD37 MAb exerts an anti-tumor effect is evaluated using any number of in vitro assays that evaluate cell death such as ADCC, complement-mediated cell lysis, and so forth, as is generally known in the art.

Accordingly, preferred monoclonal antibodies used in the therapeutic methods of the invention include those that are either fully human and that bind specifically to the target CD37 antigen with high affinity.

XIV.) CD37 ADC Cocktails

Therapeutic methods of the invention in some embodiments contemplate the administration of single CD37 ADCs as well as combinations, or cocktails, of different MAbs (i.e. CD37 MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, CD37 MAbs can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the CD37 MAbs are administered in conjugated form.

CD37 ADC formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the CD37 ADC preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of CD37 expression in the patient, the extent of circulating shed CD37 antigen, the desired steady-state antibody concentration level, frequency of treatment, and the influence of chemotherapeutic or other agents used in combination with the provided treatment methods, as well as the health status of a particular patient.

Optionally, patients should be evaluated for the levels of CD37 in a given sample (e.g. the levels of circulating CD37 antigen and/or CD37 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide CD37 ADCs, which inhibit or retard the growth of tumor cells expressing CD37. A further object of this invention is to provide methods to inhibit angiogenesis and other biological functions and thereby reduce tumor growth in mammals, preferably humans, using such CD37 ADCs, and in particular using such CD37 ADCs combined with other drugs or immunologically active treatments.

XV.) Combination Therapy

In one embodiment, there is synergy when tumors, including human tumors, are treated with CD37 ADCs in conjunction with chemotherapeutic agents or radiation or combinations thereof. In other words, the inhibition of tumor growth by a CD37 ADC is enhanced more than expected when combined with chemotherapeutic agents or radiation or combinations thereof. Synergy may be shown, for example, by greater inhibition of tumor growth with combined treatment than would be expected from a treatment of only CD37 ADC or the additive effect of treatment with a CD37 ADC and a chemotherapeutic agent or radiation. Preferably, synergy is demonstrated by remission of the cancer where remission is not expected from treatment either from a CD37 ADC or with treatment using an additive combination of a CD37 ADC and a chemotherapeutic agent or radiation.

The method for inhibiting growth of tumor cells using a CD37 ADC and a combination of chemotherapy or radiation or both comprises administering the CD37 ADC before, during, or after commencing chemotherapy or radiation therapy, as well as any combination thereof (i.e. before and during, before and after, during and after, or before, during, and after commencing the chemotherapy and/or radiation therapy). For example, the CD37 ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the CD37 ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a CD37 ADC, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention in some embodiments can enable the use of reduced dosages of chemotherapy (or other therapies) and/or less frequent administration, an advantage for all patients and particularly for those that do not tolerate the toxicity of the chemotherapeutic agent well.

XVI.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an antibody that is or can be detectably labeled. Kits can comprise a container comprising a Drug Unit. The kit can include all or part of the amino acid sequences in FIG. 2A or 2B, or FIG. 3A or 3B or analogs thereof, or a nucleic acid molecule that encodes such amino acid sequences.

A kit of the invention in some embodiments will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer of a tissue set forth in Table I.

The terms "kit" and "article of manufacture" can be used as synonyms.

In another embodiment of the invention, an article(s) of manufacture containing compositions, such as antibody(s), or antibody drug conjugates (ADCs) e.g., materials useful for the diagnosis, prognosis, prophylaxis and/or treatment of cancers of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In another embodiment a container comprises an antibody, binding fragment thereof or specific binding protein for use in evaluating protein expression of CD37 in cells and tissues, or for relevant laboratory, prognostic, diagnostic, prophylactic and therapeutic purposes; indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding CD37 or an antibody drug conjugate specifically binding to CD37.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

The CD37 Antigen

CD37, otherwise know as Leukocyte Antigen CD37 (as well as, inter alia, Tetraspanin-26) is a protein that is encoded by the CD37 gene. The protein encoded by this gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth, and motility. This encoded protein is a cell surface glycoprotein that is known to complex with integrins and other transmembrane 4 superfamily proteins. See, Virtaneva K I, et. al., Immunogenetics 37(6): 461-465 (March 1993). See also, Horejsi, et. al., FEBS Letters, Vol. 288 no. 1,2 pp. 1-4 (August 1991). See also, Link, et. al., J. Immun., vol. 137 no. 9, pp. 3013-3018 (November 1968). Also, it has been noted that alternate splicing results in multiple transcript variants encoding different isoforms. Tomlinson, et. al., Mol. Immun., vol 33, No. 10 pp 867-872 (1996). The CD37 cDNA is 1,263 bp in length and encodes a 281 amino acid ORF (See, FIG. 1). For exemplary embodiments of the CD37 antigen, see FIG. 1.

Example 2

Generation of CD37 Monoclonal Antibodies (MAbs)

In one embodiment, therapeutic Monoclonal Antibodies ("MAbs") to CD37 comprise those that react with epitopes specific for CD37 that would bind to CD37 expressed on cells. Immunogens for generation of such MAbs include those designed to encode or contain the extracellular domains or the entire CD37 protein sequence, regions predicted to contain functional motifs, and regions of CD37 predicted to be antigenic by computer analysis of the amino acid sequence. Immunogens include peptides and recombinant proteins and cells which endogenously express CD37 or that have been engineered to express CD37 (such as 293T-CD37).

MAbs to CD37 were generated using VelocImmune® technology (Regeneron, Tarrytown, N.Y.) wherein genetically engineered mice make antibodies that have fully human variable regions and mouse constant regions. The MAb designated HvCD37-6b15.1.1 was generated after immunizing velocimmune mice with recombinant 293T cells expressing CD37. The CD37 MAb, HvCD37-6b15.1.1 specifically binds to CD37 expressing cells (recombinant and endogenous).

After selection, the HvCD37-6b15.1.1 MAb (naturally produced by a hybridoma cell line) was converted to a Chinese Hamster Ovary (CHO) expressed fully human antibody by combining the human variable sequences from the velocimmune antibody with human constant regions.

DNA coding sequences for CD37 MAb HvCD37-6b15.1.1 was determined after isolating mRNA from the respective hybridoma cells with Trizol reagent (Life Technologies, Gibco BRL).

Anti-CD37 HvCD37-6b15.1.1 heavy and light chain variable nucleic acid sequences were sequenced from the hybridoma cells using the following protocol. HvCD37-6b15.1.1 secreting hybridoma cells were lysed with Trizol reagent (Life Technologies, Gibco BRL). Total RNA was purified and quantified. First strand cDNAs was generated from total RNA with oligo (dT)12-18 priming using the Gibco-BRL Superscript Preamplification system. First strand cDNA was amplified using human immunoglobulin variable heavy chain primers, and human immunoglobulin variable light chain primers. PCR products were sequenced and the variable heavy and light chain regions determined.

The nucleic acid and amino acid sequences of the variable heavy and light chain regions are listed in FIG. 2A or 2B and FIG. 3A or 3B. Alignment of HvCD37-6b15.1.1 MAb to human Ig germline is set forth in FIG. 4A-4B.

Example 3

Expression of HvCD37-6b15.1.1 Using Recombinant DNA Methods

To express HvCD37-6b15.1.1 MAb recombinantly in transfected cells, HvCD37-6b15.1.1 MAb variable heavy and light chain sequences were cloned upstream of the human heavy chain IgG2 and human light chain Igκ constant regions respectively. The complete HvCD37-6b15.1.1 MAb human heavy chain and light chain cassettes were cloned downstream of the CMV promoter/enhancer in a cloning vector. A polyadenylation site was included downstream of the MAb coding sequence. The recombinant HvCD37-6b15.1.1 MAb expressing construct was transfected into CHO cells. The HvCD37-6b15.1.1 MAb secreted from recombinant cells was evaluated for binding to human cancer cell lines expressing CD37 by FACS (See, Table VI). Binding was detected by flow cytometry. Results show that the recombinantly expressed HvCD37-6b15.1.1 expressed in CHO cells binds to CD37 on the cell surface.

Results show that the recombinantly expressed HvCD37-6b15.1.1 expressed in CHO cells binds CD37 similarly to the HvCD37-6b15.1.1 purified from hybridoma. The HvCD37-6b15.1.1 MAb secreted from recombinant cells was also evaluated for binding to CD37 recombinant protein by ELISA. Binding of HvCD37-6b15.1.1 to CD37 protein was identical between MAb material derived from CHO and from hybridoma cells.

The Chinese Hamster Ovary (CHO) cell producing an antibody designated HvCD37-6b15.1.1 was sent (via Federal Express) to the American Type Culture Collection (ATCC), P.O. Box 1549, Manassas, Va. 20108 on 8 Jul. 2013 and assigned Accession number 120464.

As a result of experimental analysis, using methods known in the art (e.g. protease digestion, LCMS analysis, etc.), amino acid modification(s) of the HvCD37-6b15.1.1 MAb derived from CHO cells, showed that the typical heavy chain includes modification of the N-terminal glutamine to pyroglutamate and deletion of the heavy chain C-terminal lysine in preparations of purified HvCD37-6b15.1.1 MAb.

Example 4

Antibody Drug Conjugation of HvCD37-6b15.1.1 MAb

The HvCD37-6b15.1.1 Mab (FIG. 2A or 2B) was conjugated to an auristatin derivative designated MMAE (Formula XI) using a vc (Val-Cit) linker described herein to create an antibody drug conjugate (ADC) designated HvCD37-6b15.1.1vcMMAE using the following protocols. The conjugation of the vc (Val-Cit) linker to the MMAE (Seattle Genetics, Seattle, Wash.) was completed using the general method set forth in Table IV to create the cytotoxic vcMMAE (see, US/2006/0074008).

Next, the antibody drug conjugate (ADC) designated HvCD37-6b15.1.1vcMMAE was made using the following protocols.

Briefly, 2.7 mg/mL of the HvCD37-6b15.1.1 MAb in 35.5 mL of phosphate buffer saline at pH 7.4 is added with a 1% volume of 5N NaCl, 11% volume of 0.5N sodium borate buffer pH 9.0, and 1% volume of 0.5M EDTA to adjust the pH of the solution to 8.9, 5 mM EDTA and 50 mM sodium chloride. The MAb is then partially reduced by adding 11.5 molar equivalents of TCEP (relative to moles of MAb) and then stirred at 37° C. for 2.5 hours. The partially reduced MAb solution is then cooled to room temperature and 5.2 molar equivalents of vcMMAE (relative to moles of antibody) are added as an 8% (v/v) solution of DMSO. The mixture is stirred for sixty (60) minutes at room temperature, then for ten (10) additional minutes following the addition of five (5) molar equivalents of N-acetylcysteine relative to mAb. Excess quenched vcMMAE and other reaction components are removed by ultrafiltration/diafiltration of the antibody drug conjugate (ADC) with 6 diavolumes of 20 mM histidine, pH 5.2, then 40% of concentrated sucrose solution was added to adjust the sucrose concentration to 5%.

The resulting antibody drug conjugate (ADC) is designated HvCD37-6b15.1.1vcMMAE and has the following formula:

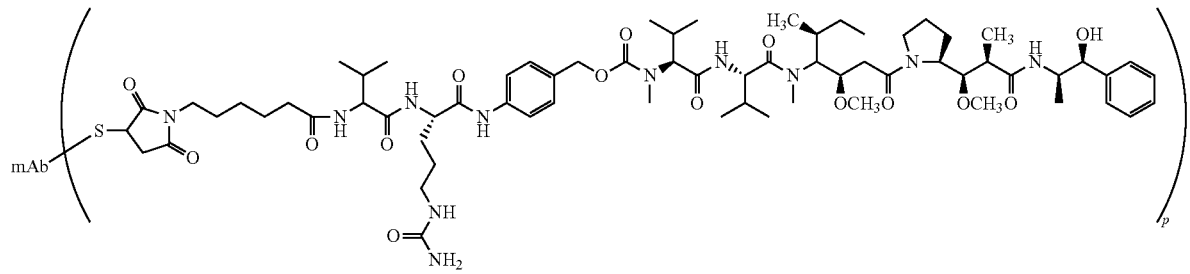

wherein MAb is HvCD37-6b15.1.1 (FIG. 2A or 2B and FIG. 3A or 3B) and p is from 1 to 10. The preferred p value of the antibody drug conjugate set forth in this Example is between 3.5 and 3.7.

Example 5

Characterization of HvCD37-6b15.1.1 MAb

MAbs that bind CD37 were generated using the procedures set forth in the example entitled "Generation of CD37 Monoclonal Antibodies (MAbs)" and were screened, identified, and characterized using a combination of assays known in the art.

A. FACS Binding

HvCD37-6b15.1.1 was tested for binding to different NHL, CLL and AML cell lines (See, Table VI) grown in-vitro. HvCD37-6b15.1.1 and an Isotype matched control antibody were biotinylated using NHS LC biotin. In vitro cancer lines growing exponentially were used for all experiments. Briefly, cells were harvested by and washed by centrifugation. Antibodies were diluted to 5 g/mL final concentration and co-incubated with cells at 4° C. for 1 hour. At the end of the incubation, cells were washed and incubated with secondary detection Streptavidin-PE antibody at a final 1:400 (1.25 g/mL) dilution for 1 hr at 4° C. After washing un-bound secondary antibody, cells were analyzed by FACS, a total of 10,000 events were collected per sample. Data files were analyzed using FlowJo and Geometric Mean Fluorescence was determined and reported. Fluorescense ratio was calculated as follows: Geo mean AGS67C/Geo Mean Isotype control=MFR, a measure of fold expression above Isotype control.

Geometric Mean values and Mean Florescence ratios (MFR) values were obtained (Table VI) and histograms are shown (FIG. 12A-D and FIG. 13A-C) The results show that the HVCD37-6b15.1.1 binds several human cancer cell lines expressing NHL, CLL, and AML.

Example 6

HvCD37-6b15.1.1vcMMAE Inhibit Growth of Tumors In Vivo

The significant expression of CD37 in tumor cells, together with its restrictive expression in normal cells makes CD37 a good target for antibody therapy and similarly, therapy via ADC. Thus, the therapeutic efficacy of HvCD37-6b15.1.1vcMMAE in human CLL, AML, and NHL cancer xenograft mouse models is evaluated.

Antibody drug conjugate efficacy on tumor growth and metastasis formation is studied in mouse cancer xenograft models (e.g. subcutaneous and orthotopically).

Subcutaneous (s.c.) tumors are generated by injection of $5 \times 10^4$-$10^6$ cancer cells mixed at a 1:1 dilution with Matrigel (Collaborative Research) in the right flank of male SCID mice. To test ADC efficacy on tumor formation, i.e. ADC injections are started on the same day as tumor-cell injections. As a control, mice are injected with either purified human IgG or PBS; or a purified MAb that recognizes an irrelevant antigen not expressed in human cells. In preliminary studies, no difference is found between control IgG or PBS on tumor growth. Tumor sizes are determined by caliper measurements, and the tumor volume is calculated as $width^2 \times Length/2$, wherein width is the smallest dimension and length is the largest dimension. Mice with subcutaneous tumors greater than 1.5 cm in diameter are sacrificed.

An advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

HvCD37-6b15.1.1ADC inhibits formation in cancer cell line(s) denoted DoHH2, Ramos-RR-XCL, CLL-JVM3, AML-MV-4-11, and human lymphoma Raji cancer xenografts. These results indicate the utility of HvCD37-6b15.1.1ADC in the treatment of local and advanced stages of cancer and preferably those cancers set forth in Table I.

CD37 ADCs:

Monoclonal antibodies were raised against CD37 as described in the Example entitled "Generation of CD37 Monoclonal Antibodies (MAbs)." Further the MAbs are conjugated to a toxin as described in the Example entitled "Antibody Drug Conjugation of HvCD37-6b15.1.1 MAb" to form HvCD37-6b15.1.1vcMMAE. The HvCD37-6b15.1.1 and HvCD37-6b15.1.1vcMMAE is characterized by FACS, and other methods known in the art to determine its capacity to bind CD37.

Cell Lines and Xenografts:

The cells are maintained in DMEM, supplemented with L-glutamine and 10% FBS, as known in the art. The DoHH2, Ramos-RR-XCL, CLL-JVM3, AML-MV-4-11, and human lymphoma Raji xenografts are maintained by serial propagation in SCID mice.

Evaluation of HvCD37-6b15.1.1.vcMMAE in Subcutaneously Established Human Follicular B Cell Lymphoma DoHH2 Implanted in CB17/SCID Mice.

In this experiment, human follicular B-cell lymphoma DoHH2 cells ($10 \times 10^6$ cells per mouse) were injected into the flanks of individual CB17/SCID mice and tumors were allowed to grow untreated until they reached an approximate volume of 200 mm$^3$ (QW×2). At that point, animals were allocated to each group based on tumor volume at the time of treatment initiation to ensure similar mean tumor size and variation in each group using Study Director Software (v.1.7; Studylog Systems, Inc., South San Francisco, Calif.). All ADC treated groups received two (2) doses on day zero (0) and day seven (7) by intravenous bolus injection. Tumor growth in each group was monitored twice weekly using caliper measurements until study termination. Statistical analysis of tumor volumes was performed at the last time point when data from all groups were available using a nonparametric analysis of variance (ANOVA) on the ranked data.

The results show that HvCD37-6b15.1.1vcMMAE demonstrated a potent dose escalated inhibitory effect when compared to the non-treated control ($p<0.0001$) (FIG. 5).

Evaluation of HvCD37-6b15.1.1.vcMMAE in Subcutaneously Established Xenograft Model of Human Lymphoma Ramos-RR-XCL Implanted in CB17/SCID Mice.

In another experiment, human lymphoma Ramos-RR-XCL cells ($3 \times 10^6$ cells per mouse) were injected into the flanks of individual CB17/SCID mice and tumors were allowed to grow untreated until they reached an approximate volume of 200 mm$^3$ (QW×2). At that point, animals were allocated to each group based on tumor volume at the time of treatment initiation to ensure similar mean tumor size and variation in each group using Study Director Software (v.1.7; Studylog Systems, Inc., South San Francisco, Calif.). All ADC treated groups received two (2) doses on day zero (0) and day six (6) by intravenous bolus injection. Additionally, four (4) doses of Rituxan were administered on days 0, 3, 6, and 9 (Ramos-RR-XCL is a Rituxan resistant cell line). Tumor growth in each group was monitored twice weekly using caliper measurements until study termination. Statistical analysis of tumor volumes was performed at the last time point when data from all groups were available using a nonparametric analysis of variance (ANOVA) on the ranked data.

The results show that HvCD37-6b15.1.1vcMMAE demonstrated a potent dose escalated tumor inhibitory effect when compared to the non-treated control or to the corresponding ADC control H3-12bc1.1vcMMAE (both $p<0.0001$) (FIG. 6).

Efficacy Study of HvCD37-6b15.1.1.vcMMAE in Subcutaneously Established Human Chronic Lymphocytic Leukemia JVM3 Implanted in CB17/SCID Mice In another experiment, chronic lymphocytic leukemia JVM3 cells ($10 \times 10^6$ cells per mouse) were injected into the flanks of individual CB17/SCID mice and tumors were allowed to grow untreated until they reached an approximate volume of 200 mm$^3$ (QW×3). At that point, animals were allocated to each group based on tumor volume at the time of treatment initiation to ensure similar mean tumor size and variation in each group using Study Director Software (v.1.7; Studylog Systems, Inc., South San Francisco, Calif.). All ADC treated groups received three (3) doses on day zero (0) and day seven (7) and day fourteen (14) by intravenous bolus injection. Tumor growth in each group was monitored twice weekly using caliper measurements until study termination. Statistical analysis of tumor volumes was performed at the last time point when data from all groups were available using a nonparametric analysis of variance (ANOVA) on the ranked data.

The results show that HvCD37-6b15.1.1vcMMAE demonstrated a potent dose dependant inhibitory effect when compared to the vehicle control (p<0.0001) or to the corresponding ADC control Ha3-12bc1.1vcMMAE (p=0.0001) (FIG. 7).

Efficacy Study of HvCD37-6b15.1.1.vcMMAE in Subcutaneously Established Human Acute Myelogenous Leukemia MV-4-11 Implanted in CB17/SCID Mice.

In another experiment, acute myelogenous leukemia MV-4-11 cells ($3\times10^6$ cells per mouse) were injected into the flanks of individual CB17/SCID mice and tumors were allowed to grow untreated until they reached an approximate volume of 200-250 mm$^3$ (QW×3). At that point, animals were allocated to each group based on tumor volume at the time of treatment initiation to ensure similar mean tumor size and variation in each group using Study Director Software (v.1.7; Studylog Systems, Inc., South San Francisco, Calif.). All ADC treated groups received three (3) doses on day zero (0) and day seven (7) and day fourteen (14) by intravenous bolus injection. Tumor growth in each group was monitored twice weekly using caliper measurements until study termination. Statistical analysis of tumor volumes was performed at the last time point when data from all groups were available using a nonparametric analysis of variance (ANOVA) on the ranked data.

The results show that HvCD37-6b15.1.1vcMMAE demonstrated a potent dose dependant inhibitory effect when compared to the vehicle control (p<0.0001) or to the corresponding ADC control Ha3-12bc1.1vcMMAE (p=0.0001) (FIG. 8).

Efficacy Study of HvCD37-6b15.1.1.vcMMAE in Subcutaneously Established Human Rituxan Resistant Lymphoma Cell Line Ramos-RR-XCL Implanted in SCID Mice.

In another experiment, human lymphoma Ramos-RR-XCL cells ($3\times10^6$ cells per mouse) were injected into the flanks of individual ICR/SCID mice and tumors were allowed to grow untreated until they reached an approximate volume of 200 mm$^3$ (QW×2). At that point, animals were allocated to each group based on tumor volume at the time of treatment initiation to ensure similar mean tumor size and variation in each group using Study Director Software (v.1.7; Studylog Systems, Inc., South San Francisco, Calif.). All ADC treated groups received four (4) doses on day zero (0) and day four (4) day seven (7) and day eleven (11) by intravenous bolus injection. Tumor growth in each group was monitored twice weekly using caliper measurements until study termination. Statistical analysis of tumor volumes was performed at the last time point when data from all groups were available using a nonparametric analysis of variance (ANOVA) on the ranked data.

The results show that HvCD37-6b15.1.1vcMMAE demonstrated significant superior inhibitory effect when compared to other CD37 ADCs dosed at 1 mg/kg. (FIG. 9).

Efficacy Study of HvCD37-6b15.1.1.vcMMAE and HvCD37-6b15.1.1 in Subcutaneously Established Xenograft Model of Human Acute Monocytic Leukemia Cell Line MOLM-13 Implanted in SCID Mice.

In another experiment, Human acute monocytic leukemia MOLM-13 cells ($1.0\times10^6$ cells per mouse) were injected into the flanks of individual SCID mice and tumors were allowed to grow. When the average tumor volumes reached a predetermined size (e.g. 200 mm$^3$), animals were size matched and randomized into treatment and control groups with similar mean tumor size and variation in each group using Study Director Software (v.2.1; Studylog Systems, Inc., South San Francisco, Calif.). HvCD37-6b15.1.1vcMMAE and HvCD37-6b15.1.1 were dosed at 1.0 mg/kg either as a single dose or once a week for a total of two (2) doses by intravenous bolus injection. The control ADC and control MAb, Ha8-7acd6.1-vcMMAE and Ha8-7acd6.1, were dosed at 1.0 mg/kg once a week for a total of two (2) doses by intravenous bolus injection. Five (5)% Dextrose was used as the vehicle control. All agents were administered based on the individual body weight of each animal obtained immediately prior to each dosing. Tumor growth in each group was monitored twice (2×) weekly using caliper measurements until study termination. A statistical analysis of the tumor volume data for the last day before animal sacrifice was performed using the Kruskal-Wallis test. Pairwise comparisons were made using Tukey's test procedures (2-sided) to protect the experiment-wise error rate. The study evaluated the efficacy of HvCD37-6b15.1.1vcMMAE and compared it to its naked antibody component HvCD37-6b15.1.1 in the MOLM-13 human acute monocytic leukemia xenograft model.

Figure 11:
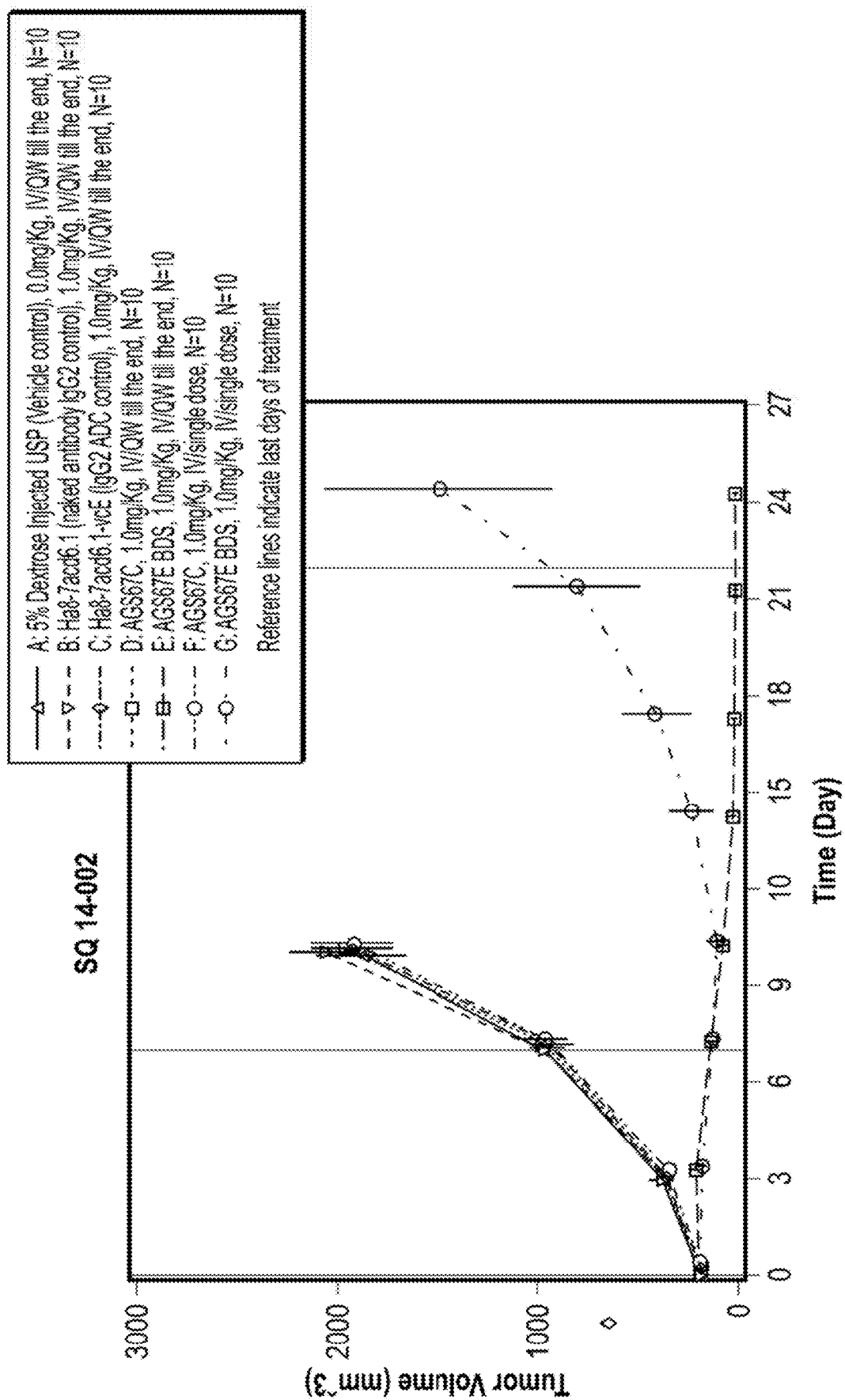
FIG. 11. Efficacy study of HvCD37-6b15.1.1vcMMAE (a.k.a. AGS67E) and HvCD37-6b15.1.1 MAb (a.k.a. AGS67C) in subcutaneously established xenograft model of human acute monocytic leukemia cell line MOLM-13 implanted in SCID mice.
Figure 12A:
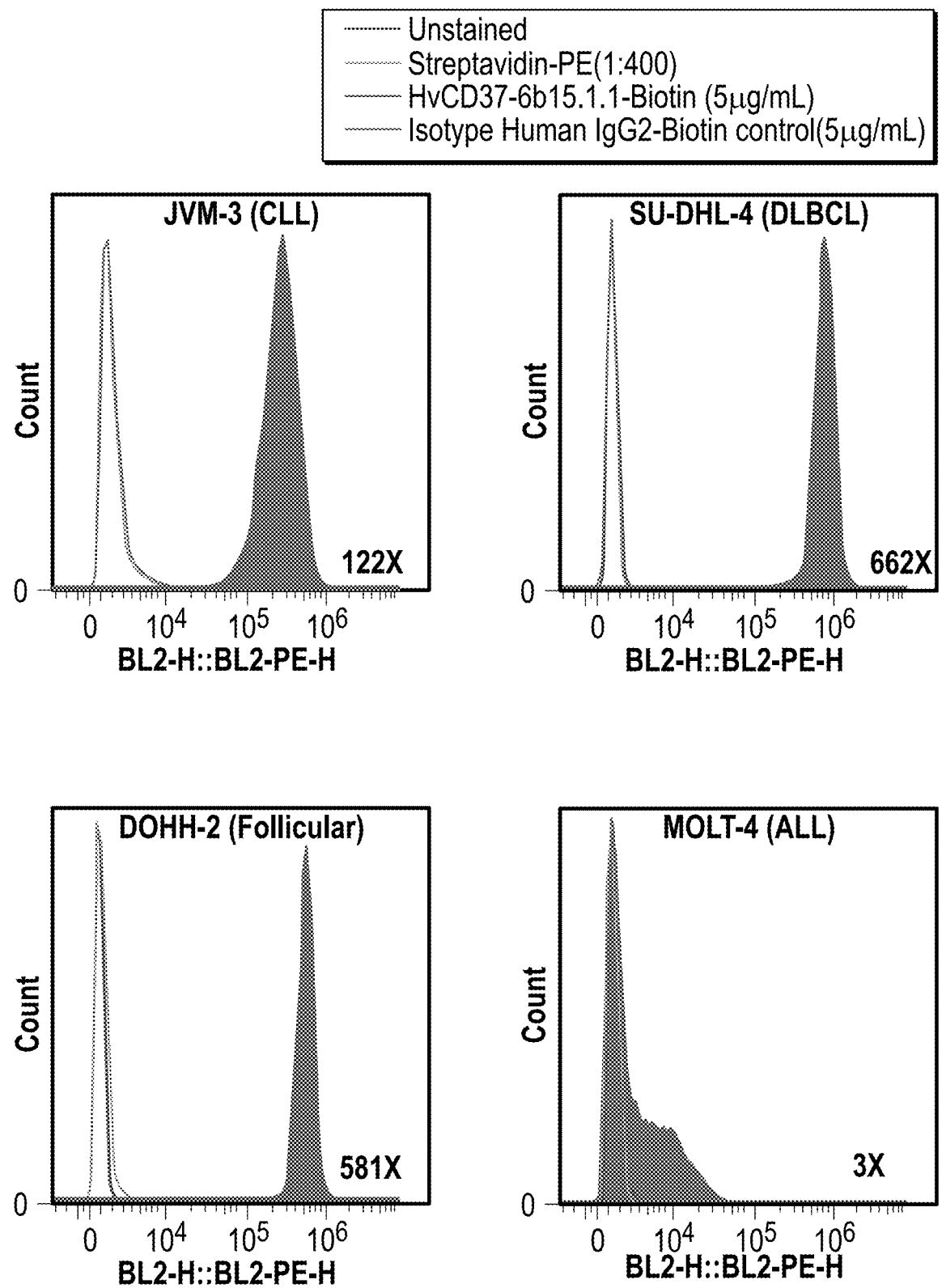
Figure 12B:
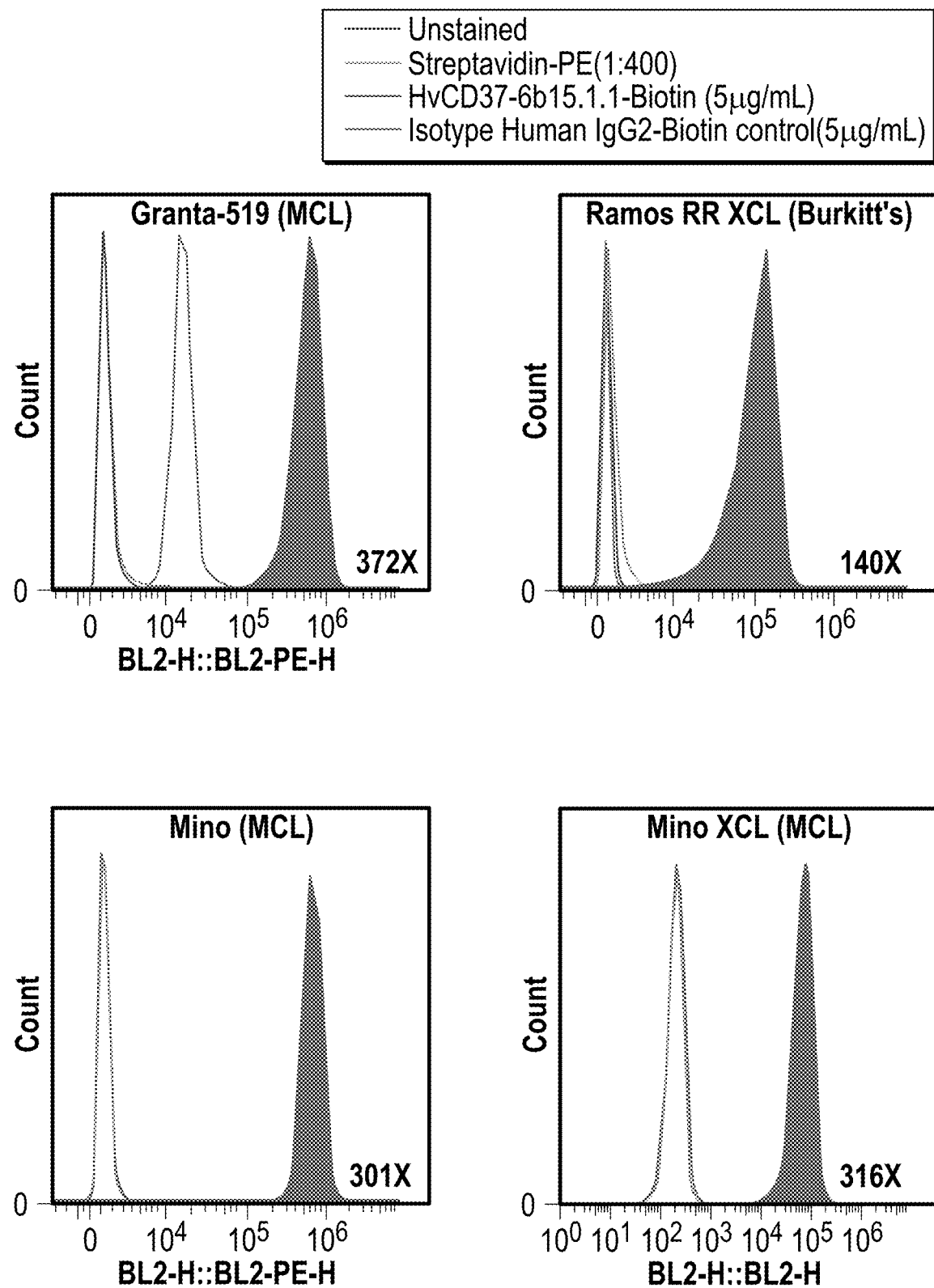
Figure 12C:
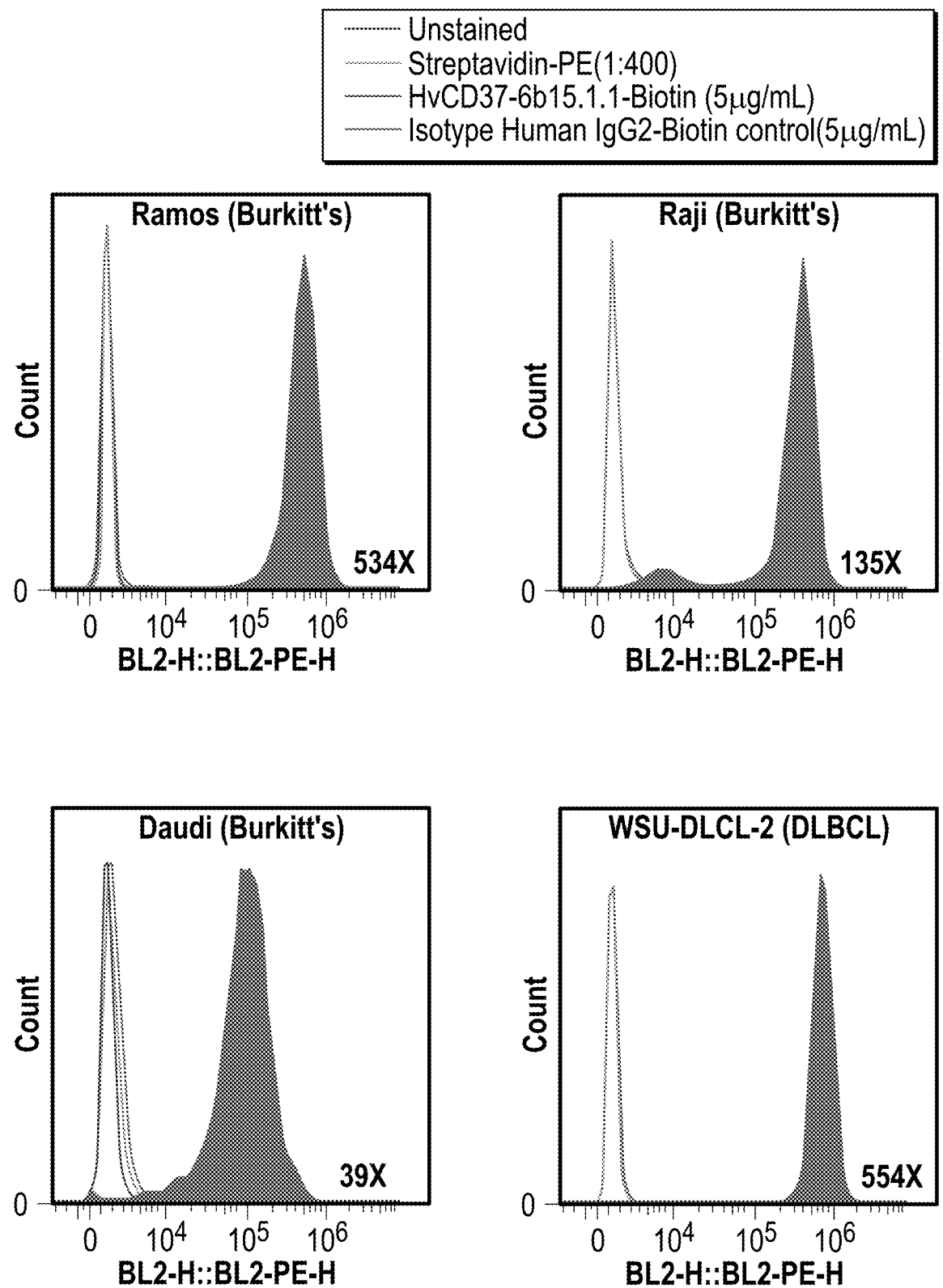
Figure 13B:
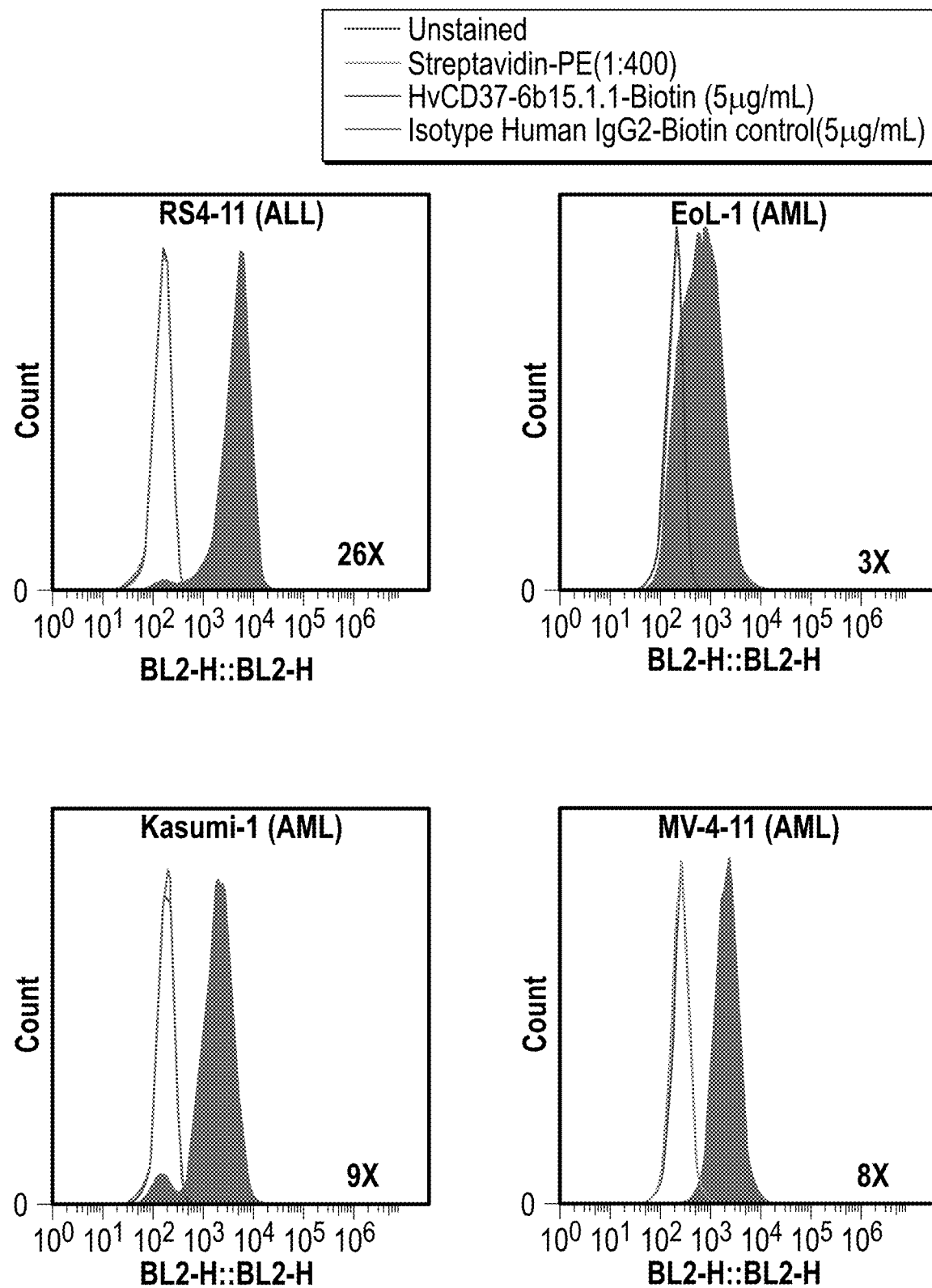
Figure 13C:
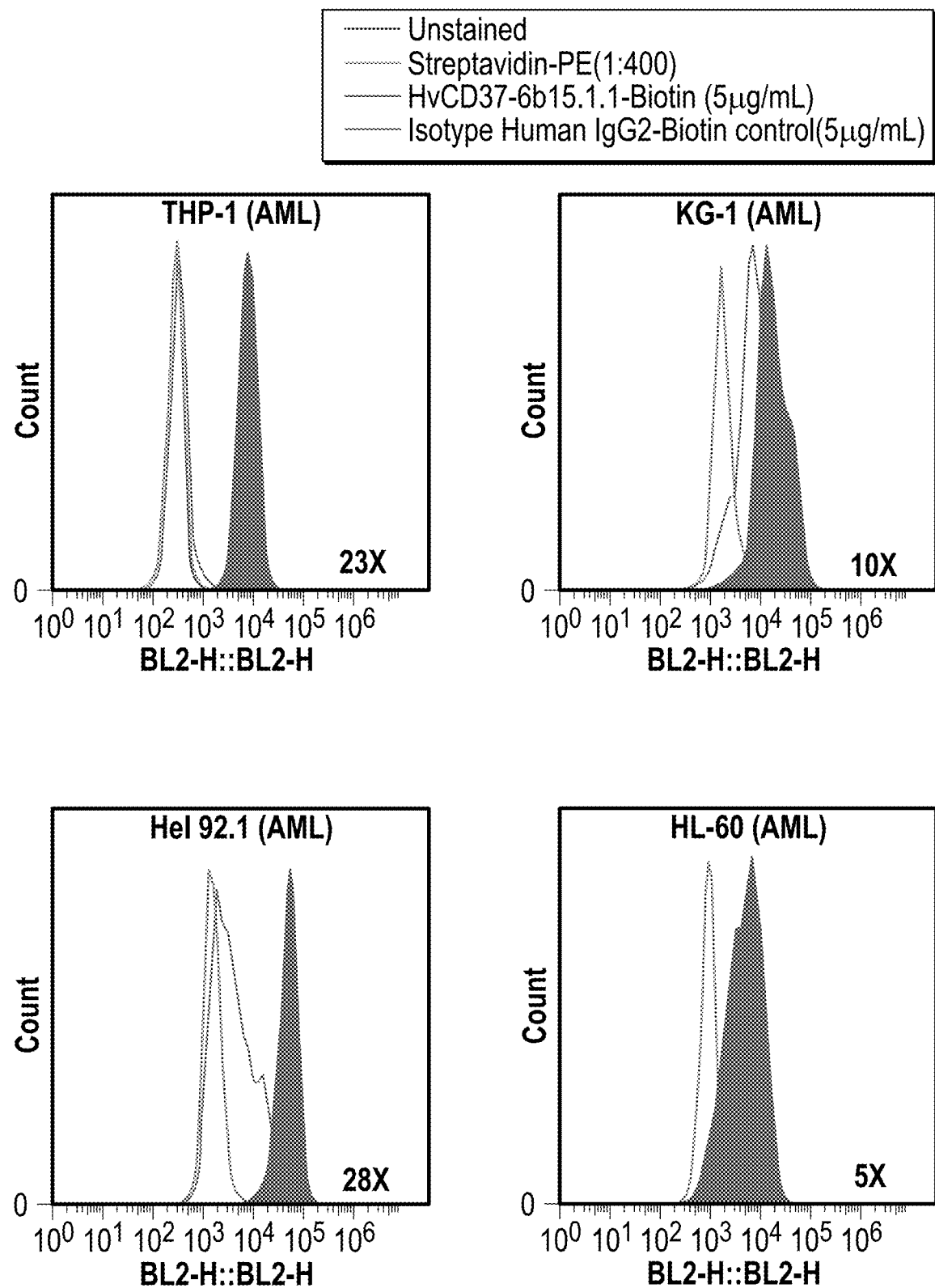

The results show that the naked MAb HvCD37-6b15.1.1 did not show any efficacy as compared to the HvCD37-6b15.1.1vcMMAE antibody drug conjugate which demonstrated significant superior inhibitory effect. (FIG. 11).

Conclusion

In summary, FIGS. 5-9, and 11, show that the CD37 ADC entitled HvCD37-6b15.1.1vcMMAE significantly inhibited the growth of tumors cells that express CD37 when compared to control ADCs. Thus, the HvCD37-6b15.1.1vcMMAE can be used for therapeutic purposes to treat and manage cancers set forth in Table I. Additionally, it can be shown that the ADC entitled HvCD37-6b15.1.1 shows an significant superior effect over other ADCs directed to CD37 and other antibodies directed to CD37. Accordingly, the significant effects of HvCD37-6b15.1.1 show prominence as a therapeutic agent to treat and manage the cancers set forth in Table I.

Example 7

Human Clinical Trials for the Treatment and Diagnosis of Human Carcinomas Through Use of CD37 ADCs in some embodiments CD37 ADCs are used in accordance with the present invention which specifically bind to CD37, and are used in the treatment of certain tumors, preferably those listed in Table I. In connection with each of these indications, two clinical approaches are successfully pursued.

I.) Adjunctive therapy: In adjunctive therapy, patients are treated with CD37 ADCs in combination with a chemotherapeutic or anti-neoplastic agent and/or radiation therapy or a combination thereof. Primary cancer targets, such as those listed in Table I, are treated under standard protocols by the addition of CD37 ADCs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. CD37 ADCs are utilized in several adjunctive clinical trials in combination with the chemotherapeutic or anti-neoplastic agents.

II.) Monotherapy: In connection with the use of the CD37 ADCs in monotherapy of tumors, the CD37 ADCs are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention in some embodiments dictated by and directly dependent on (a) the unique characteristics of the antibody and/or ADC and the particular therapeutic or prophylactic effect to be achieved, and (b) the limitations inherent in the art of compounding such an active compound for the treatment of sensitivity in individuals.

An exemplary, non limiting range for a therapeutically effective amount of an CD37 ADC administered in combination according to the invention is about 0.5 to about 10 mg/kg, about 1 to about 5 mg/kg, at least 1 mg/kg, at least 2 mg/kg, at least 3 mg/kg, or at least 4 mg/kg. Other exemplary non-limiting ranges are for example about 0.5 to about 5 mg/kg, or for example about 0.8 to about 5 mg/kg, or for example about 1 to about 7.5 mg/kg. A high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of CD37 ADCs in connection with adjunctive therapy or monotherapy. Trials initially demonstrate safety and thereafter confirm efficacy in repeat doses. Trials are open label comparing standard chemotherapy with standard therapy plus CD37 ADCs. As will be appreciated, one non-limiting criteria that can be utilized in connection with enrollment of patients is CD37 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAMA response); and, (iii) toxicity to normal cells that express CD37. Standard tests and follow-up are utilized to monitor each of these safety concerns. CD37 ADCs are found to be safe upon human administration.

Example 8

Detection of CD37 Protein in Cancer Patient Specimens by IHC

Expression of CD37 protein by immunohistochemistry was tested in tumor specimens from non-Hodgkin's lymphoma (NHL) and Multiple myeloma ("MM") patients. Briefly, formalin fixed, paraffin wax-embedded tissues were cut into four (4) micron sections and mounted on glass slides. The sections were de-waxed, rehydrated and treated with Citra antigen retrieval solution (Biogenex, San Ramon, Calif.) in the EZ-Retriever microwave (Biogenex, San Ramon, Calif.) for 45 minutes at 95° C. Sections were then treated with 3% hydrogen peroxide solution to inactivate endogenous peroxidase activity. Serum-free protein block (Dako, Carpenteria, Calif.) was used to inhibit non-specific binding prior to incubation with monoclonal mouse anti-CD37 antibody or an isotype control. Subsequently, the sections were treated with the Super Sensitive™ Polymer-horseradish peroxidase (HRP) Detection System which consists of an incubation in Super Enhancer™ reagent followed by an incubation with polymer-HRP secondary antibody conjugate (BioGenex, San Ramon, Calif.). The sections were then developed using the DAB kit (BioGenex, San Ramon, Calif.), nuclei were stained using hematoxylin, and analyzed by bright field microscopy. Specific staining was detected in patient specimens using the CD37 immunoreactive antibody, as indicated by the brown staining (See, FIGS. 10(A) and 10(C)). In contrast, the control antibody did not stain the patient specimen (See, FIGS. 10 (B) and 10(D)).

The results show expression of CD37 in the tumor cells of NHL and MM. These results indicate that CD37 is expressed in human NHL and MM and that antibodies directed to this antigen (e.g. HvCD37-6b15.1.1) and the antibody drug conjugate designated HvCD37-6b15.1.1vcMMAE) are useful for diagnostic and therapeutic purposes. (FIG. 10).

Example 9

HvCD37-6b15.1.1 MAb Binding to Patient Derived Specimens

The binding of HvCD37-6b15.1.1 MAb was assessed in PBMC samples from peripheral blood of patients with Acute Lymphocytic Leukemia in the Myeloid (AML), Leukemic Stem Cell (LSC), T cell and B Lymphocyte cell populations.

A. FACS Binding Materials and Methods

In this experiment, HvCD37-6b15.1.1 and Isotype matched control antibody were biotinylated using NHS LC Biotin (Thermo Scientific, Rockford, Ill.). Ficoll-Paque (GE Healthcare, Pittsburgh, Pa.) isolations of Peripheral blood cells (PBMC) were obtained from Acute Myeloid Leukemia patients after consent and approval. Freshly thawed PBMC were incubated with a cocktail CD45, CD33, CD 38 (BD Biosciences, San Jose, Calif.) CD34, CD3 (Beckman Coulter, Brea, Calif.) and either HvCD37-6b15.1.1-Biotin (anti CD37) or Isotype-Biotin mAbs. Fluorescense minus one (FMO) control cocktails were prepared with Streptavidin-PE (SAv-PE) (BD Biosciences, San Jose, Calif.) detection reagent and were used for gating of cell populations. Secondary detection for biotinylated HvCD37-6b15.1.1 and Isotype mAbs was SAv-PE or SAv-PC5. An LSRII flow cytometer (BD Biosciences, San Jose, Calif.) was used for acquisition of data. Lymphocytes were gated on CD45+ (leukocyte common antigen) population from which four (4) distinct populations were defined, CD33+/3−/20− (Myeloid Blasts), CD33+/3−/34+/38− (LSC), CD33−/3+ (T lymphocytes) and CD33−/20+ (B Lymphocytes). Analysis was done with FlowJo version 9.5.4 software (Tri Star, Ashland, Oreg.). MFIR for each AML sample was calculated by dividing the HvCD37-6b15.1.1 MFI over matched Isotype MFI.

B. Results

Geometric Mean values and Mean Flourescense Intensity Ratios (MFIR) were obtained by dividing the HvCD37-6b15.1.1 MFI over matched Isotype control MFI. The results set forth in Table VII for AML patient samples shows that HvCD37-6b15.1.1 MAb binds to the Myeloid, LSC, T and B cell populations of all samples tested.

Figure 14A:
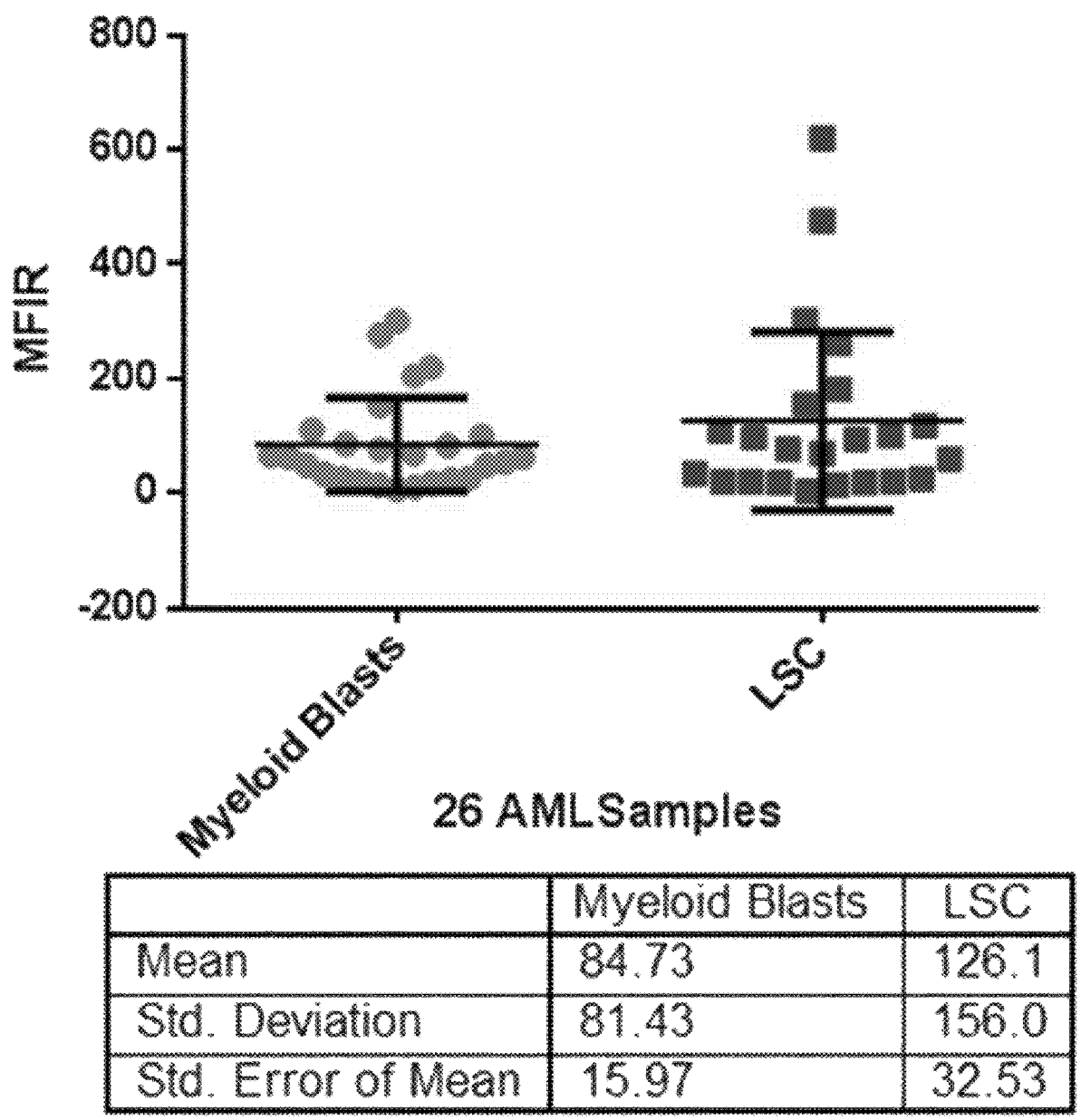
FIGS. 14A-B. HvCD37-6b15.1.1 MFIR Distribution on Myeloid, LCS, T-cells and B-cells
Figure 14B:
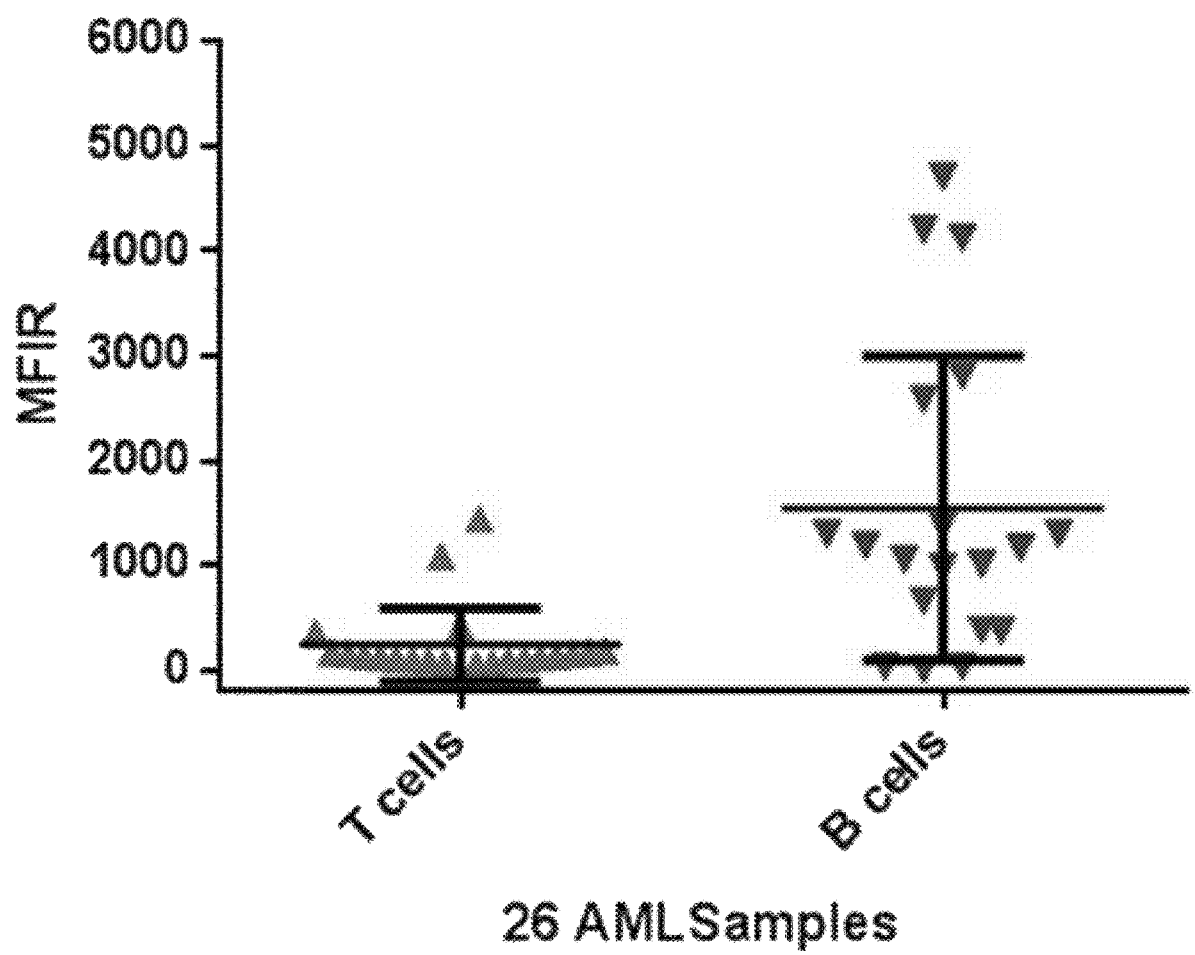

Furthermore, as shown in FIGS. 14A and 14B, the MFIR distribution plots for all samples tested show high variability in the LSC and B cell populations, while Myeloid Blasts and T cells had less variability in MFIR. Mean MFIR for Myeloid blasts was around eighty-five (85) with binding present in all samples, while mean MFIR for LCS was one hundred and twenty-six (126), with three samples showing high levels of HvCD37-6b15.1.1 binding. HvCD37-6b15.1.1 staining on B cells was the highest for all the populations with a mean MFIR of 1548, while mean T cell binding was lower (MFIR 246) than for B cells. (See, FIGS. 14A and 14B).

Additionally, as shown in Table VIII, cell population distribution for Patient lymphocytes shows the majority are CD33+(Myeloid) positive as characteristic in AML. Small populations of LSC (VD34+/38−), T (CD3+) and B cells (CD20+) were also observed. All four populations are CD37 positive as confirmed by HvCD37-6b15.1.1 binding.

The totality of the results set forth in Table(s) VIII, IX, and X show that the HvCD37-6b15.1.1 MAb specifically binds to patient derived tissues that express AML, LSC, and T and B cell lymphocyte.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues/Cells that express CD37 when malignant.

Acute Myeloid Leukemia ("AML");
Chronic Lymphocytic Leukemia ("CLL")
Non Hodgkins Lymphoma ("NHL");
Multiple Myeloma ("MM").

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |
|   |   |   |   | 6 | −3 | −1 | 0 | −3 | 0 | 0 | −3 | −4 | −3 | −3 | −2 | −2 | −1 | 1 | 3 | F |
|   |   |   |   |   | 6 | −2 | −4 | −2 | −4 | −3 | 0 | −2 | −2 | −2 | 0 | −2 | −3 | −2 | −3 | G |
|   |   |   |   |   |   | 8 | −3 | −1 | −3 | −2 | 1 | −2 | 0 | 0 | −1 | −2 | −3 | −2 | 2 | H |
|   |   |   |   |   |   |   | 4 | −3 | 2 | 1 | −3 | −3 | −3 | −3 | −2 | −1 | 3 | −3 | −1 | I |

TABLE III-continued

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |
| | | | | | | | | | | | | | | | 4 | 1 | −2 | −3 | −2 | S |
| | | | | | | | | | | | | | | | | 5 | 0 | −2 | −2 | T |
| | | | | | | | | | | | | | | | | | 4 | −3 | −1 | V |
| | | | | | | | | | | | | | | | | | | 11 | 2 | W |
| | | | | | | | | | | | | | | | | | | | 7 | Y |

TABLE IV

General Method for Synthesis of vcMMAE

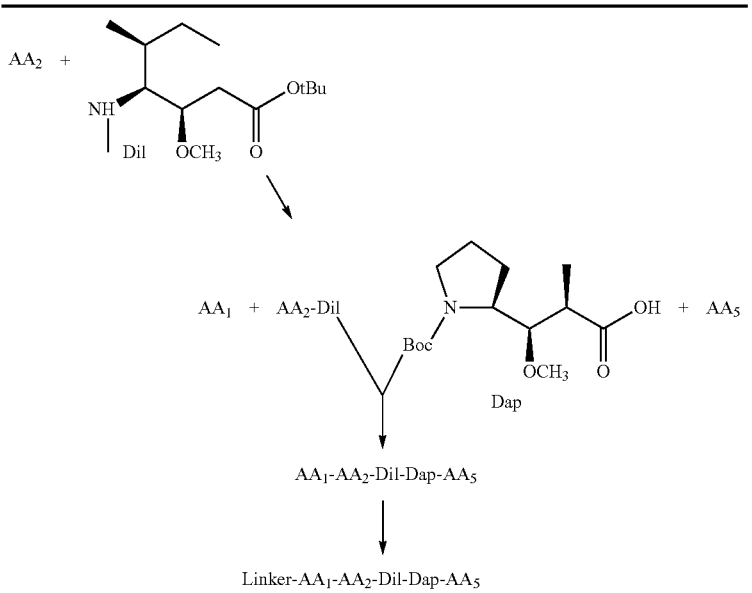

Where:
AA1 = Amino Acid 1
AA2 = Amino Acid 2
AA5 = Amino Acid 5
DIL = Dolaisoleuine
DAP = Dolaproine
Linker = Val-Cit (vc)

TABLE V

Positions CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

| CDR | Kabat | Chothia | Contact |
|---|---|---|---|
| CDR-L1 | L24-L34 | L24-L34 | L30-L36 |
| CDR-L2 | L50-L56 | L50-L56 | L46-L55 |
| CDR-L3 | L89-L97 | L89-L97 | L89-L96 |
| CDR-H1* | H31-H35 | H26-H32 | H30-H35 |
| CDR-H1** | H31-H35 | H26-H32 | H30-H35 |
| CDR-H2 | H50-H65 | H52-H56 | H47-H58 |
| CDR-H3 | H95-H102 | H95-H102 | H93-H101 |

*Kabat Numbering
**Chothia Numbering

TABLE VI

Table of Geometric Mean values and Mean Florescence ratio (MFR) values in FACS assay.

| Cell line | Cancer type | Source | unstained | secondary detection | Isotype | HvCD37-6b15.1.1 | MFR |
|---|---|---|---|---|---|---|---|
| JVM-3 | CLL | DSMZ | 1871 | 1792 | 1931 | 236000 | 122 |
| SU-DHL-4 | DLBCL | DSMZ | 1097 | 1046 | 1053 | 697000 | 662 |
| DOHH-2 | Follicular | DSMZ | 888 | 1172 | 840 | 488000 | 581 |
| MOLT-4 | ALL | NCl | 1494 | 1280 | 1310 | 3606 | 3 |
| Granta-519* | MCL | DSMZ | 1363 | 1408 | 15400 | 524000 | 372 |
| Ramos RR XCL | Burkitt's | ATCC in-vivo selection (rituxan resistant) | 679 | 1093 | 693 | 97276 | 140 |
| Mino | MCL | ATCC | 1438 | 1409 | 1484 | 446000 | 301 |
| Mino XCL | MCL | ATCC in-vivo xenograft | 201 | 198 | 200 | 63100 | 316 |
| Ramos | Burkitt's | ATCC | 1232 | 1117 | 1151 | 615000 | 534 |
| Raji | Burkitt's | ATCC | 1590 | 1648 | 1761 | 237000 | 135 |
| Daudi | Burkitt's | ATCC | 1513 | 1780 | 2039 | 79000 | 39 |
| WSU-DLCL-2 | DLBCL | DSMZ | 1214 | 1149 | 1203 | 666000 | 554 |
| REC-1 | MCL | DSMZ | 870 | 6149 | 1013 | 345554 | 341 |
| BDCM | AML | ATCC | 219 | 286 | 290 | 18500 | 64 |
| MOLM-13 | AML | DSMZ | 263 | 245 | 240 | 1514 | 6 |
| RS4-11 | ALL | ATCC | 154 | 149 | 155 | 4054 | 26 |
| EoL-1 | AML | Sigma/HPA | 197 | 189 | 189 | 604 | 3 |
| Kasumi-1 | AML | DSMZ | 172 | 190 | 188 | 1710 | 9 |
| MV-4-11 | AML | ATCC | 263 | 249 | 247 | 2065 | 8 |
| THP-1 | AML | ATCC | 266 | 296 | 324 | 7355 | 23 |
| KG-1* | AML | NCl | 985 | 1787 | 8190 | 18100 | 10 |
| Hel 92.1* | AML | ATCC | 1455 | 1521 | 4216 | 42600 | 28 |
| HL-60 | AML | ATCC | 867 | 889 | 967 | 4602 | 5 |

Note:
*All MFR ratios calculated with the Isotype control as reference, except for Granta-519, KG-1 and Hel 92.1 where the secondary detection was used as reference due to the high Isotype control background binding.

TABLE VII

HvCD37-6b15.1.1 MFIR values for AML samples

| AML Type | CD45+ sample | Myeloid Blasts | LCS CD34+/38− | T cells CD3+ | B cells CD20+ |
|---|---|---|---|---|---|
| M1 | 502 | 7 | 4 | 3 | 36 |
| M1 | 596 | 54 | 21 | 185 | 1196 |
| M5b | 598 | 17 | 302 | 1449 | 4130 |
| M5a | 80534 | 66 | 35 | 124 | <0.1% of sample |
| M6 | 90165 | 77 | 118 | <0.1% of sample | 17 |
| M1 | 90191 | 220 | 155 | 142 | 38 |
| M5a | 90392 | 69 | <0.1% of sample | <0.1% of sample | 2818 |
| M4 | 90429 | 11 | 21 | 423 | |
| M1 | 90454 | 26 | 620 | 155 | 386 |
| M5a | 90481 | 21 | 18 | 89 | 982 |
| M2 | 90543 | 111 | 95 | 175 | 1166 |
| M5a | 90686 | 49 | 26 | 170 | 4715 |
| M5a | 100016 | 33 | <0.1% of sample | 142 | 667 |
| M4 | 100091 | 100 | 110 | <0.1% of sample | 1379 |
| M5a | 100183 | 86 | 77 | <0.1% of sample | 2598 |
| M5a | 100474 | 205 | 101 | 75 | 389 |
| Unclassified | 100454 | 83 | 97 | 163 | 1013 |
| M5a | 110283 | 153 | 181 | 106 | 1063 |
| M1 | 110484 | 26 | <0.1% of sample | 1090 | 4205 |
| M5a | 110500 | 63 | 476 | 361 | 1309 |
| M4Eo | 120277 | 23 | 17 | 109 | 1306 |
| M1 | 120287 | 301 | 14 | 100 | |
| Unclassified | 120298 | 49 | 20 | 132 | |
| M4 | 120314 | 14 | 70 | 95 | |
| M1 | 120321 | 62 | 60 | 72 | |
| M1 | 120409 | 277 | 263 | 57 | |

HvCD37-6b15.1.1 MFIR values were not calculated for those populations comprising less than 0.1% of the total sample.

TABLE VIII

Cell Population for HvCD37-6b15.1.1 Binding in AML Patient Samples.
% Populations in Patient Samples

| | sample | Type | % CD45+ | % CD33+ | % CD34+/38− | % CD3 | % CD20 |
|---|---|---|---|---|---|---|---|
| AML | 502 | M1 | 39.50 | 97.10 | 11.10 | 0.43 | 0.70 |
| | 596 | M1 | 95.80 | 96.40 | 0.29 | 1.64 | 0.74 |
| | 598 | M5b | 99.70 | 96.70 | 2.01 | 1.29 | 0.60 |
| | 80534 | M5a | 92.70 | 98.10 | 4.60 | 1.49 | 0.02 |
| | 90165 | M6 | 81.00 | 90.20 | 19.80 | 0.01 | 0.45 |
| | 90191 | M1 | 99.50 | 91.10 | 5.23 | 1.31 | 1.46 |
| | 90392 | M5a | 99.60 | 94.40 | 0.05 | 0.01 | 1.92 |
| | 90429 | M4 | 99.00 | 87.00 | 10.10 | 6.24 | |
| | 90454 | M1 | 99.50 | 91.00 | 1.60 | 3.99 | 1.33 |
| | 90481 | M5a | 96.50 | 82.80 | 5.85 | 1.33 | 0.27 |
| | 90543 | M2 | 98.20 | 93.70 | 0.55 | 1.28 | 0.55 |
| | 90686 | M5a | 93.80 | 83.90 | 0.78 | 9.97 | 2.63 |
| | 100016 | M5a | 99.40 | 88.70 | 0.02 | 6.84 | 1.23 |
| | 100091 | M4 | 96.90 | 95.50 | 14.70 | 0.02 | 2.21 |
| | 100183 | M5a | 99.30 | 98.00 | 0.33 | 0.00 | 0.82 |
| | 100474 | M5a | 97.50 | 94.70 | 0.40 | 2.25 | 0.19 |
| | 100454 | Unclassified | 99.50 | 79.00 | 0.59 | 15.90 | 0.93 |
| | 110283 | M5a | 97.70 | 84.00 | 61.90 | 6.53 | 0.47 |
| | 110484 | M1 | 99.50 | 92.40 | 0.07 | 2.55 | 1.57 |
| | 110500 | M5a | 99.00 | 97.00 | 0.37 | 1.10 | 1.00 |
| | 120277 | M4Eo | 87.50 | 95.40 | 24.50 | 2.77 | |
| | 120287 | M1 | 99.60 | 93.80 | 0.03 | 2.24 | |
| | 120298 | Unclassified | 99.30 | 92.20 | 0.01 | 2.45 | |
| | 120314 | M4 | 99.40 | 82.60 | 0.96 | 8.88 | |
| | 120321 | M1 | 99.00 | 86.30 | 2.38 | 4.68 | |
| | 120409 | M1 | 97.30 | 84.10 | 0.30 | 13.90 | |

The invention claimed is:

1. An antibody or antigen binding fragment thereof that binds to a CD37 protein, wherein the antibody or antigen binding fragment thereof comprises a heavy chain variable region comprising complementarity determining regions (CDRs) having the amino acid sequences of the CDRs in the heavy chain variable region sequence set forth in SEQ ID NO: 7 according to Kabat numbering and a light chain variable region comprising CDRs having the amino acid sequences of the CDRs in the light chain variable region sequence set forth in SEQ ID NO: 8 according to Kabat numbering.

2. The antibody or antigen binding fragment thereof of claim 1, wherein the antibody or antigen binding fragment thereof comprises the heavy chain variable region consisting of the amino acid sequence ranging from residue 1 to residue 115 of SEQ ID NO: 7 and the light chain variable region consisting of the amino acid sequence ranging from residue 1 to residue 106 of SEQ ID NO: 8.

3. The antibody of claim 1, wherein the antibody comprises the heavy chain consisting of the amino acid sequence ranging from residue 1 to residue 441 of SEQ ID NO: 7 and the light chain consisting of the amino acid sequence ranging from residue 1 to residue 212 of SEQ ID NO: 8.

4. An antibody or antigen binding fragment thereof that binds to a CD37 protein, and wherein the antibody or antigen binding fragment thereof comprises a heavy chain variable region comprising complementarity determining regions (CDRs) consisting of the amino acid sequences of the CDRs in the heavy chain variable region of an antibody produced by a Chinese Hamster Ovary (CHO) cell deposited under American Type Culture Collection (ATCC) Accession No. PTA-120464 according to Kabat numbering, and a light chain variable region comprising CDRs consisting of the amino acid sequences of the CDRs in the light chain variable region of an antibody produced by a Chinese Hamster Ovary (CHO) cell deposited under ATCC Accession No. PTA-120464 according to Kabat numbering.

5. The antibody or antigen binding fragment thereof of claim 4, wherein the antibody or antigen binding fragment thereof comprises a heavy chain variable region comprising the amino acid sequence of the heavy chain variable region of an antibody produced by a Chinese Hamster Ovary (CHO) cell deposited under American Type Culture Collection (ATCC) Accession No. PTA-120464, and a light chain variable region comprising the amino acid sequence of the light chain variable region of an antibody produced by a Chinese Hamster Ovary (CHO) cell deposited under ATCC Accession No. PTA-120464.

6. The antibody of claim 4, wherein the antibody comprises a heavy chain consisting of the amino acid sequence of the heavy chain of an antibody produced by a Chinese Hamster Ovary (CHO) cell deposited under ATCC. Accession No. PTA-120464, and a light chain consisting of the amino acid sequence of the light chain of an antibody produced by a Chinese Hamster Ovary (CHO) deposited under ATCC Accession No. PTA-120464.

7. The antibody or antigen binding fragment thereof of claim 1, wherein the antigen binding fragment thereof is an Fab, F(ab')2, Fv or scFv fragment.

8. The antibody or antigen binding fragment thereof of claim 1, wherein the antibody or antigen binding fragment thereof is a fully human antibody or antigen binding fragment thereof.

9. The antibody or antigen binding fragment thereof of claim 1, wherein the antibody or antigen binding fragment thereof is recombinantly produced.

10. The antibody or antigen binding fragment thereof of claim 1, wherein residue 1 of the heavy chain variable region is a pyroglutamate.

11. An antibody drug conjugate comprising the antibody or antigen binding fragment thereof of claim 1 conjugated to 1 to 20 moieties of a cytotoxic agent, each moiety being conjugated via a linker.

12. The antibody drug conjugate of claim 11, wherein the cytotoxic agent is monomethyl auristatin E (MMAE).

13. The antibody drug conjugate of claim 12, wherein the linker has a formula of: $-A_a-W_w-Y_y-$; wherein -A- is a stretcher unit, a is 0 or 1; —W— is an amino acid unit, w is an integer ranging from 0 to 12; and —Y— is a spacer unit, y is 0, 1, or 2; wherein the stretcher unit has the structure of Formula (1) below; the amino acid unit is valine citrulline; and the spacer unit is a PAB group having the structure of Formula (2) below;

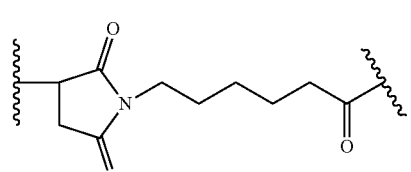

Formula (1)

Formula (2)

wherein the stretcher unit forms a bond with a sulfur atom of the antibody or antigen binding fragment thereof; and wherein the space unit is linked to MMAE via a carbamate group.

14. The antibody drug conjugate of claim 13, wherein the antibody or antigen binding fragment thereof is conjugated to MMAE via an enzyme-cleavable linker, and wherein the linker forms a bond with a sulfur atom of the antibody or antigen binding fragment thereof.

15. The antibody drug conjugate of claim 14, wherein the linker comprises valine-citrulline.

16. The antibody drug conjugate of claim 12, wherein the antibody drug conjugate has the following structure:

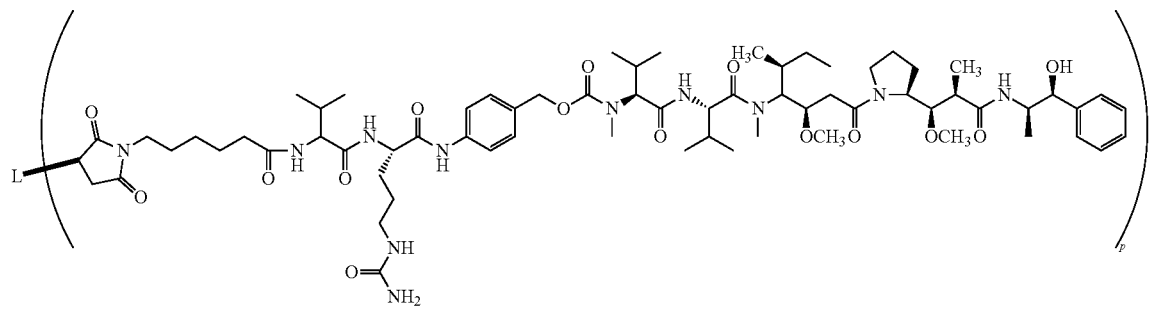

wherein L- represents the antibody or antigen binding fragment thereof and p ranges from 2 to about 8.

17. The antibody drug conjugate of claim 16, wherein p ranges from 2 to 5.

18. A method of treating a CD37 expressing cancer in a subject, comprising administering to said subject the antibody drug conjugate of claim 16.

19. A method of treating a CD37 expressing cancer in a subject, comprising administering to said subject an effective amount of a combination of the antibody drug conjugate of claim 16 and radiation.

20. A method of treating a CD37 expressing cancer in a subject, comprising administering to said subject an effective amount of a combination of the antibody drug conjugate of claim 16 and a chemotherapeutic agent.

21. The method of claim 18, wherein the subject is a human subject.

22. The method of claim 21, wherein the CD37 expressing cancer is selected from the group consisting of Non-Hodgkin's lymphoma, chronic lymphocytic leukemia, acute myeloid leukemia, and multiple myeloma.

* * * * *